(12) United States Patent
Kosinski et al.

(10) Patent No.: US 11,905,228 B2
(45) Date of Patent: Feb. 20, 2024

(54) SALTS OF DIAMINOACETALS AND DIAMINOKETALS AND THEIR SYNTHESIS, AND THEIR TRANSFORMATIONS TO DIAMINOACETALS AND DIAMINOKETALS

(71) Applicant: Aditya Birla Chemicals (USA), Inc., Florence, KY (US)

(72) Inventors: Szymon Kosinski, Hayward, CA (US); Stefan J. Pastine, Berkeley, CA (US); Ulhas Bhatt, Fremont, CA (US)

(73) Assignee: Aditya Birla Chemicals (USA), Inc., Florence, KY (US)

( * ) Notice: Subject to any disclaimer, the term of this patent is extended or adjusted under 35 U.S.C. 154(b) by 0 days.

(21) Appl. No.: 17/394,935

(22) Filed: Aug. 5, 2021

(65) Prior Publication Data
US 2022/0024854 A1 Jan. 27, 2022

Related U.S. Application Data

(63) Continuation of application No. 16/005,514, filed on Jun. 11, 2018, now Pat. No. 11,124,473.

(60) Provisional application No. 62/530,933, filed on Jul. 11, 2017.

(51) Int. Cl.
| | | |
|---|---|---|
| C07C 217/08 | (2006.01) | |
| C07C 213/08 | (2006.01) | |
| C08G 59/50 | (2006.01) | |
| C08J 11/26 | (2006.01) | |
| C08G 59/06 | (2006.01) | |
| C08G 59/40 | (2006.01) | |
| C08J 11/16 | (2006.01) | |

(52) U.S. Cl.
CPC .......... *C07C 217/08* (2013.01); *C07C 213/08* (2013.01); *C08G 59/066* (2013.01); *C08G 59/4085* (2013.01); *C08G 59/504* (2013.01); *C08J 11/16* (2013.01); *C08J 11/26* (2013.01); *C08J 2363/00* (2013.01); *C08J 2379/02* (2013.01)

(58) Field of Classification Search
CPC ............................ C07C 217/08; C07C 213/08
USPC ......................................................... 564/504
See application file for complete search history.

(56) References Cited

U.S. PATENT DOCUMENTS

| | | |
|---|---|---|
| 2,363,464 A | 11/1944 | Murray et al. |
| 2,409,675 A | 10/1946 | Gresham |
| 2,425,628 A | 8/1947 | Loder et al. |
| 3,293,298 A | 12/1966 | Szabo |
| 3,462,393 A | 8/1969 | Legler |
| 3,501,528 A | 3/1970 | Ott |
| 3,558,709 A | 1/1971 | Gunter |
| 3,786,029 A | 1/1974 | Bechara |
| 3,879,465 A | 4/1975 | Bechara et al. |
| 4,003,933 A | 1/1977 | Drake |
| 4,136,092 A | 1/1979 | Jackle et al. |
| 4,177,173 A | 12/1979 | Carr |
| 4,235,821 A | 11/1980 | Butte, Jr. et al. |
| 4,252,936 A | 2/1981 | Rinde et al. |
| 4,313,004 A | 1/1982 | Kluger et al. |

(Continued)

FOREIGN PATENT DOCUMENTS

| | | |
|---|---|---|
| CN | 102816346 A | 12/2012 |
| CN | 104292501 A | 1/2015 |
| DE | 1125171 B | 3/1962 |
| GB | 846377 A | 8/1960 |
| JP | 1225635 | 9/1989 |
| WO | 2009126933 A2 | 10/2009 |
| WO | 2012071896 A1 | 6/2012 |
| WO | 2012071896 A1 | 4/2021 |

OTHER PUBLICATIONS

Bassampour et al., "Degradable epoxy resins based on bisphenol a diglycidyl ether and silyl ether amine curing agents", Figures, Department of Chemistry, Southern Methodist University.

(Continued)

*Primary Examiner* — Ana Z Muresan
(74) *Attorney, Agent, or Firm* — Goodwin Procter LLP

(57) ABSTRACT

This application relates, in part, to novel salts represented by the following structure of Formula (1):

Formula (1)

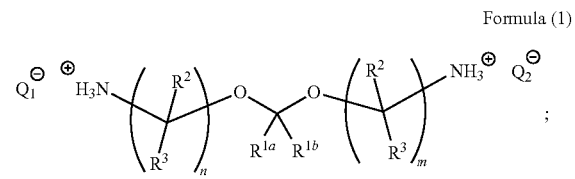

wherein $R^{1a}$ is selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); each occurrence of $R^2$ and $R^3$ is independently selected from the group consisting of hydrogen, optionally substituted alkyl, optionally substituted cycloalkyl, and optionally substituted aryl; $R^2$ and $R^3$ can combine with each other to form optionally substituted cycloalkyl; each m and n is independently an integer ranging from 1 to 20 (e.g., m and n is independently an integer ranging from 1 to 5); and each of $Q^{1\ominus}$ and $Q^{2\ominus}$ is independently a counterion (e.g., each of $Q^{1\ominus}$ and $Q^{2\ominus}$ is independently a counterion selected from the group consisting of chloride, bromide, fluoride, iodide, acetate, carboxylate, hydrogen sulfate, nitrate, and phenolate, and sulfonate, e.g., chloride), and methods of making the same.

17 Claims, 5 Drawing Sheets

(56) References Cited

U.S. PATENT DOCUMENTS

| | | | |
|---|---|---|---|
| 4,328,331 | A | 5/1982 | Chen et al. |
| 4,495,317 | A | 1/1985 | Albers |
| 4,552,815 | A | 11/1985 | Dreher et al. |
| 4,581,423 | A | 4/1986 | Speranza et al. |
| 4,820,743 | A | 4/1989 | Ishikawa et al. |
| 4,929,661 | A | 5/1990 | Noomen et al. |
| 5,191,015 | A | 3/1993 | Sheppard et al. |
| 5,298,618 | A | 3/1994 | Speranza et al. |
| 5,310,789 | A | 5/1994 | Furihata et al. |
| 5,338,568 | A | 8/1994 | Lohnes et al. |
| 5,891,367 | A | 4/1999 | Basheer et al. |
| 5,932,682 | A | 8/1999 | Buchwalter et al. |
| 6,790,995 | B2 | 9/2004 | Pfeffinger et al. |
| 8,785,694 | B2 | 7/2014 | Pastine |
| 9,080,004 | B2 | 7/2015 | Abrami et al. |
| 9,631,049 | B2 | 4/2017 | Pastine et al. |
| 9,862,797 | B2 | 1/2018 | Pastine |
| 10,214,479 | B2 | 2/2019 | Kosinski et al. |
| 2002/0045057 | A1 | 4/2002 | Guritza |
| 2005/0234216 | A1 | 10/2005 | Klein et al. |
| 2006/0014924 | A1 | 1/2006 | Hanley et al. |
| 2008/0207655 | A1 | 8/2008 | Dillon et al. |
| 2009/0030125 | A1 | 1/2009 | Vedage et al. |
| 2009/0048370 | A1 | 2/2009 | Lutz et al. |
| 2009/0137777 | A1 | 5/2009 | Iwashima et al. |
| 2009/0192265 | A1 | 7/2009 | Hasegawa et al. |
| 2010/0184890 | A1 | 7/2010 | Constantinescu et al. |
| 2011/0048637 | A1 | 3/2011 | Kohli |
| 2011/0244245 | A1 | 10/2011 | Elgimiabi |
| 2012/0012505 | A1 | 1/2012 | Compton |
| 2012/0301726 | A1 | 11/2012 | Staunton et al. |
| 2013/0245204 | A1 | 9/2013 | Pastine et al. |
| 2013/0324764 | A1 | 12/2013 | Pastine |
| 2014/0221510 | A1 | 8/2014 | Liang et al. |
| 2014/0357802 | A1 | 12/2014 | Aou et al. |
| 2015/0050659 | A1 | 2/2015 | Sebo et al. |
| 2015/0361230 | A1 | 12/2015 | Curran et al. |
| 2016/0229949 | A1 | 8/2016 | Qin et al. |
| 2016/0264717 | A1 | 9/2016 | Pastine |
| 2017/0114002 | A1 | 4/2017 | Pastine |
| 2017/0145180 | A1 | 5/2017 | Liang et al. |
| 2017/0342301 | A1 | 11/2017 | Huang et al. |

OTHER PUBLICATIONS

Bassampour et al., "Degradable epoxy resins based on bisphenol a diglycidyl ether and silyl ether amine curing agents", Journal of Applied Polymer Science, (2017), App 44620, pp. 1-9.

Berge et al., "Pharmaceutical Salts", Journal of Pharmaceutical Sciences, (1977), vol. 66, pp. 1-18.

Bradley et al., "Alkoxides of vanadium (IV)", Canadian Journal of Chemistry (1962), vol. 40, pp. 1183-1188.

Bunyan et al., "Reactivity of organophosphorus compounds. XIII. Radical-chain transfer reactions of triethyl phosphite: a new phosphorothiolate synthesis", Journal of the Chemical Society (1962), pp. 2953-2958.

Emblem et al., "Preparation and properties of some aminoalkoxysilanes", Journal of Applied Chemistry (1962), vol. 12, pp. 5-9.

International Search Report and Written Opinion for corresponding International Application No. PCT/CN2011/076980, dated Oct. 13, 2011.

International Search Report and Written Opinion for corresponding International Application No. PCT/US2013/044346, dated Nov. 5, 2013.

International Search Report and Written Opinion for corresponding International Application No. PCT/US2014/060524, dated Mar. 19, 2015.

International Search Report and Written Opinion for International Application No. PCT/US2019/012543, dated Apr. 24, 2019.

International Search Report and Written Opinion for International Application No. PCT/US2019/012544, dated Apr. 30, 2019.

Paramonov et al., "Fully Acid-Degradable Biocompatible Polyacetal Microparticles for Drug Delivery", Bioconjugate Chem., vol. 19, No. 4, (2008), pp. 911-919.

PubChem. Compound Summary for CID 20541457.

Shim et al., "Acid-Responsive Linear Polyethylenimine for Efficient, Specific, and Biocompatible siRNA Delivery", Bioconjugate Chem., vol. 20, No. 3, (2009), pp. 488-499.

Webb et al., Journal of the Chemical Society Journal (1962), pp. 4307-4319.

Webb et al., Journal of the Chemical Society Journal (1962), pp. 4320-4323.

U.S. Appl. No. 13/910,612, Processes for the Preparation of Di-(2-Aminoethyl) Formal, Di-(3-Aminopropyl) Formal, and Related Molecules, filed Jun. 5, 2013, Issued.

U.S. Appl. No. 15/397,521, Synthesis of and Compositions Containing Diaminoacetals and Diaminoketals, filed Jan. 3, 2017, Issued.

U.S. Appl. No. 16/239,110, Synthesis of and Compositions Containing Diaminoacetals and Diaminoketals, filed Jan. 3, 2019, Pending.

U.S. Appl. No. 16/852,056, Synthesis of and Compositions Containing Diaminoacetals and Diaminoketals, filed Apr. 17, 2020, Pending.

U.S. Appl. No. 13/988,817, Novel Agents for Reworkable Epdxy Resins, filed Jul. 8, 2011, Issued.

U.S. Appl. No. 14/114,140, Reinforced Composite and Method for Recycling the Same, filed May 4, 2012, Issued.

U.S. Appl. No. 15/028,342, Sterically Hindered Aliphatic Polyamine Cross-Linking Agents, Compositions Containing Them and Uses Thereof, filed Oct. 14, 2014, Issued.

U.S. Appl. No. 16/005,550, Silicon-Containing Compositions and Their Methods of Use, filed Jun. 11, 2018, Issued.

U.S. Appl. No. 17/087,477, Silicon-Containing Compositions and Their Methods of Use, filed Nov. 2, 2020, Pending.

Examples of Acetone Equivlanets

R = alkyl

Specific Examples

Examples of Acetaldehyde Equivlanets

R = alkyl

SALTS OF DIAMINOACETALS AND DIAMINOKETALS AND THEIR SYNTHESIS, AND THEIR TRANSFORMATIONS TO DIAMINOACETALS AND DIAMINOKETALS

CROSS-REFERENCE TO RELATED APPLICATIONS

This application is a continuation of U.S. Ser. No. 16/005,514 filed Jun. 11, 2018, which claims priority to U.S. Ser. No. 62/530,933 filed Jul. 11, 2017, the contents of which are incorporated herein by reference.

FIELD OF THE INVENTION

The present invention generally relates to the chemical synthesis of polyamine compounds, in particular chemical synthesis of diaminoacetal and diaminoketal compounds in their ammonium salt and free-base forms.

BRIEF SUMMARY OF THE INVENTION

In one aspect, described herein is a salt of Formula (1):

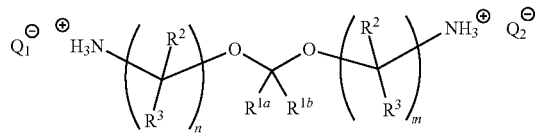

Formula (1)

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2); and each of $Q^{1\ominus}$ and $Q^{2\ominus}$ is independently a counterion (e.g., each of $Q^{1\ominus}$ and $Q^{2\ominus}$ is independently a counterion selected from the group consisting of chloride, bromide, fluoride, iodide, acetate, carboxylate, hydrogen sulfate, nitrate, and phenolate, and sulfonate, e.g., chloride).

In one aspect, described herein is a compound of Formula (2):

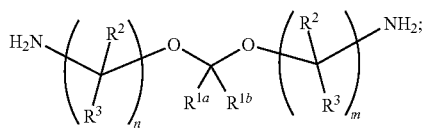

Formula (2)

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2); and salts thereof.

In one aspect, described herein is a compound represented by Formula (2-a):

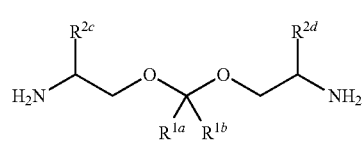

Formula (2-a)

wherein: $R^{1a}$ is independently selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); and each of $R^{2c}$ and $R^{2d}$ is independently selected from optionally substituted alkyl (e.g., unsubstituted $C_{1-6}$ alkyl, e.g., unsubstituted $C_{1-6}$ alkyl selected from the group consisting of —$CH_3$ and —$CH_2CH_3$); and salts thereof.

In another aspect, described herein is a process for the preparation of a compound represented by Formula (2) below:

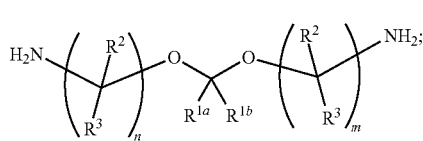

Formula (2)

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2).

In one embodiment, the process comprises a step of providing a salt represented by Formula (1). In one embodiment, the process comprises a step of converting the salt of Formula (1) into its freebase form, which has the structure of Formula (2). In one embodiment, the process comprises contacting a salt (e.g., a diammonium salt) of the compound of Formula (2) with a base (e.g., sodium hydroxide) to produce the compound of Formula (2).

In one aspect, described herein is a process for preparing a salt of a compound represented by Formula (2-1):

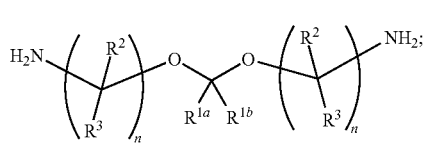

Formula (2-1)

wherein $R^{1a}$ is selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each instance of n is the same integer ranging from 1 to 20, the process comprising: or the reaction of an aldehyde equivalent or ketone equivalent with a salt of the compound of Formula (3):

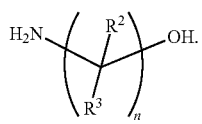

Formula (3)

In another aspect, described herein is a process for preparing a salt of a compound represented by Formula (2-1):

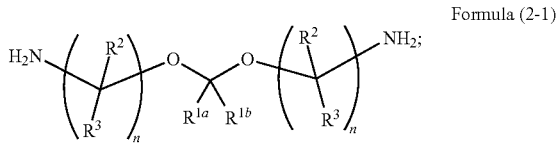

Formula (2-1)

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each instance of n is the same integer ranging from 1 to 20, the process comprising the process comprising reacting a compound of Formula (3) with a compound of Formula (4) in the presence of an acid to produce the salt of a compound of Formula (2-1);

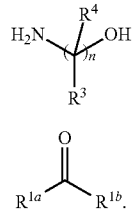

Formula (3)

Formula (4)

In an aspect, described herein is an epoxy resin composition comprising the product of an epoxy resin and an aliphatic polyamine (e.g., as a cross-linking agent), wherein the aliphatic polyamine comprises (e.g., consists of) a compound having the structure of Formula (2):

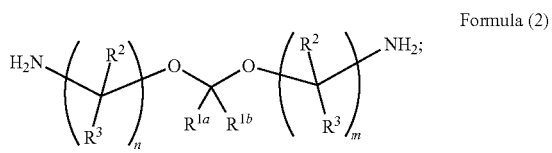

Formula (2)

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2).

In an aspect, described herein is an epoxy resin composition comprising the product of an epoxy resin and an aliphatic polyamine (e.g., as a cross-linking agent), wherein the aliphatic polyamine comprises (e.g., consists of) a compound having the structure of Formula (2-a):

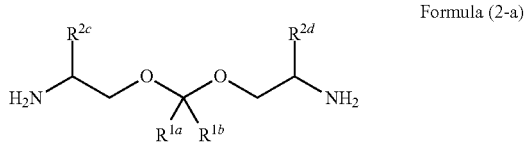

Formula (2-a)

wherein: $R^{1a}$ is independently selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); and each of $R^{2c}$ and $R^{2d}$ is independently selected from optionally substituted alkyl (e.g., unsubstituted $C_{1-6}$ alkyl, e.g., unsubstituted $C_{1-6}$ alkyl selected from the group consisting of —$CH_3$ and —$CH_2CH_3$).

In an aspect, described herein is a cross-linked polymer matrix derived from an epoxy resin and an aliphatic polyamine cross-linking agent comprising a compound having the structure represented by Formula (2):

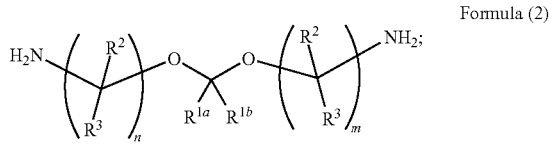

Formula (2)

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2).

In an aspect, described herein is a cross-linked polymer matrix derived from an epoxy resin and an aliphatic polyamine cross-linking agent comprising a compound having the structure represented by Formula (2-a):

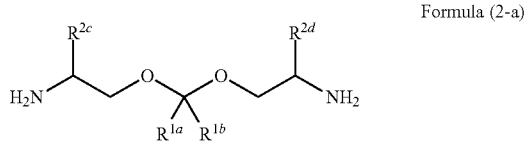

Formula (2-a)

wherein: $R^{1a}$ is independently selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); and each of $R^{2c}$ and $R^{2d}$ is independently selected from optionally substituted alkyl (e.g., unsubstituted $C_{1-6}$ alkyl, e.g., unsubstituted $C_{1-6}$ alkyl selected from the group consisting of —$CH_3$ and —$CH_2CH_3$).

DETAILED DESCRIPTION

Figure 1:
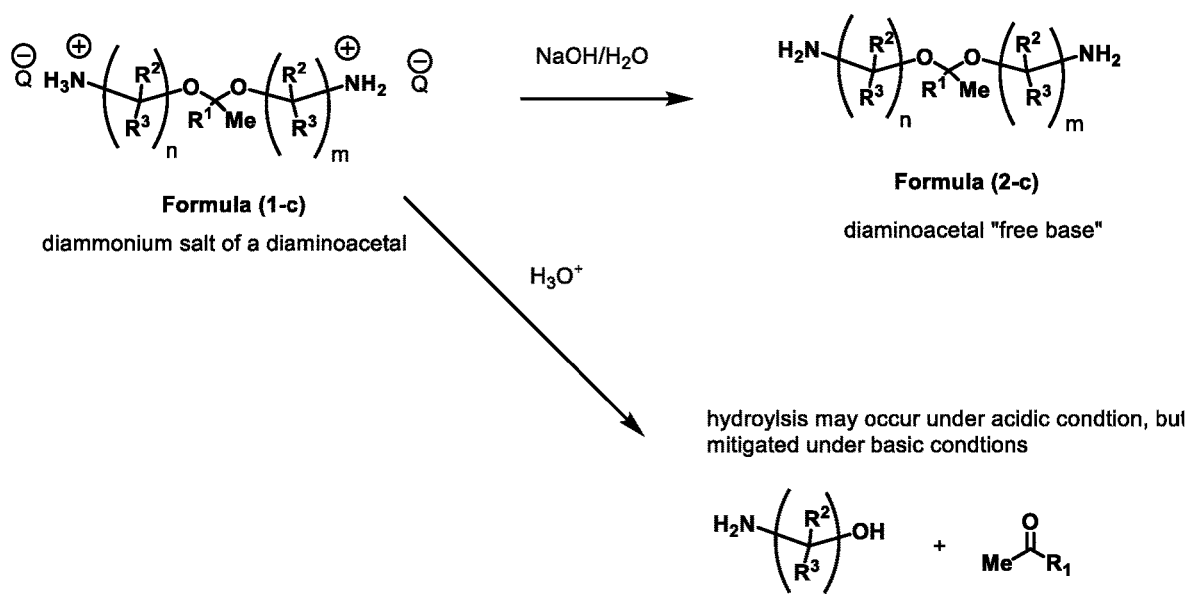
FIG. 1 depicts an exemplary conversion of a diammonium salt of a diaminoacetal into its free base form, and without hydrolysis of the acetal/ketal functional group.

The present subject matter will now be described more fully hereinafter with reference to the accompanying Figures and Examples, in which representative embodiments are shown. The present subject matter can, however, be embodied in different forms and should not be construed as limited to the embodiments set forth herein. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entirety.

A polyamine of Formula (2) represents a class of diamine molecules, more specifically diaminoketals and diaminoacetals. The polyamine of Formula (2) encompasses a molecular genus that possesses an acid-labile group, which connects two primary amine groups. In one embodiment, the polyamine of Formula (2) comprises a diaminoacetal. In one embodiment, the polyamine of Formula (2) comprises a diaminoketal. Thus, a polyamine according to Formula (2) may contain an acetal group or ketal group that serves to link alkyl amino groups.

A polyamine of Formula (2) is useful as a monomer or a cross-linker in the manufacturing of polymeric materials such as nylons, epoxies, polyurethanes, acrylamides and other types of polymers, cross-linked polymers, and materials. Accordingly, a polyamine of Formula (2) can be used as a monomer or cross-linker in the chemical synthesis of designer materials. An advantage of designer materials incorporating the polyamine of Formula (2) is that they are degradable under acidic conditions. Such designer materials can be predictably degraded under controlled conditions owing to the presence of acid labile acetal and/or ketal linkages in the materials. Another advantage of designer materials incorporating the polyamine of Formula (2) is that they can be used as drug delivery systems. In this regard, the rate of acid hydrolysis of acetal and/or ketal linkages in a designer material incorporating the polyamine of Formula (2) can be used to fine-tune physical properties of a drug delivery system. Moreover, differences between the rates of acid hydrolysis of acetals and ketals (in general the rate of acid hydrolysis decreases in the order of ketal>acetal) can be exploited to control rate of degradation of the polymeric materials of drug delivery systems.

Compounds

In an aspect, described herein is a salt represented by Formula (1):

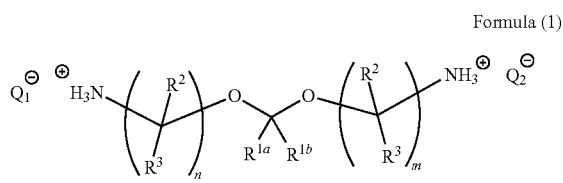

Formula (1)

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; each m and n is independently an integer ranging from 1 to 20 (e.g., m and n is independently an integer ranging from 1 to 5); and each of $Q^{1\ominus}$ and $Q^{2\ominus}$ is independently a counterion (e.g., each of $Q^{1\ominus}$ and $Q^{2\ominus}$ is independently a counterion selected from the group consisting of chloride, bromide, fluoride, iodide, acetate, carboxylate, hydrogen sulfate, nitrate, and phenolate, and sulfonate, e.g., chloride).

In some embodiments, $R^{1a}$ is selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); each occurrence of $R^2$ and $R^3$ is independently selected from the group consisting of hydrogen, optionally substituted alkyl, optionally substituted cycloalkyl, and optionally substituted aryl; or $R^2$ and $R^3$ can combine with each other to form optionally substituted cycloalkyl; each m and n is independently an integer ranging from 1 to 20 (e.g., m and n is independently an integer ranging from 1 to 5); and each of $Q^{1\ominus}$ and $Q^{2\ominus}$ is independently a counterion (e.g., each of $Q^{1\ominus}$ and $Q^{2\ominus}$ is independently a counterion selected from the group consisting of chloride, bromide, fluoride, iodide, acetate, carboxylate, hydrogen sulfate, nitrate, and phenolate, and sulfonate, e.g., chloride).

In one embodiment, n is 2. In one embodiment, m is 2. In some embodiments, $Q^{1\ominus}$ and $Q^{2\ominus}$ are the same counterion. In some embodiments, $Q^{1\ominus}$ and $Q^{2\ominus}$ are selected from the group consisting of chloride, bromide, fluoride, and iodide. In some embodiments, $Q^{1\ominus}$ and $Q^{2\ominus}$ are both chloride. In some embodiments, $Q^{1\ominus}$ and $Q^{2\ominus}$ are both acetate. In some embodiments, m and n are the same integer (e.g., m and n are both 2).

In one embodiment, the salt of Formula (1) is represented by Formula (1-a):

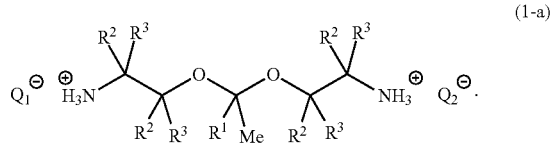
(1-a)

In one embodiment, the salt of Formula (1) is represented by Formula (1-a-I):

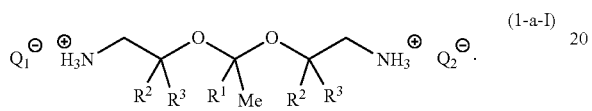
(1-a-I)

In one embodiment, the salt of Formula (1) is represented by Formula (1-a-II):

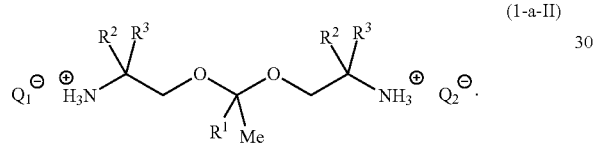
(1-a-II)

In one embodiment, the salt of Formula (1) is represented by Formula (1-b):

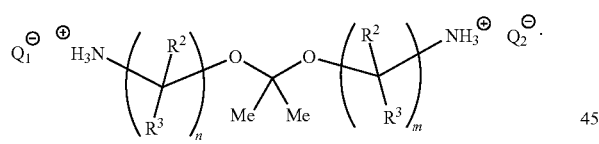
(1-b)

In one embodiment, the salt of Formula (1) is represented by Formula (1-b-I):

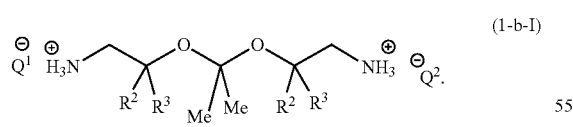
(1-b-I)

In one embodiment, the salt of Formula (1) is represented by Formula (1-b-I-A):

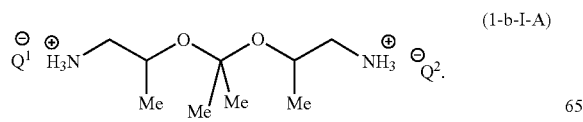
(1-b-I-A)

In one embodiment, the salt of Formula (1) is represented by Formula (1-b-I-B):

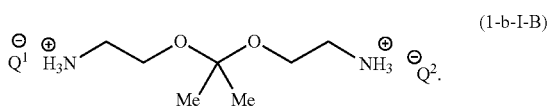
(1-b-I-B)

In one embodiment, the salt of Formula (1) is represented by Formula (1-b-II):

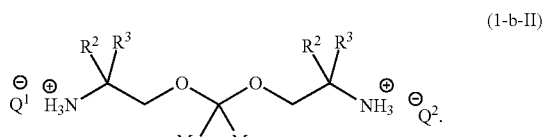
(1-b-II)

In one embodiment, the salt of Formula (1) is represented by Formula (1-b-II-A):

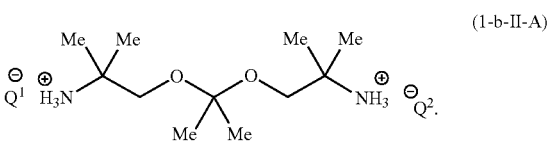
(1-b-II-A)

In one embodiment, the salt of Formula (1) is represented by Formula (1-b-II-B):

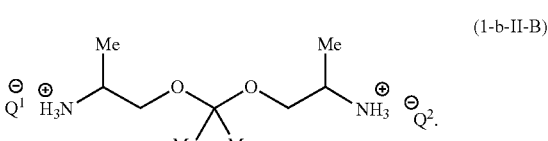
(1-b-II-B)

In a preferred embodiment of any of the forgoing, $Q^{1\ominus}$ and $Q^{2\ominus}$ are both chloride. In one embodiment of any of the foregoing, $Q^{1\ominus}$ and $Q^{2\ominus}$ are both acetate.

In some embodiments, the salt represented by Formula (1) is a salt of Formula (1-c)

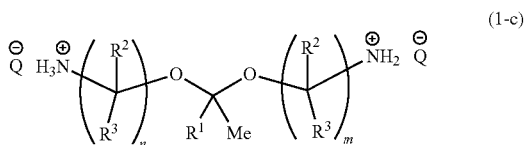
(1-c)

wherein $Q^{\ominus}$ is a suitable counterion (e.g., a counterion selected from the group consisting of chloride, bromide, fluoride, iodide, acetate, carboxylate, hydrogen sulfate, nitrate, and phenolate, and sulfonate, e.g., chloride).

In some embodiments, the salt represented by Formula (1) is a salt of Formula (1-d)

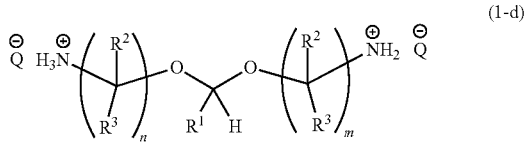
(1-d)

wherein $Q^\ominus$ is a suitable counterion (e.g., a counterion selected from the group consisting of chloride, bromide, fluoride, iodide, acetate, carboxylate, hydrogen sulfate, nitrate, and phenolate, and sulfonate, e.g., chloride).

In some embodiments, the salt of Formula (1) is selected from the group consisting of:

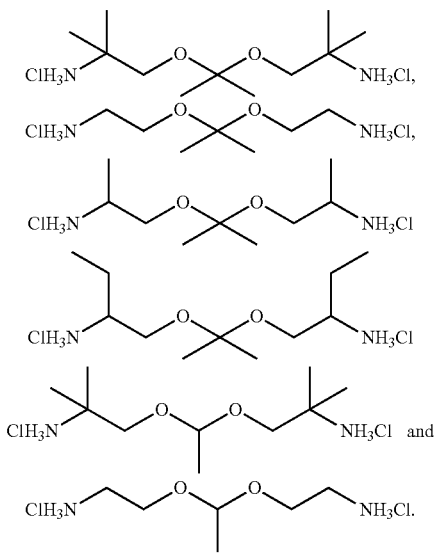

In an aspect, described herein is a compound represented by Formula (2):

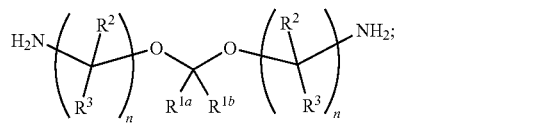

Formula (2)

wherein each of $R^{1a}$ and $R^{1b}$ is independently selected from the group consisting of hydrogen, optionally substituted alkyl (e.g., unsubstituted $C_{1-6}$ alkyl, e.g., —CH$_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2); and salts thereof.

In some embodiments, $R^{1a}$ is selected from the group consisting of hydrogen and optionally substituted alkyl (e.g., unsubstituted $C_{1-6}$ alkyl, e.g., —CH$_3$); $R^{1b}$ is optionally substituted alkyl (e.g., unsubstituted $C_{1-6}$ alkyl, e.g., —CH$_3$); each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2).

In some embodiments, $R^{1a}$ is hydrogen and $R^{1b}$ is optionally substituted $C_{1-6}$ alkyl. In some embodiments, $R^{1a}$ is hydrogen and $R^{1b}$ is unsubstituted $C_{1-6}$ alkyl. In some embodiments, each of $R^{1a}$ and $R^{1b}$ is independently selected from unsubstituted $C_{1-6}$ alkyl. In some embodiments, $R^{1b}$ is —CH$_3$. In some embodiments, each occurrence of $R^2$ and $R^3$ is independently selected from unsubstituted $C_{1-6}$ alkyl. In some embodiments, $R^2$ is hydrogen and $R^3$ is unsubstituted $C_{1-6}$ alkyl (e.g., —CH$_3$ or —CH$_2$CH$_3$). In one embodiment, m is 2. In one embodiment, n is 2. In one embodiment, m is 2 and n is 2. In some embodiments, m and n are the same integer (e.g., m and n are both 2).

In some embodiments, the compound of Formula (2) is represented by a compound of Formula (2-a):

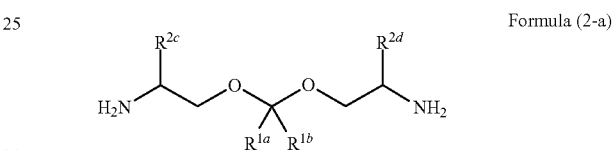

Formula (2-a)

wherein $R^{1a}$ is independently selected from the group consisting of hydrogen and optionally substituted alkyl (e.g., unsubstituted $C_{1-6}$ alkyl, e.g., —CH$_3$); $R^{1b}$ is optionally substituted alkyl (e.g., unsubstituted $C_{1-6}$ alkyl, e.g., —CH$_3$); and each of $R^{2c}$ and $R^{2d}$ is independently selected from optionally substituted alkyl (e.g., unsubstituted $C_{1-6}$ alkyl, e.g., unsubstituted $C_{1-6}$ alkyl selected from the group consisting of —CH$_3$ and —CH$_2$CH$_3$); and salts thereof.

In some embodiments, $R^{1a}$ is hydrogen and $R^{1b}$ is unsubstituted $C_{1-6}$ alkyl.

In some embodiments, each of $R^{1a}$ and $R^{1b}$ is independently selected from unsubstituted $C_{1-6}$ alkyl. In some embodiments, each of $R^{2c}$ and $R^{2d}$ is independently selected from unsubstituted $C_{1-6}$ alkyl.

In some embodiments, the compound is selected from the group consisting of the compound represented by the Formula (2-a-I) and the compound represented by Formula (2-a-II):

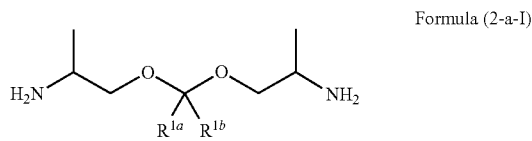

Formula (2-a-I)

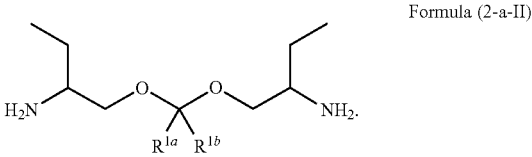

Formula (2-a-II)

In some embodiments, the compound is selected from the group consisting of the compound represented by the Formula (2-a-I):

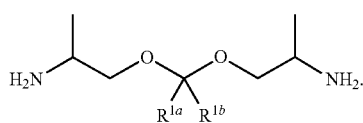
Formula (2-a-I)

In some embodiments, the compound is selected from the group consisting of the compound represented by the compound represented by Formula (2-a-II):

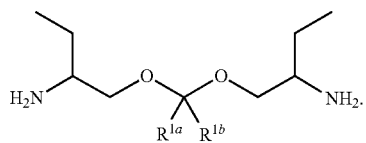
Formula (2-a-II)

In some embodiments, the compound is selected from the group consisting of the compound represented by the Formula (2-a-I-a) and the compound represented by Formula (2-a-II-a):

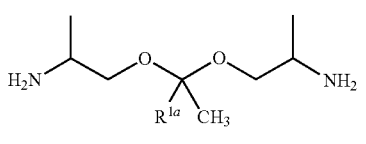
Formula (2-a-I-a)

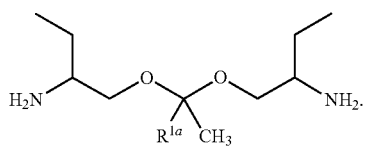
Formula (2-a-II-a)

In some embodiments, the compound is selected from the group consisting of the compound represented by the Formula (2-a-I-a):

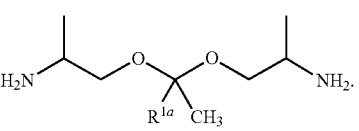
Formula (2-a-I-a)

In some embodiments, the compound is selected from the group consisting of the compound represented by the compound represented by Formula (2-a-II-a):

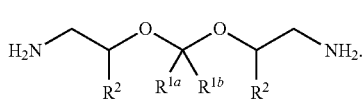
Formula (2-a-II-a)

In one embodiment, the compound is represented by the Formula (2-b):

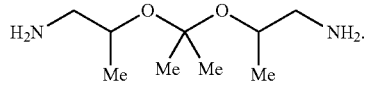
Formula (2-b)

In one embodiment, the compound is represented by the compound is:

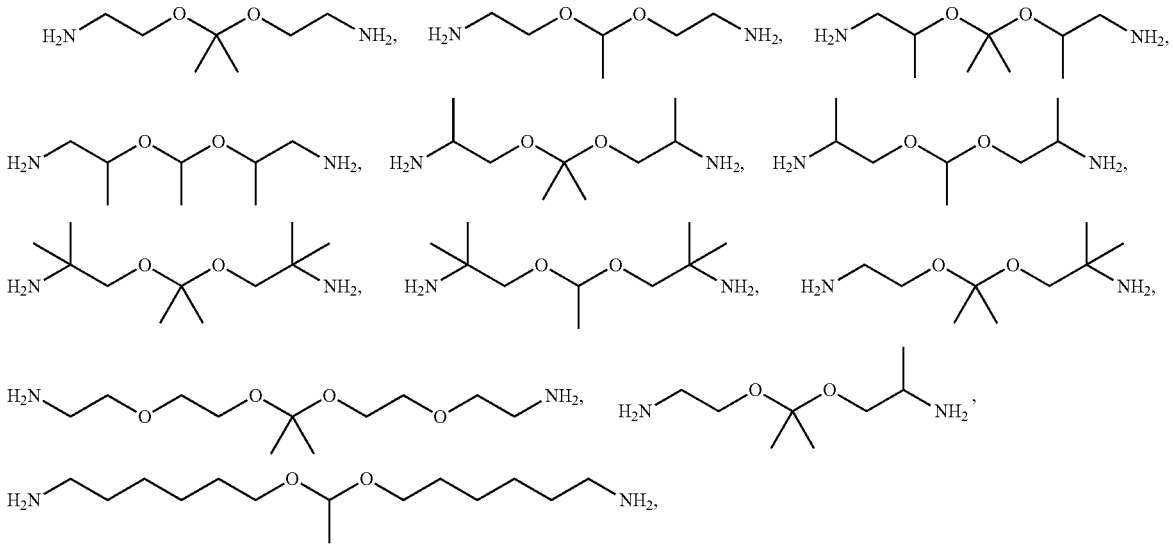

Exemplary compounds represented by Formula (2) include, but are not limited to, the following:

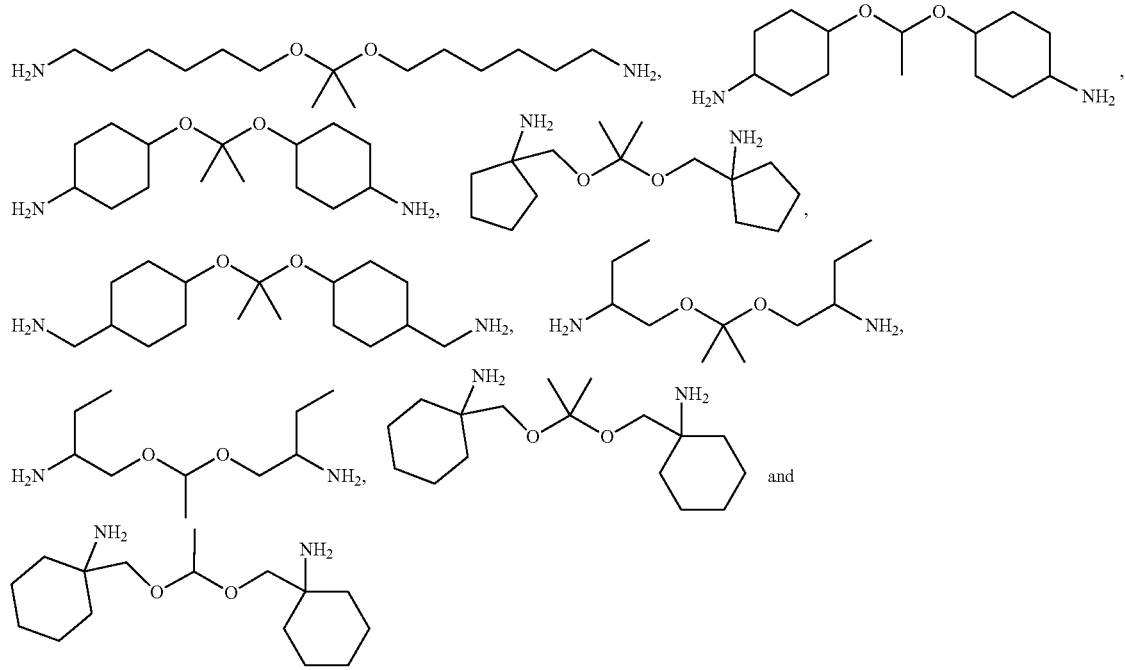
In one embodiment, the compound represented by Formula (2) is selected from the group consisting of:
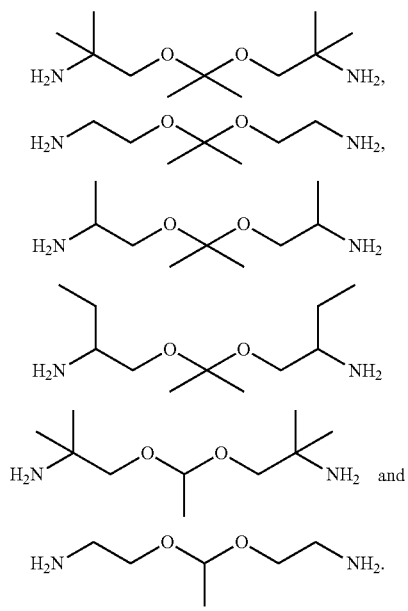
In some embodiments, the compound is selected from the group consisting of
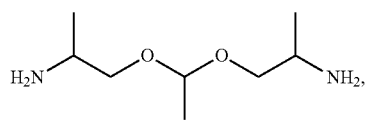
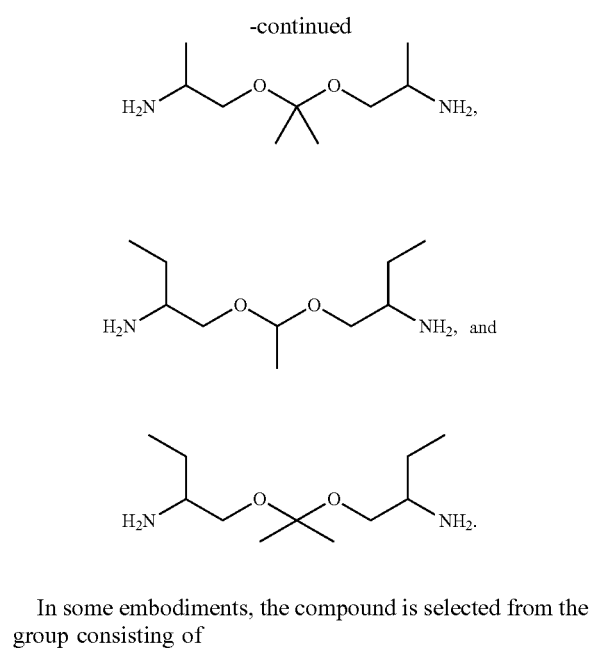
In some embodiments, the compound is selected from the group consisting of
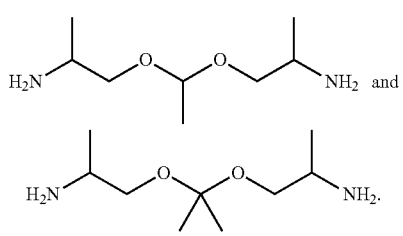
In some embodiments, the compound is selected from the group consisting of

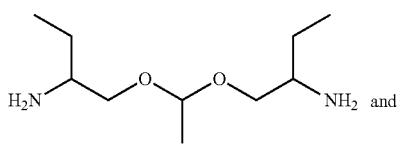

and

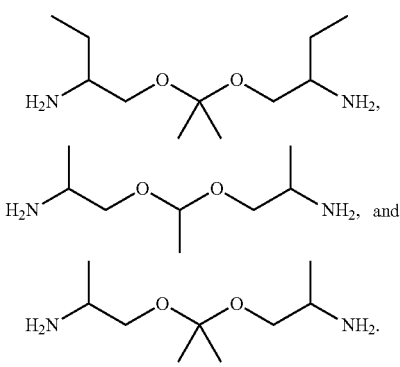

In some embodiments, the compound is selected from the group consisting of

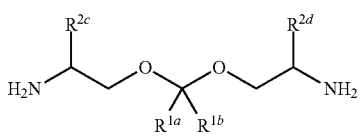

In one aspect, described herein is a compound represented by Formula (2-a):

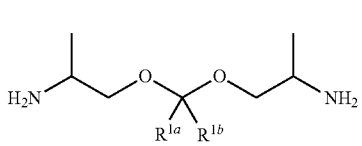

Formula (2-a)

wherein $R^{1a}$ is independently selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); and each of $R^{2c}$ and $R^{2d}$ is independently selected from optionally substituted alkyl (e.g., unsubstituted $C_{1-6}$ alkyl, e.g., unsubstituted $C_{1-6}$ alkyl selected from the group consisting of —$CH_3$ and —$CH_2CH_3$); and salts thereof.

In some embodiments, $R^{1a}$ is hydrogen and $R^{1b}$ is unsubstituted $C_{1-6}$ alkyl.

In some embodiments, each of $R^{1a}$ and $R^{1b}$ is independently selected from unsubstituted $C_{1-6}$ alkyl. In some embodiments, each of $R^{2c}$ and $R^{2d}$ is independently selected from unsubstituted $C_{1-6}$ alkyl.

In some embodiments, the compound is selected from the group consisting of the compound represented by the Formula (2-a-I) and the compound represented by Formula (2-a-II):

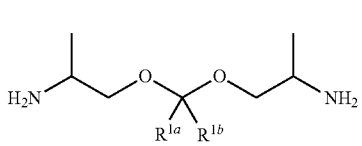

Formula (2-a-I)

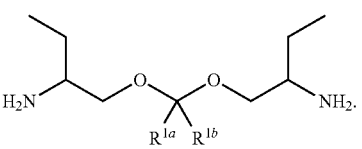

Formula (2-a-II)

In some embodiments, the compound is selected from the group consisting of the compound represented by the Formula (2-a-I):

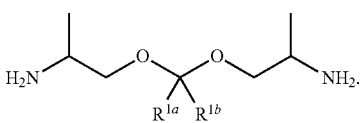

Formula (2-a-I)

In some embodiments, the compound is selected from the group consisting of the compound represented by the compound represented by Formula (2-a-II):

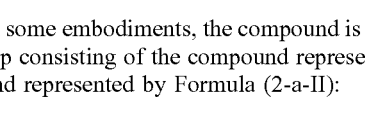

Formula (2-a-II)

In some embodiments, the compound is selected from the group consisting of the compound represented by the Formula (2-a-I-a) and the compound represented by Formula (2-a-II-a):

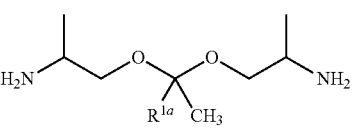

Formula (2-a-I-a)

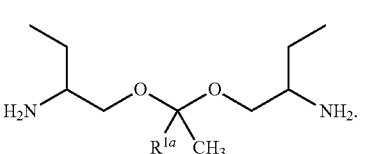

Formula (2-a-II-a)

In some embodiments, the compound is selected from the group consisting of the compound represented by the Formula (2-a-I-a):

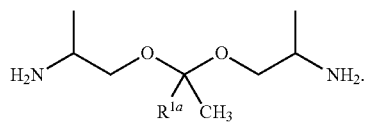

Formula (2-a-I-a)

In some embodiments, the compound is selected from the group consisting of the compound represented by the compound represented by Formula (2-a-II-a):

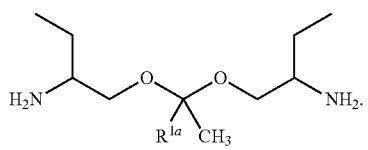

Formula (2-a-II-a)

In some embodiments, the compound is selected from the group consisting of

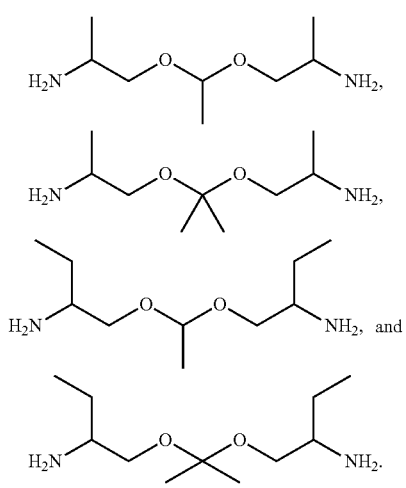

In some embodiments, the compound is selected from the group consisting of

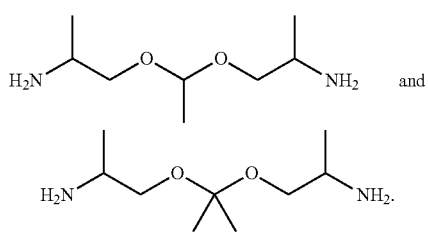

In some embodiments, the compound is selected from the group consisting of

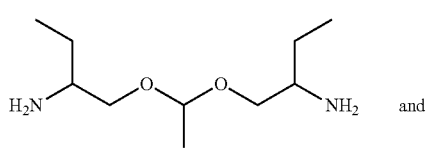

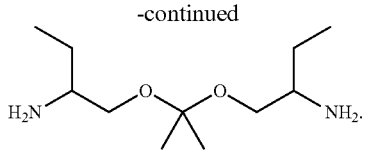

In some embodiments, the compound is selected from the group consisting of

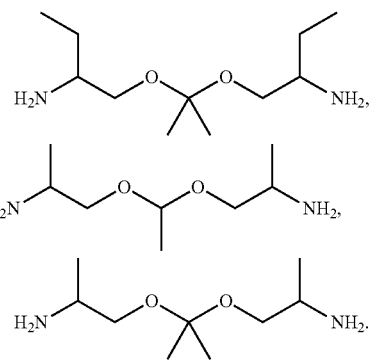

In one aspect, described herein is a salt (e.g., a monoammonium or diammonium salt) of a compound described herein (e.g., a compound of Formula (2-a)). In one embodiment, the salt is a diammonium salt. In one embodiment, the salt is a dihydrochloride salt.

Synthetic Methods

Disclosed herein and elsewhere in the application is a general and economical process for chemical synthesis of the polyamine of Formula (2). For example, the process for chemical synthesis of the polyamine described herein is amenable to scale-up (e.g., >100 MT per annum quantites, through efficient processes (e.g., that eliminate the generation of waste products)). In some exemplary embodiments, the process for chemical synthesis of the polyamine of Formula (2) is suitable for the chemical synthesis of diaminoacetal- and diaminoketal-containing compounds. In some exemplary embodiments, the process for chemical synthesis of the polyamine of Formula (2) facilitates a cost-effective manufacture of acid-degradable materials.

In some exemplary embodiments, the process for chemical synthesis of the polyamine of Formula (2) is suitable for the chemical synthesis of diaminoacetal- and diaminoketal-containing compounds from readily available chemical substances. In some exemplary embodiments, the process for chemical synthesis of the polyamine of Formula (2) is suitable for the chemical synthesis of diaminoacetal- and diaminoketal-containing compounds from a diamino compound salt of Formula (1).

While not wishing to be bound by theory it is believed that the formation of an acetal/ketal from an aldehyde/ketone and an alcohol is an equilibrium process, and the position of the equilibrium can be influenced by either the choice of the starting alcohol or the starting aldehyde/ketone or both. Typically, the equilibrium process is established upon the addition of an acid catalyst to the starting alcohol and aldehyde/ketone. Removal of water from the reaction mixture can be used to drive the equilibrium process toward the acetal/ketal products. Accordingly, a number of factors, including the type acid catalyst, water removal method, and ratio of alcohol to aldehyde/ketone used, can all influence the process of making acetal/ketal containing compounds. The formation of acetal/ketal structures is generally straightforward when simple aliphatic alcohol starting materials are used. However, the formation of acetal/ketal structures becomes less predictable, when more complex alcohol starting materials are used that contain additional chemical functional groups. Additional chemical functionality present in a starting alcohol may result in side reactions with the aldehyde/ketone or aldehyde/ketone equivalent.

The current synthetic strategies in the prior art for the preparation of diaminoacetals, which contain amino functional groups, are not well suited for translation into economical, high-volume, industrial preparation. Amino alcohols such as ethanolamine, 1-amino-2-propanol, and 2-amino-2-methyl-1-propanol are widely used, industrial building blocks and are readily available in large (e.g., truck-load, multi-ton) quantities. They are used as additives for the general chemical industry, and also serve as industrial building blocks for the synthesis of higher value-added chemicals. The direct reaction of an amino alcohol with an aldehyde/ketone would be an ideal approach for the synthesis of diaminoacetals encompassed by Formula (2). However, as is known in the art, and highlighted in Scheme 1 by the reaction of an exemplary amino alcohol such as ethanolamine with acetone or acetaldehyde, an imine formation reaction occurs due to the nucleophilic attack on the carbonyl of the more reactive amino group (as opposed to attack by the hydroxyl group). The formed imine then exists in equilibrium with its corresponding cyclic oxazolidine structure. The formation of oxazolidines and/or imines from amino alcohols is well documented in the art.

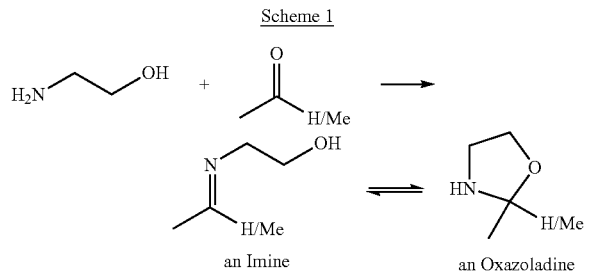

Scheme 1 an Imine      an Oxazoladine

To one skilled in the art, the direct reaction of an amino alcohol with an aldehyde/ketone equivalent would also be an ideal approach for the synthesis of diamino acetals/ketals such as Formula (2). However, as is known in the prior art, and is also highlighted in Scheme 2 by the reaction of an exemplary amino alcohol such as ethanolamine with 2-methoxypropene does not result in the productive formation of the corresponding diaminoacetal. In this case, the amine serves to quench the acid catalyst, effectively inhibiting acetal formation.

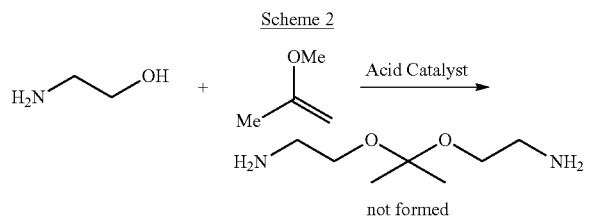

Scheme 2 not formed

Again, not wishing to be bound by theory it is believed that the higher reactivity (or basicity) of the amino group (relative to the hydroxyl group) is the primarily reason for why acetal/ketal formation is not productive for the reaction of amino alcohols with carbonyl compounds or carbonyl equivalents. The use of so-called "protecting groups" to mask the reactivity amino groups in molecules is commonplace in chemical transformations for fine chemical synthesis. Historically, the use of N-protected amino alcohols as, for example, is shown in Scheme 3, is the most commonly employed strategy for the synthesis of diaminoacetals and diaminoacetals in the prior art as, for example, in U.S. Pat. No. 5,191,015, as well as in various other examples in the academic and patent literature. The reported overall yield for this sequence is generally in the range of 50-60%. While this documented procedure is relatively straightforward to perform in the laboratory or fine-chemical scale settings, the process is not ideal for a high-volume industrial process. The method is not economical, as the use of protecting groups increases waste and expense. For instance, the amount of waste generated from cleavage of the phthalimide protecting group in Scheme 3, is greater than the amount of primary amine produced on a weight for weight basis.

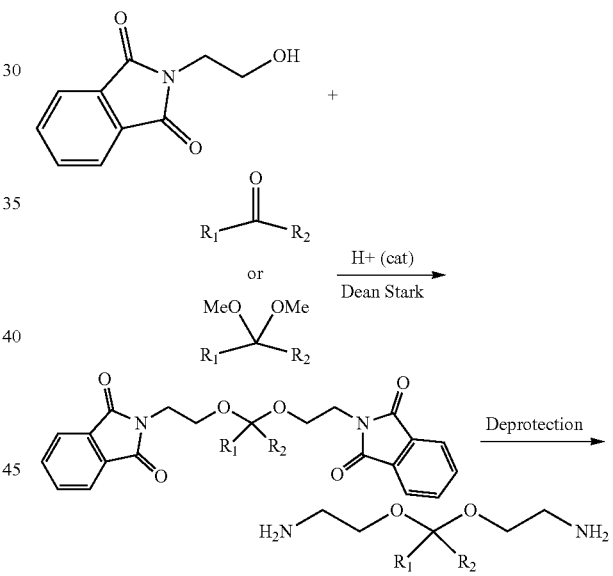

Scheme 3

As disclosed herein, in one aspect, the present invention provides diaminoacetal/ketal salts described herein (e.g., salts represented by Formula (1)). The diaminoacetal/ketal salts of a compound of Formula (2) (e.g., a salt represented by Formula (1)) can be readily prepared in accordance with the methods disclosed herein and then converted into their corresponding free-base forms (e.g. compounds of formula (2)). In one embodiment, the diaminoacetal/ketal salts of Formula (1) is converted into their corresponding free-base by a treatment under a basic condition. In a preferred embodiment, the basic condition is an aqueous basic condition. Specific, but non-limiting examples of an aqueous basic condition are an aqueous metal hydroxide, aqueous metal carbonate, aqueous ammonia, or combination thereof. In one embodiment, the compounds of Formula (2) can be obtained after separation from the aqueous basic layer. In one embodiment, the compounds of Formula (2) can be further purified via distillation after isolation from the aqueous basic layer. In an embodiment, the basic condition is an anhydrous basic condition. A specific, but non-limiting example of an anhydrous basic condition is gaseous ammonia.

Other non-limiting methods of forming diaminoacetal/ketal salts are disclosed in U.S. Application Publication No. 2017/0114002, which is incorporated herein by reference.

It has surprisingly been found that diaminoacetals and ketals of Formula (1) can be synthesized from ammonium salts of amino alcohols as starting materials. In one embodiment, a procedure for converting ammonium salts of amino alcohols into diaminoacetals and ketals of Formula (1) does not require added temperature or a high-pressure condition above and beyond the ambient (ambient temperatures). Amino alcohols are industrial materials that are readily available in bulk quantities. In one embodiment, a procedure for converting ammonium salts of amino alcohols into diaminoacetals and ketals of Formula (1) comprises converting an amino alcohol into its corresponding ammonium salt form via treatment with an acid. In one embodiment, an amino alcohol hydrochloride is obtained by treatment with HCl gas or aqueous HCl (including any further processing). In one embodiment, an amino alcohol hydroacetate is obtained by treatment with acetic acid. The spirit of the invention is not particularly limited by the exact nature of the counterion in the ammonium salt of type Formula (3). The preferred counterions are chloride ion or acetate ion. In a more preferred embodiment, the counterion is chloride ion.

It has surprisingly been found that diaminoacetals and ketals of Formula (1) can be synthesized from ammonium salts of amino alcohols as starting materials. Again, not wishing to be bound by theory, prior to the present disclosure it could have been expected that the reaction of the ammonium salts of type Formula (3) with acetaldehyde/acetone equivalents would have led, instead, to the formation of an oxazolidine salt as shown in Scheme 4.

Scheme 4

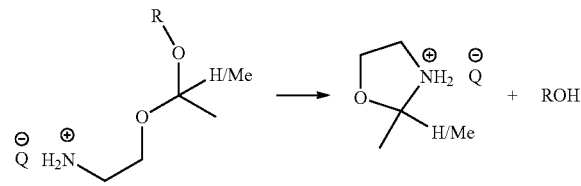

In an aspect, described herein are general and economical processes for the preparation of compounds represented by Formula (2) by the reaction of ammonium salts of amino alcohols with a ketone or aldehyde equivalent. In another aspect, the diammonium salt represented by Formula (1) may be isolated. In still yet another aspect, the diammonium salt may be directly converted to the free-base Formula (2) by the action of a base.

In one embodiment, a process for the chemical synthesis of polyamine of Formula (2) comprises treating a diaminoacetal and/or ketal salt of Formula (1) with a base to produce the polyamine of Formula (2). In one embodiment, the process for the chemical synthesis of the polyamine of Formula (2) comprises treating a diaminoacetal and/or ketal of Formula (1) with a base in a suitable solvent to produce the polyamine of Formula (2).

In another aspect, described herein is a process for preparing a polyamine compound represented by Formula (2) from a polyamine salt represented by Formula (1):

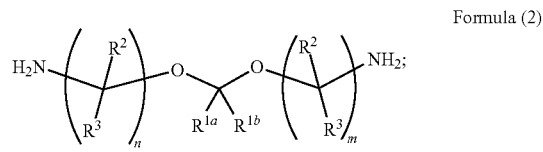

Formula (2)

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2), the process comprising contacting a salt (e.g., a diammonium salt) of the compound of Formula (2) with a base (e.g., sodium hydroxide) to produce the compound of Formula (2).

In some embodiments, $R^{1a}$ is selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2), the process comprising contacting a salt (e.g., a diammonium salt) of the compound of Formula (2) with a base (e.g., sodium hydroxide) to produce the compound of Formula (2).

In some embodiments, $R^{1a}$ is hydrogen and $R^{1b}$ is optionally substituted $C_{1-6}$ alkyl. In some embodiments, $R^{1a}$ is hydrogen and $R^{1b}$ is unsubstituted $C_{1-6}$ alkyl. In some embodiments, each of $R^{1a}$ and $R^{1b}$ is independently selected from unsubstituted $C_{1-6}$ alkyl. In some embodiments, $R^{1b}$ is —$CH_3$. In some embodiments, each occurrence of $R^2$ and $R^3$ is independently selected from unsubstituted $C_{1-6}$ alkyl. In some embodiments, $R^2$ is hydrogen and $R^3$ is unsubstituted $C_{1-6}$ alkyl (e.g., —$CH_3$ or —$CH_2CH_3$). In one embodiment, m is 2. In one embodiment, n is 2. In one embodiment, m is 2 and n is 2. In some embodiments, m and n are the same integer (e.g., m and n are both 2). In some embodiments, the salt of the compound of Formula (2) is present with two equivalents of the base. In some embodiments, the salt of the compound of Formula (2) is present with more than two equivalents of the base.

In some embodiments, the compound of Formula (2) is represented by a compound of Formula (2-a):

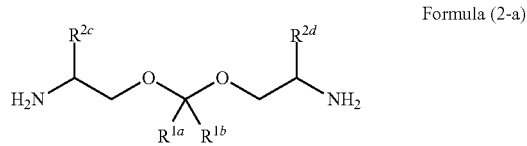

Formula (2-a)

wherein $R^{1a}$ is independently selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); and each of $R^{2c}$ and $R^{2d}$ is independently selected from optionally substituted alkyl (e.g., unsubstituted $C_{1-6}$ alkyl, e.g., unsubstituted $C_{1-6}$ alkyl selected from the group consisting of —$CH_3$ and —$CH_2CH_3$); and salts thereof.

In some embodiments, $R^{1a}$ is hydrogen and $R^{1b}$ is unsubstituted $C_{1-6}$ alkyl. In some embodiments, each of $R^{1a}$ and $R^{1b}$ is independently selected from unsubstituted $C_{1-6}$ alkyl. In some embodiments, each of $R^{2c}$ and $R^{2d}$ is independently selected from unsubstituted $C_{1-6}$ alkyl.

In some embodiments, the compound is selected from the group consisting of the compound represented by the Formula (2-a-I) and the compound represented by Formula (2-a-II):

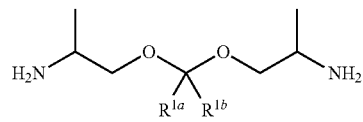

Formula (2-a-I)

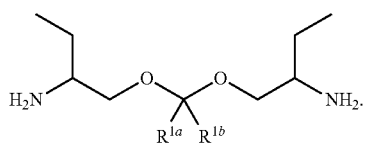

Formula (2-a-II)

In some embodiments, the compound is selected from the group consisting of the compound represented by the Formula (2-a-I):

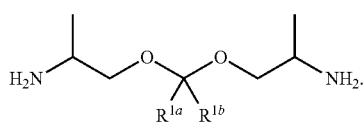

Formula (2-a-I)

In some embodiments, the compound is selected from the group consisting of the compound represented by the compound represented by Formula (2-a-II):

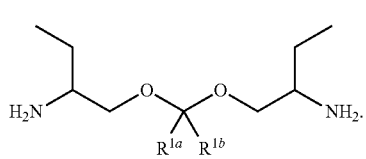

Formula (2-a-II)

In some embodiments, the compound is selected from the group consisting of the compound represented by the Formula (2-a-I-a) and the compound represented by Formula (2-a-II-a):

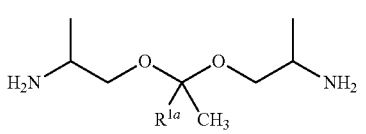

Formula (2-a-I-a)

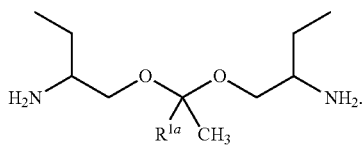

Formula (2-a-II-a)

In some embodiments, the compound is selected from the group consisting of the compound represented by the Formula (2-a-I-a):

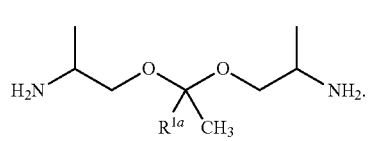

Formula (2-a-I-a)

In some embodiments, the compound is selected from the group consisting of the compound represented by the compound represented by Formula (2-a-II-a):

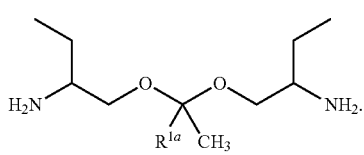

Formula (2-a-II-a)

In some embodiments, the compound is selected from the group consisting of

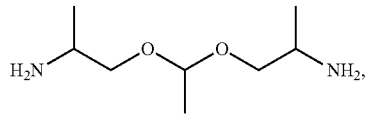

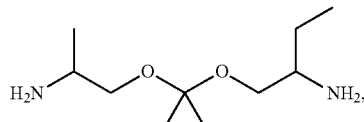

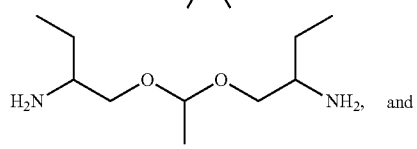

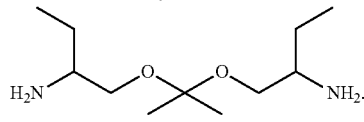

In some embodiments, the compound is selected from the group consisting of

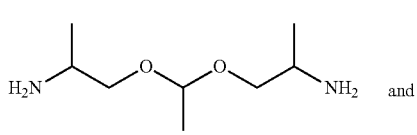

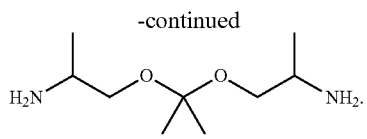

In some embodiments, the compound is selected from the group consisting of

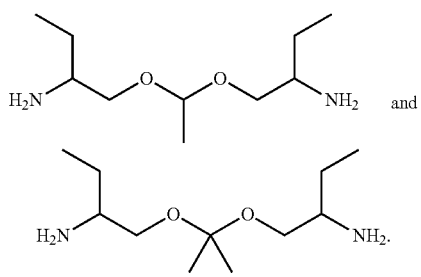

In some embodiments, the compound is selected from the group consisting of

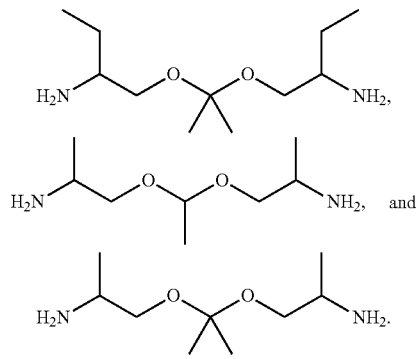

In one embodiment, the salt of the compound of Formula (2) is a salt of Formula (1):

Formula (1)

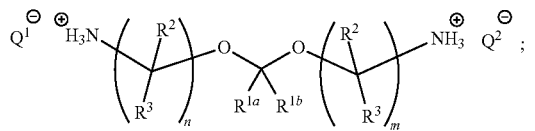

wherein $R^{1a}$ is selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); each occurrence of $R^2$ and $R^3$ is independently selected from the group consisting of hydrogen, optionally substituted alkyl, optionally substituted cycloalkyl, and optionally substituted aryl; $R^2$ and $R^3$ can combine with each other to form optionally substituted cycloalkyl; each m and n is independently an integer ranging from 1 to 20 (e.g., m and n are independently an integer ranging from 1 to 5); and each of $Q^{1\ominus}$ and $Q^{2\ominus}$ is independently a counterion (e.g., each of $Q^{1\ominus}$ and $Q^{2\ominus}$ is independently a counterion selected from the group consist- ing of chloride, bromide, fluoride, iodide, acetate, carboxylate, hydrogen sulfate, nitrate, and phenolate, and sulfonate, e.g., chloride).

In one embodiment, the salt of Formula (1) is a salt selected from the group consisting of a salt of Formula (1-a), a salt of Formula (1-a-I), a salt of Formula (1-a-II), a salt of Formula (1-b), a salt of Formula (1-b-I), a salt of Formula (1-b-I-A), a salt of Formula (1-b-I-B), a salt of Formula (1-b-II), a salt of Formula (1-b-II-A), and a salt of Formula (1-b-II-B) as described herein.

In some embodiments, $Q^{1\ominus}$ and $Q^{2\ominus}$ are the same counterion. In some embodiments, $Q^{1\ominus}$ and $Q^{2\ominus}$ are selected from the group consisting of chloride, bromide, fluoride, and iodide. In some embodiments, $Q^{1\ominus}$ and $Q^{2\ominus}$ are both chloride. In some embodiments, m and n are the same integer (e.g., m and n are both 2).

In yet another aspect, described herein is a process for preparing a salt of a compound represented by Formula (2-1):

Formula (2-1)

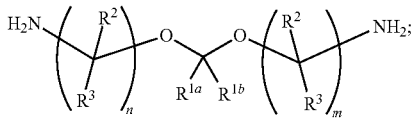

wherein $R^{1a}$ is selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each instance of n is the same integer ranging from 1 to 20, the process comprising the reaction of an aldehyde equivalent or ketone equivalent with a salt of a compound represented by Formula (3):

Formula (3)

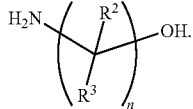

In some embodiments, $R^{1a}$ is hydrogen and $R^{1b}$ is optionally substituted $C_{1-6}$ alkyl. In some embodiments, $R^{1a}$ is hydrogen and $R^{1b}$ is unsubstituted $C_{1-6}$ alkyl. In some embodiments, each of $R^{1a}$ and $R^{1b}$ is independently selected from unsubstituted $C_{1-6}$ alkyl. In some embodiments, $R^{1b}$ is —$CH_3$. In some embodiments, each occurrence of $R^2$ and $R^3$ is independently selected from unsubstituted $C_{1-6}$ alkyl. In some embodiments, $R^2$ is hydrogen and $R^3$ is unsubstituted $C_{1-6}$ alkyl (e.g., —$CH_3$ or —$CH_2CH_3$). In one embodiment, n is an integer ranging from 1 to 5. In one embodiment, n is 2.

In some embodiments, the compound of Formula (2-1) is represented by a compound of Formula (2-a):

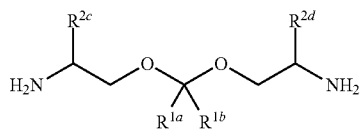
Formula (2-a)

wherein $R^{1a}$ is independently selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); and each of $R^{2c}$ and $R^{2d}$ is independently selected from optionally substituted alkyl (e.g., unsubstituted $C_{1-6}$ alkyl, e.g., unsubstituted $C_{1-6}$ alkyl selected from the group consisting of —$CH_3$ and —$CH_2CH_3$); and salts thereof.

In some embodiments, $R^{1a}$ is hydrogen and $R^{1b}$ is unsubstituted $C_{1-6}$ alkyl. In some embodiments, each of $R^{1a}$ and $R^{1b}$ is independently selected from unsubstituted $C_{1-6}$ alkyl. In some embodiments, each of $R^{2c}$ and $R^{2d}$ is independently selected from unsubstituted $C_{1-6}$ alkyl.

In some embodiments, the compound is selected from the group consisting of the compound represented by the Formula (2-a-I) and the compound represented by Formula (2-a-II):

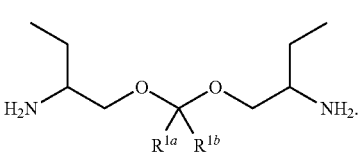
Formula (2-a-I)

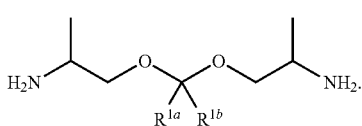
Formula (2-a-II)

In some embodiments, the compound is selected from the group consisting of the compound represented by the Formula (2-a-I):

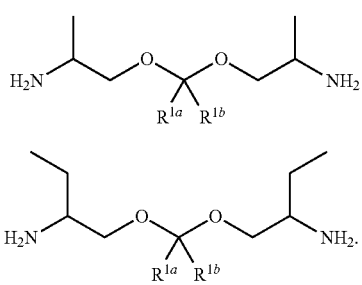
Formula (2-a-I)

In some embodiments, the compound is selected from the group consisting of the compound represented by the compound represented by Formula (2-a-II):

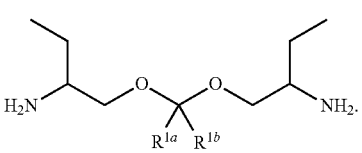
Formula (2-a-II)

In some embodiments, the compound is selected from the group consisting of the compound represented by the Formula (2-a-I-a) and the compound represented by Formula (2-a-II-a):

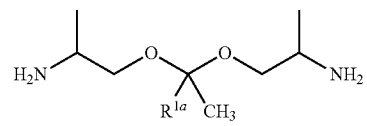
Formula (2-a-I-a)

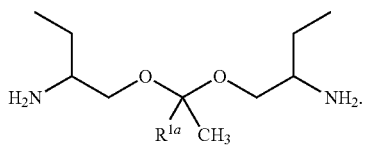
Formula (2-a-II-a)

In some embodiments, the compound is selected from the group consisting of the compound represented by the Formula (2-a-I-a):

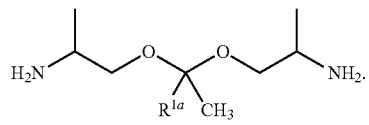
Formula (2-a-I-a)

In some embodiments, the compound is selected from the group consisting of the compound represented by the compound represented by Formula (2-a-II-a):

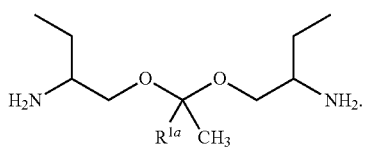
Formula (2-a-II-a)

In some embodiments, the compound is selected from the group consisting of

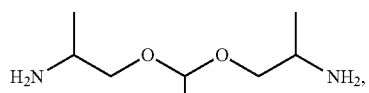

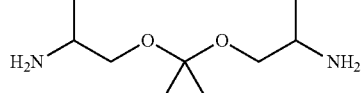

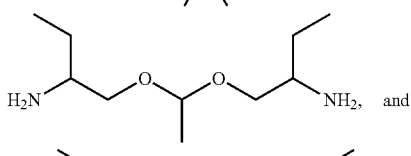
and

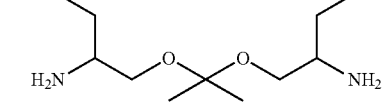

In some embodiments, each n is an integer ranging from 1 to 5. In some embodiments, each n is an integer selected from the group consisting of 1 and 2. In some embodiments, each n is 2.

In some embodiments, the salt of the compound represented by Formula (2-1) is the salt represented by Formula (1-1):

Formula (1-1)

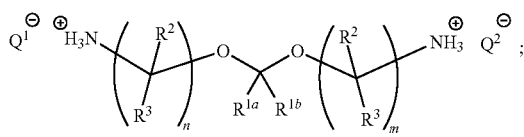

wherein $R^{1a}$ is selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); each occurrence of $R^2$ and $R^3$ is independently selected from the group consisting of hydrogen, optionally substituted alkyl, optionally substituted cycloalkyl, and optionally substituted aryl; or $R^2$ and $R^3$ can combine with each other to form optionally substituted cycloalkyl; each n is an integer ranging from 1 to 20; and each of $Q^{1\ominus}$ and $Q^{2\ominus}$ is independently a counterion (e.g., each of $Q^{1\ominus}$ and $Q^{2\ominus}$ is independently a counterion selected from the group consisting of chloride, bromide, fluoride, iodide, acetate, carboxylate, hydrogen sulfate, nitrate, and phenolate, and sulfonate, e.g., chloride).

In one embodiment, the salt of Formula (1-1) is represented by Formula (1-a):

(1-a)

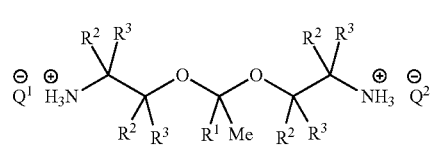

In one embodiment, the salt of Formula (1-1) is represented by Formula (1-a-I):

(1-a-I)

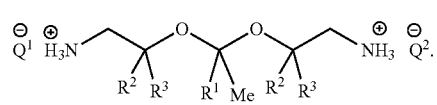

In one embodiment, the salt of Formula (1-1) is represented by Formula (1-a-II):

(1-a-II)

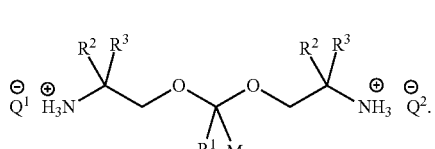

In one embodiment, the salt of Formula (1-1) is represented by Formula (1-b):

(1-b)

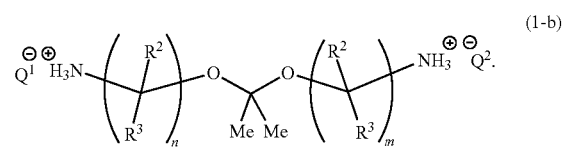

In one embodiment, the salt of Formula (1-1) is represented by Formula (1-b-I):

(1-b-I)

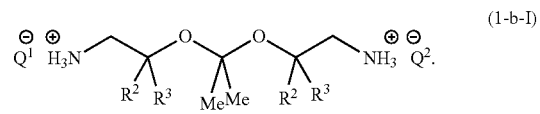

In one embodiment, the salt of Formula (1-1) is represented by Formula (1-b-I-A):

(1-b-I-A)

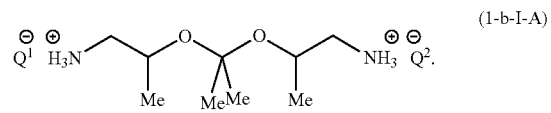

In one embodiment, the salt of Formula (1-1) is represented by Formula (1-b-I-B):

(1-b-I-B)

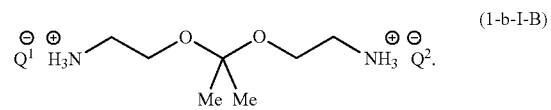

In one embodiment, the salt of Formula (1-1) is represented by Formula (1-b-II):

(1-b-II)

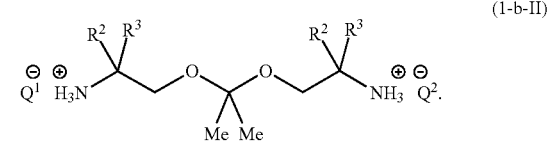

In one embodiment, the salt of Formula (1-1) is represented by Formula (1-b-II-A):

(1-b-II-A)

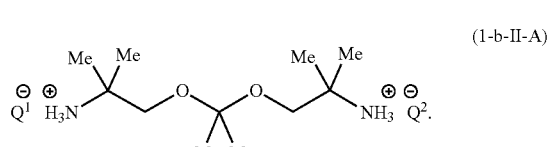

In one embodiment, the salt of Formula (1-1) is represented by Formula (1-b-II-B):

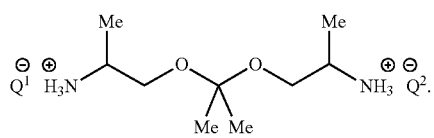
(1-b-II-B)

In some embodiments, $Q^{1\ominus}$ and $Q^{2\ominus}$ are the same counterion. In some embodiments, $Q^{1\ominus}$ and $Q^{2\ominus}$ are selected from the group consisting of chloride, bromide, fluoride, and iodide. In some embodiments, $Q^{1\ominus}$ and $Q^{2\ominus}$ are both acetate. In a preferred embodiment, $Q^{1\ominus}$ and $Q^{2\ominus}$ are both chloride.

In some embodiments, the salt of the compound of Formula (3) is a salt represented by Formula (3-c)

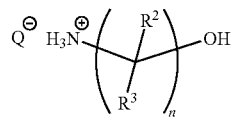
(3-c)

wherein $Q^{\ominus}$ is a suitable counterion (e.g., a counterion selected from the group consisting of chloride, bromide, fluoride, iodide, acetate, carboxylate, hydrogen sulfate, nitrate, and phenolate, and sulfonate, e.g., chloride).

In some embodiments, the salt of Formula (1-1) is a salt of Formula (1-c-1)

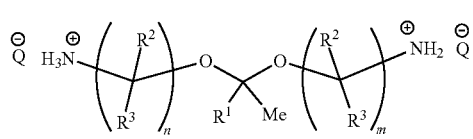
(1-c-1)

wherein $Q^{\ominus}$ is a suitable counterion (e.g., a counterion selected from the group consisting of chloride, bromide, fluoride, iodide, acetate, carboxylate, hydrogen sulfate, nitrate, and phenolate, and sulfonate, e.g., chloride).

In an embodiment, exemplary polyamine salts of Formula (1-1) include, but are not limited to, the following:

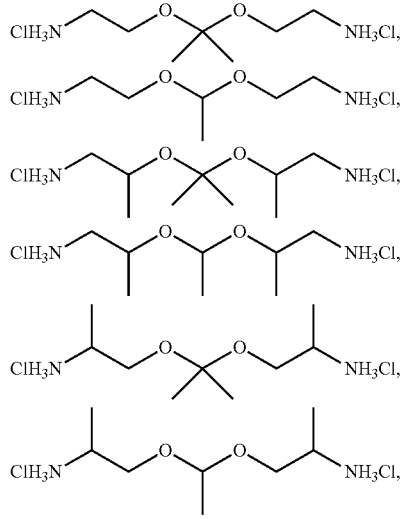

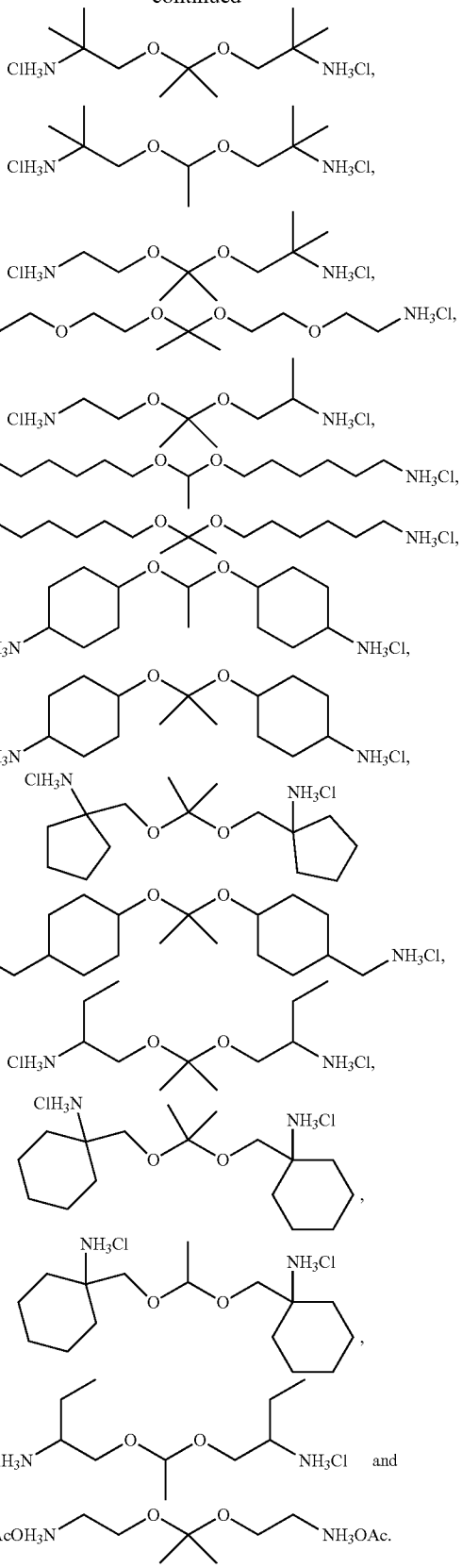

In some embodiments, the salt of Formula (1-1) is selected from the group consisting of:

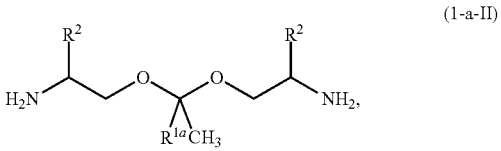

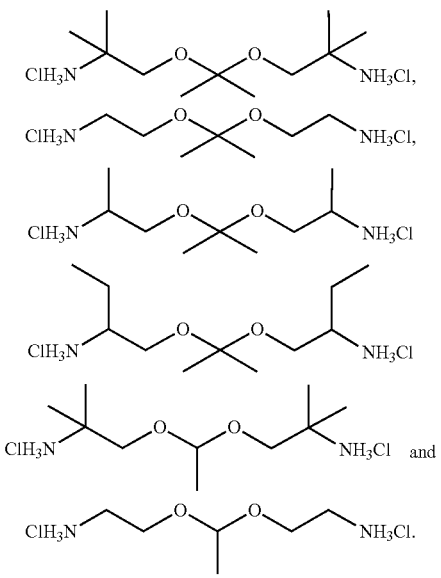

In an embodiment, exemplary amino alcohol salts of the compound of Formula (3) include, but are not limited to, the following:

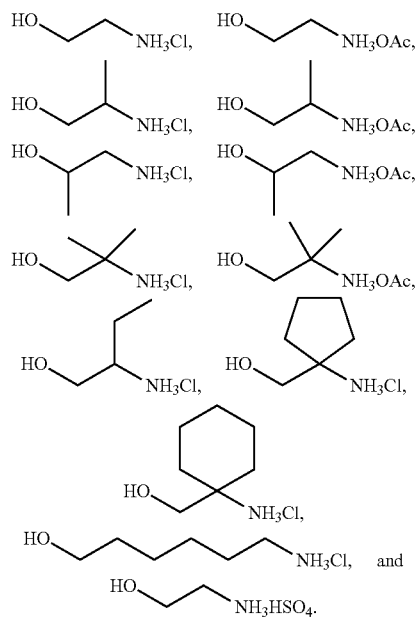

In some embodiments, the salt represented by Formula (1-1) is a salt of the compound represented by Formula (1-a-II):

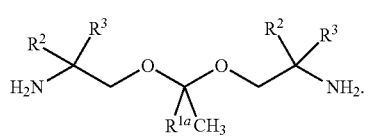

In some embodiments, the salt represented by Formula (1-1) is a salt of the compound represented by Formula (1-a-II):

(1-a-II)

wherein $R^2$ is unsubstituted $C_{1-6}$ alkyl (e.g., unsubstituted $C_{1-6}$ alkyl selected from the group consisting of —$CH_3$ and —$CH_2CH_3$) and $R^{1a}$ is independently selected from the group consisting of hydrogen and —$CH_3$.

In an embodiment, exemplary compounds of Formula (2) include, but are not limited to, the following:

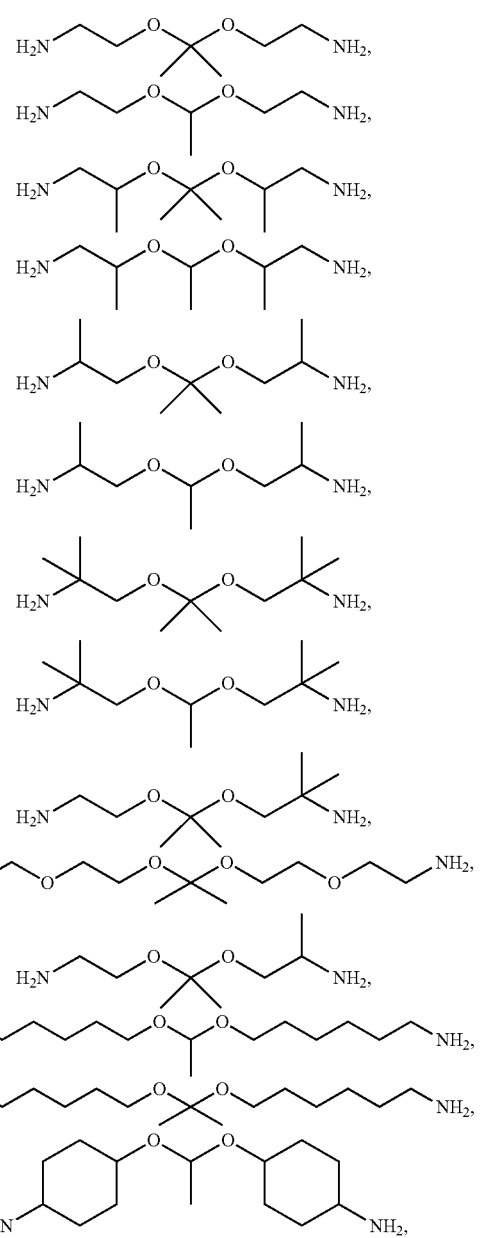

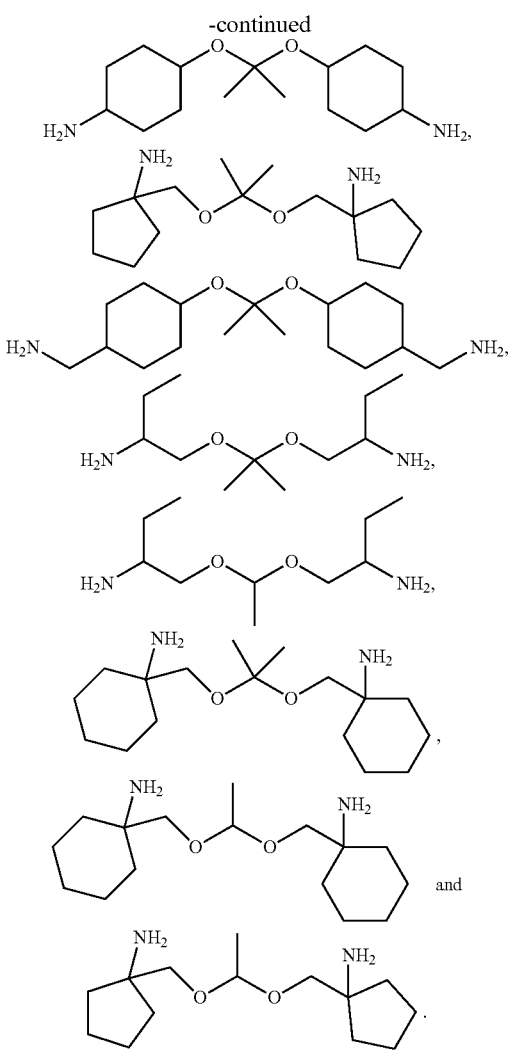

In some embodiments, the ketone equivalent is selected from the group consisting of 2,2-dimethoxypropane; 2-methoxypropene, 2,2-diethoxypropane; and 2-ethoxypropene. In some embodiments, the ketone equivalent is 2,2-dimethoxypropane. In some embodiments, the ketone equivalent is selected from the group consisting of 2-methoxypropene and 2,2-dimethoxypropane. In some embodiments, the ketone equivalent is 2-methoxypropene. In some embodiments, the ketone equivalent is 2,2-dimethoxypropane. In some embodiments, the ketone equivalent is 2,2-diethoxypropane. In some embodiments, the ketone equivalent is 2-ethoxypropene. In some embodiments, the aldehyde equivalent is selected from the group 1,1-dimethoxyethane; methyl vinyl ether, 1,1-diethoxyethane, and ethyl vinyl ether.

In some embodiments, the process further comprises contacting the salt of the compound of Formula (1-1) with a base to produce the compound of Formula (2).

Salts described herein (e.g., a salt of Formula (1-1)) may result from the condensation of 1 molar equivalents of an ammonium salt of amino alcohol of the type Formula (3) with 1 molar equivalent of or an aldehyde- and/or ketone equivalent. In an alternative embodiment, a reaction to produce a salt described herein (e.g., a salt of Formula (1-1)) is carried out in the presence of an excess of aldehyde or ketone equivalent. In an alternative embodiment, a reaction to produce a salt described herein (e.g., a salt of Formula (1-1)) is carried out in the presence of an excess of ammonium salt of amino alcohol of the type Formula (3).

In some embodiments, salts of Formula (3) that react with an aldehyde and/or ketone equivalent have different counterions to produce a salt of the compound of Formula (2) (e.g., a salt of Formula (1-1)). In some embodiments, salts of the compound of Formula (3) that react with an aldehyde and/or ketone equivalent have the same counterions (e.g., a chloride ion) to produce a salt of the compound of Formula (2) (e.g., a salt of Formula (1-1)).

In some embodiments, the reactions to obtain the diammonium salts of Formula (1-1) compounds, the exact molar ratio of the salt of the compound of Formula (3) salt to aldehyde/ketone (or their equivalence—see FIG. 2) used can vary, but one of ordinary skill in the art can select the ratio that balances the yield of the diammonium salt compound of Formula (1-1) versus parameters such as the starting materials costs and the ability to recycle any excess starting materials or reagents. In general, it is preferable to use a molar ratio of the salt of the compound of Formula (3) to aldehyde equivalent and/or ketone equivalent in a ratio of from about 4:1 to 1:4, respectively. In some embodiments, it is preferable to use a molar ratio of the salt of the compound of Formula (3) to aldehyde equivalent and/or ketone equivalent of about 1:1, respectively. In some embodiments, it is most preferable to use a molar ratio of the salt of the compound of Formula (3) to aldehyde/ketone of from about 2:1 to about 1:2, respectively. In some embodiments, it is most preferable to use a molar ratio of the salt of the compound of Formula (3) to aldehyde/ketone equivalent (of from about 2:1 to about 1:1, respectively.

Figure 2:
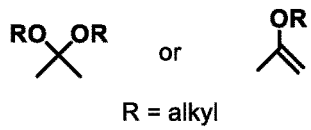
FIG. 2 shows some examples of acetone and acetaldehyde equivalents that can be used in accordance with the methods described herein.
Figure 2:
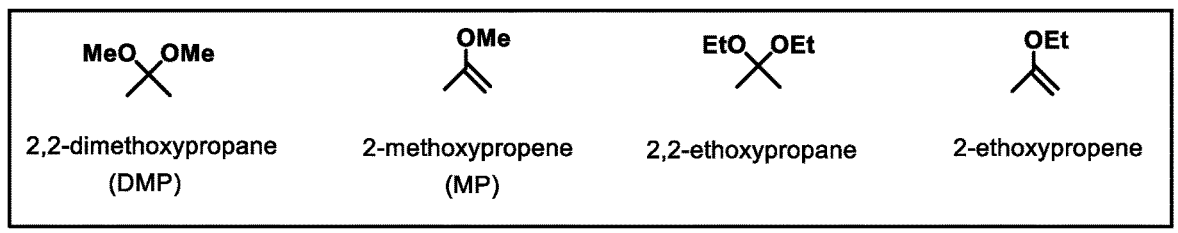
Figure 2:
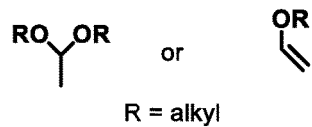
Figure 2:
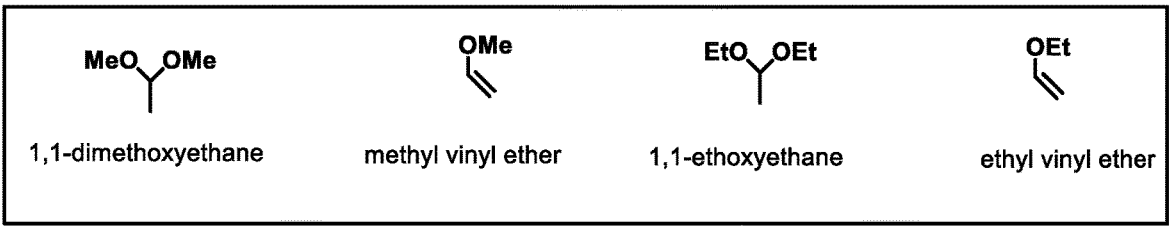
Figure 3:
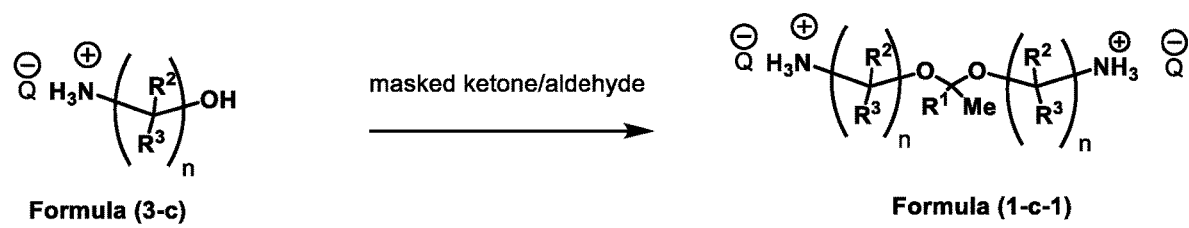
FIG. 3 shows a generic scheme for the conversion to a symmetrical diammonium salt of type Formula (1)
Figure 4:
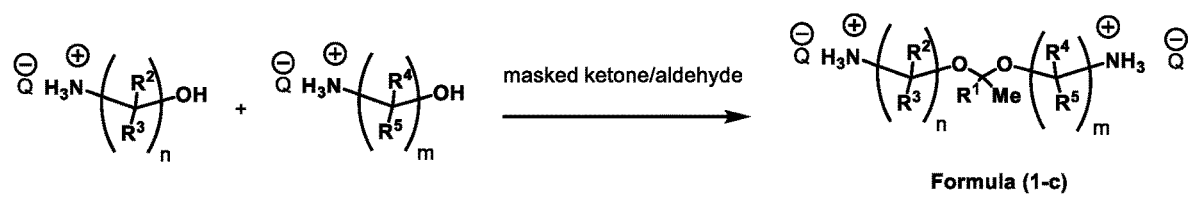
FIG. 4 shows a generic scheme for the conversion to a unsymmetrical diammonium salt of type Formula (1)

In an embodiment, acetal salts of Formula (1-1) are the result from the reaction of the salt of Formula (3) with acetaldehyde or an acetaldehyde equivalent. Specific, but non-limiting, examples of suitable acetaldehyde equivalents in accord with this invention include, methyl vinyl ether, acetaldehyde dimethylacetal, and ethyl vinyl ether (FIG. 2).

In an embodiment, ketal salts of type Formula (1-1) are the result from the reaction of Formula (3) with acetone or an acetone equivalent. Specific, but non-limiting, examples of suitable acetone equivalents in accord with this invention include, 2-methoxypropene, 2,2-dimethoxypropane, and 2,2-diethoxypropene (FIG. 2).

Scheme 5

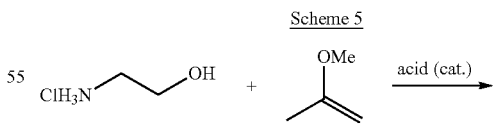

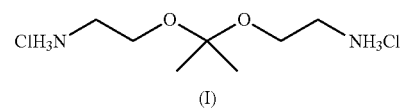

(I)

Scheme 6

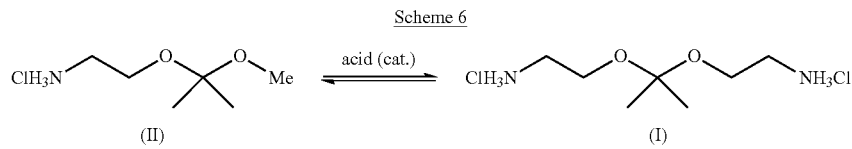

An exemplary reaction embodied by this invention for the formation of a symmetrical diaminoketal depicted in Scheme 5. As depicted in Scheme 6, the formation of (I) presumably occurs via the direct conversion from the mixed ketal compound (II). In an embodiment, the spirit of the invention is not limited to the production of ketals, as acetals may also be formed using the general guidelines disclosed by the present invention. An exemplary reaction embodied by this invention for the formation of a symmetrical acetal depicted in Scheme 7, ethanolamine hydrochloride is reacted with ethyl vinyl ether to give the corresponding dihydrochloride salt (III).

Scheme 7

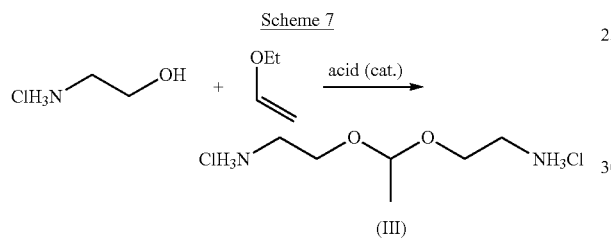

In an embodiment, the spirit of the invention is not particularly limited by the nature of the counter ion of the ammonium salt used of the salts of compounds of type Formula (3). However, hydrochloride salts are particularly preferred for reasons that have to do with reaction efficacy and/or economics.

In some embodiments, the process of making a salt of Formula (2) (e.g., a salt represented by Formula (1)) from a salt of the compound of Formula (3) employs a solvent. Any suitable solvent may be used. In one embodiment, the transformation is carried out in the presence of a solvent selected from the group consisting of acetone, methyl ethyl ketone, methyl tert-butyl ether, toluene, dimethylformamide, dimethylsulfoxide, acetonitrile, dichloromethane, dichlorethane, acetic acid and combinations thereof. In one embodiment, the solvent is recycled. The ideal solvent (and concentration) can be determined by routine optimization by one skilled in the art. In another embodiment the transformation can be carried out without an added solvent.

In some embodiments, the process of making the polyamine of a salt of Formula (2) (e.g., a salt of Formula (1)) from salts of the compound of Formula (3) is carried out at a temperature of from about 0° C. to about 120° C. In some preferred embodiments, the process is carried out a temperature of from about 0° C. to about 50° C. In some more preferred embodiments, the process is carried out a temperature of from about 0° C. to about 35° C.

In some embodiments, the process of making salts of Formula (2) (e.g., a salt of Formula (1)) from salts of the compound of Formula (3) employs an acid catalyst. Any suitable acid catalyst may be used. The acid catalyst may be organic, inorganic, homogenous, heterogeneous or on a solid-support. Specific, but non-limiting, examples of acid catalyst that may be suitable are acetic acid, Amberlyst® resins, acidic zeolites, HCl, $H_2SO_4$, p-toluenesulfonic acid, methanesulfonic acid, chloroacetic acid, pyridinium p-toluenesulfonate, ammonium chloride, Lewis type acids, or other acid.

The chemical synthesis of the polyamino acetal/ketals in accordance with the present invention can be generically represented by the synthetic scheme of scheme 8 below.

Scheme 8

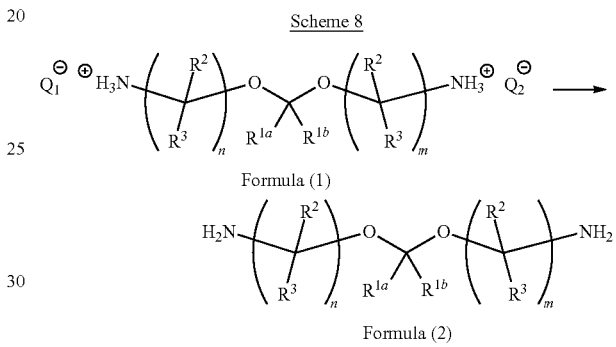

In an embodiment, the transformation is carried out via the subjection of Formula (1) to a basic condition to yield Formula (2). In an embodiment, the conversion of Formula (1) to Formula (2) may be effected in the liquid phase employing a suitable caustic solution. In some embodiments, the process for conversion into a compound of Formula (2) involves treatment of a salt represented by Formula (1) with an aqueous basic solution.

Prior to this disclosure, it was unclear to us whether a salt of the compound of Formula (2) (e.g., a salt represented by Formula (1)) would be capable of converting into Formula (2) without concomitant hydrolysis of the ketal and/or acetal moiety (see FIG. 1). In accord with the present invention, Formula (2) compounds can be prepared with excellent yield via the treatment of Formula (1) with an aqueous basic condition. We have found that the concentration of base is not particularly limiting. For example, treatment of a salt of Formula (2) with a 50% NaOH solution or a more dilute aqueous NaOH solution are both sufficient. The exact nature of the basic condition used is not particularly limiting to the spirit of this invention. In some embodiments, the base may be contained in an aqueous media. In some embodiments the base may be contained in non-aqueous media. There are a wide variety of suitable bases that can be used to effect that transformation of a salt of Formula (2) into Formula (2). Specific, but non-limiting examples, include metal hydroxides, metal carbonates, metal alkoxides, amines, ammonium hydroxide, ammonia, and other industrial bases.

In an embodiment, Formula (2) compounds may be isolated in high purity after treatment via separation from the basic media. In an embodiment, Formula (2) compounds may be further purified via distillation or other methods.

In another aspect, described herein is a process for preparing a salt of a compound represented by Formula (2-1):

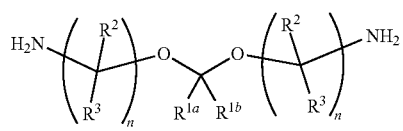

Formula (2-1)

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each instance of n is the same integer ranging from 1 to 20, the process comprising the process comprising reacting a compound of Formula (3) with a compound of Formula (4) in the presence of an acid to produce the salt of a compound of Formula (2-1);

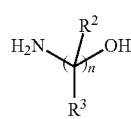

Formula (3)

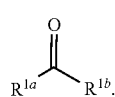

Formula (4)

In one embodiment, said acid is an inorganic acid. In another embodiment, said acid is selected from the group consisting of HCl, HBr, $H_2SO_4$, and combinations thereof. In another embodiment, said acid is selected from the group consisting of HCl, HBr and $H_2SO_4$. In another embodiment, said acid is HCl. In another embodiment, said acid is an organic acid. In another embodiment, said organic acid is selected from the group consisting of p-toluenesulfonic acid, acetic acid, methanesulfonic acid, and combinations thereof. In another embodiment, said organic acid is selected from the group consisting of p-toluenesulfonic acid, acetic acid, and methanesulfonic acid. In one embodiment, Formula (3) and Formula (4) are reacted in the presence of a combination of an inorganic acid and organic acid (e.g., a combination of one type of organic acid and one type of inorganic acid or a combination of more than one type of organic acid and more than one type of inorganic acid). In one embodiment, Formula (3) and Formula (4) are reacted in the presence of more than one type of inorganic acid. In one embodiment, Formula (3) and Formula (4) are reacted in the presence of more than one type of organic acid.

In one embodiment, the compound of Formula (4) is an aldehyde that is provided as a suitably masked formaldehyde equivalent. In one embodiment, the aldehyde is formaldehyde. In one embodiment, the suitably masked formaldehyde equivalent is paraformaldehyde. In one embodiment, the aldehyde is formaldehyde. In another embodiment, the suitably masked formaldehyde equivalent is paraformaldehyde in fine powder form. In one embodiment, the suitably masked formaldehyde equivalent is trioxane. In another embodiment, the ratio of the molar equivalence of the acid to the compound of Formula (3) is greater than 1. In some embodiments, the compound of Formula (3) is pretreated with an acid prior to the reaction with the paraformaldehyde or the any suitably masked formaldehyde equivalent.

In some embodiments, the process further comprises an adding a drying agent to the reaction mixture. In one embodiment, said drying agent is anhydrous magnesium sulfate ($MgSO_4$). In another embodiment, said drying agent is sodium sulfate ($Na_2SO_4$) or potassium sulfate ($K_2SO_4$). In some embodiments, the process is conducted under Dean-Stark type reaction condition to remove any water formed during the reaction. In some embodiments, the process is conducted at temperature ranging from about 0° C. to about 220° C. In some embodiments, the process is conducted at temperature ranging from about 0° C. to about 50° C.

In some embodiments, $R^{1a}$ and $R^{1b}$ are both hydrogen. In some embodiments, $R^{1a}$ is hydrogen and $R^{1b}$ is optionally substituted $C_{1-6}$ alkyl. In some embodiments, $R^{1a}$ is hydrogen and $R^{1b}$ is unsubstituted $C_{1-6}$ alkyl. In some embodiments, $R^{1b}$ is —$CH_3$. In some embodiments, each occurrence of $R^2$ and $R^3$ is independently selected from unsubstituted $C_{1-6}$ alkyl. In some embodiments, $R^2$ is hydrogen and $R^3$ is unsubstituted $C_{1-6}$ alkyl (e.g., —$CH_3$ or —$CH_2CH_3$). In one embodiment, n is an integer ranging from 1 to 5. In one embodiment, n is 2. In some embodiments, when $R^{1a}$, $R^{1b}$, $R^2$, and $R^3$ are not hydrogen, then n is not 2.

In some embodiments, the compound of Formula (2-1) is represented by a compound of Formula (2-a):

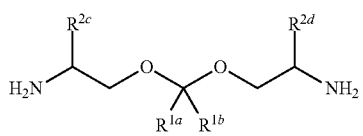

Formula (2-a)

wherein each of $R^{2c}$ and $R^{2d}$ is independently selected from optionally substituted alkyl (e.g., unsubstituted $C_{1-6}$ alkyl, e.g., unsubstituted $C_{1-6}$ alkyl selected from the group consisting of —$CH_3$ and —$CH_2CH_3$); and salts thereof.

In some embodiments, $R^{1a}$ is hydrogen and $R^{1b}$ is unsubstituted $C_{1-6}$ alkyl. In some embodiments, each of $R^{2c}$ and $R^{2d}$ is independently selected from unsubstituted $C_{1-6}$ alkyl.

In some embodiments, the compound is selected from the group consisting of the compound represented by the Formula (2-a-I) and the compound represented by Formula (2-a-II):

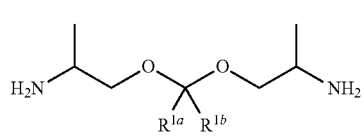

Formula (2-a-I)

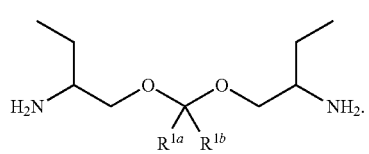

Formula (2-a-II)

In some embodiments, the compound is selected from the group consisting of the compound represented by the Formula (2-a-I):

Formula (2-a-I)

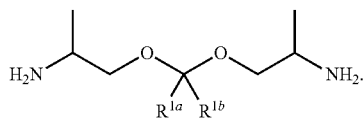

In some embodiments, the compound is selected from the group consisting of the compound represented by the compound represented by Formula (2-a-II):

Formula (2-a-II)

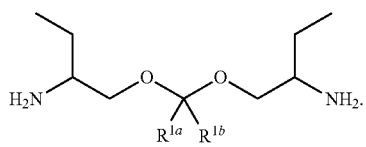

In some embodiments, the compound is selected from the group consisting of the compound represented by the Formula (2-a-I-a) and the compound represented by Formula (2-a-II-a):

Formula (2-a-I-a)

Formula (2-a-II-a)

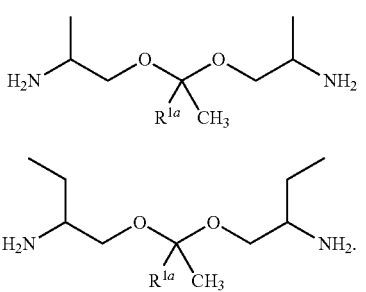

In some embodiments, the compound is selected from the group consisting of the compound represented by the Formula (2-a-I-a):

Formula (2-a-I-a)

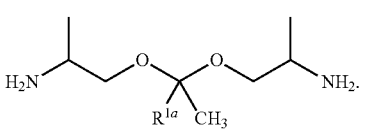

In some embodiments, the compound is selected from the group consisting of the compound represented by the compound represented by Formula (2-a-II-a):

Formula (2-a-II-a)

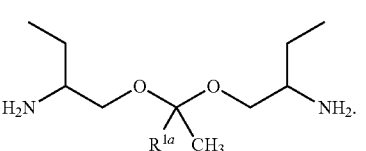

In some embodiments, each n is an integer ranging from 1 to 5. In some embodiments, each n is an integer selected from the group consisting of 1 and 2. In some embodiments, each n is 2.

In some embodiments, the salt of the compound represented by Formula (2-1) is the salt represented by Formula (1-1):

Formula (1-1)

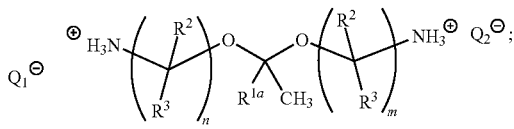

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; each m and n is independently an integer ranging from 1 to 20 (e.g., m and n is independently an integer ranging from 1 to 5); and each of $Q^{1\ominus}$ and $Q^{2\ominus}$ is independently a counterion (e.g., each of $Q^{1\ominus}$ and $Q^{2\ominus}$ is independently a counterion selected from the group consisting of chloride, bromide, fluoride, iodide, acetate, carboxylate, hydrogen sulfate, nitrate, and phenolate, and sulfonate, e.g., chloride).

In some embodiments, $R^{1a}$ and $R^{1b}$ are both hydrogen. In some embodiments, $R^{1a}$ is hydrogen and $R^{1b}$ is optionally substituted $C_{1-6}$ alkyl. In some embodiments, $R^{1a}$ is hydrogen and $R^{1b}$ is unsubstituted $C_{1-6}$ alkyl. In some embodiments, each of $R^{1a}$ and $R^{1b}$ is independently selected from unsubstituted $C_{1-6}$ alkyl. In some embodiments, $R^{1b}$ is —$CH_3$. In some embodiments, each occurrence of $R^2$ and $R^3$ is independently selected from unsubstituted $C_{1-6}$ alkyl. In some embodiments, $R^2$ is hydrogen and $R^3$ is unsubstituted $C_{1-6}$ alkyl (e.g., —$CH_3$ or —$CH_2CH_3$). In one embodiment, m is 2. In one embodiment, n is 2. In one embodiment, m is 2 and n is 2. In some embodiments, m and n are the same integer (e.g., m and n are both 2).

In one embodiment, the salt of Formula (1-1) is represented by Formula (1-a):

(1-a)

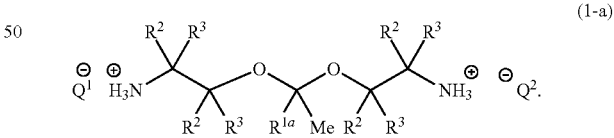

In one embodiment, the salt of Formula (1-1) is represented by Formula (1-a-I):

(1-a-I)

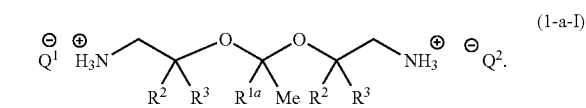

In one embodiment, the salt of Formula (1-1) is represented by Formula (1-a-II):

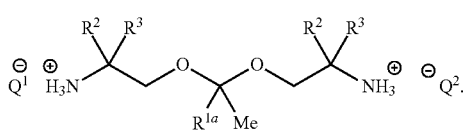

(1-a-II)

In some embodiments, $Q^{1\ominus}$ and $Q^{2\ominus}$ are the same counterion. In some embodiments, $Q^{1\ominus}$ and $Q^{2\ominus}$ are selected from the group consisting of chloride, bromide, fluoride, and iodide. In some embodiments, $Q^{1\ominus}$ and $Q^{2\ominus}$ are both acetate. In a preferred embodiment, $Q^{1\ominus}$ and $Q^{2\ominus}$ are both chloride.

In some embodiments, the salt represented by Formula (1-1) is a salt of Formula (1-d-1)

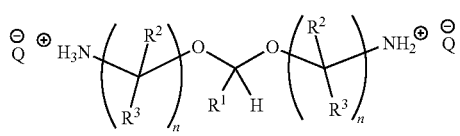

(1-d-1)

wherein $Q^{\ominus}$ is a suitable counterion (e.g., a counterion selected from the group consisting of chloride, bromide, fluoride, iodide, acetate, carboxylate, hydrogen sulfate, nitrate, and phenolate, and sulfonate, e.g., chloride).

In an embodiment, the salt represented by Formula (1-1) is selected from the group consisting of:

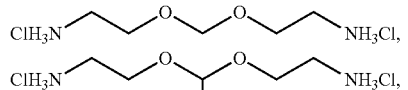

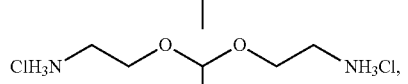

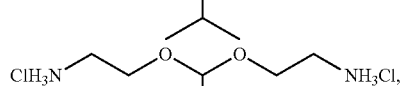

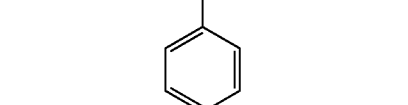

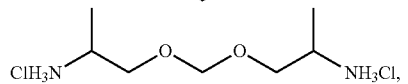

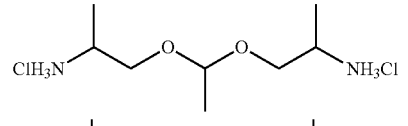

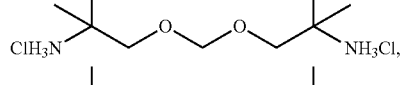

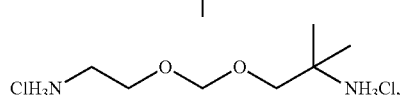

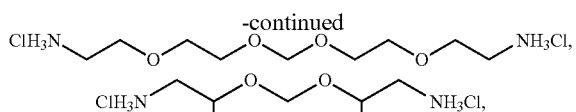

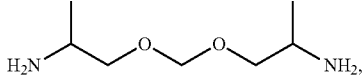

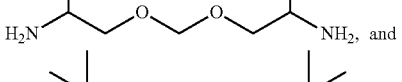

In some embodiments, the compound of Formula (2) is selected from the group consisting of:

In an embodiment, exemplary compounds of Formula (2) include, but are not limited to, the following:

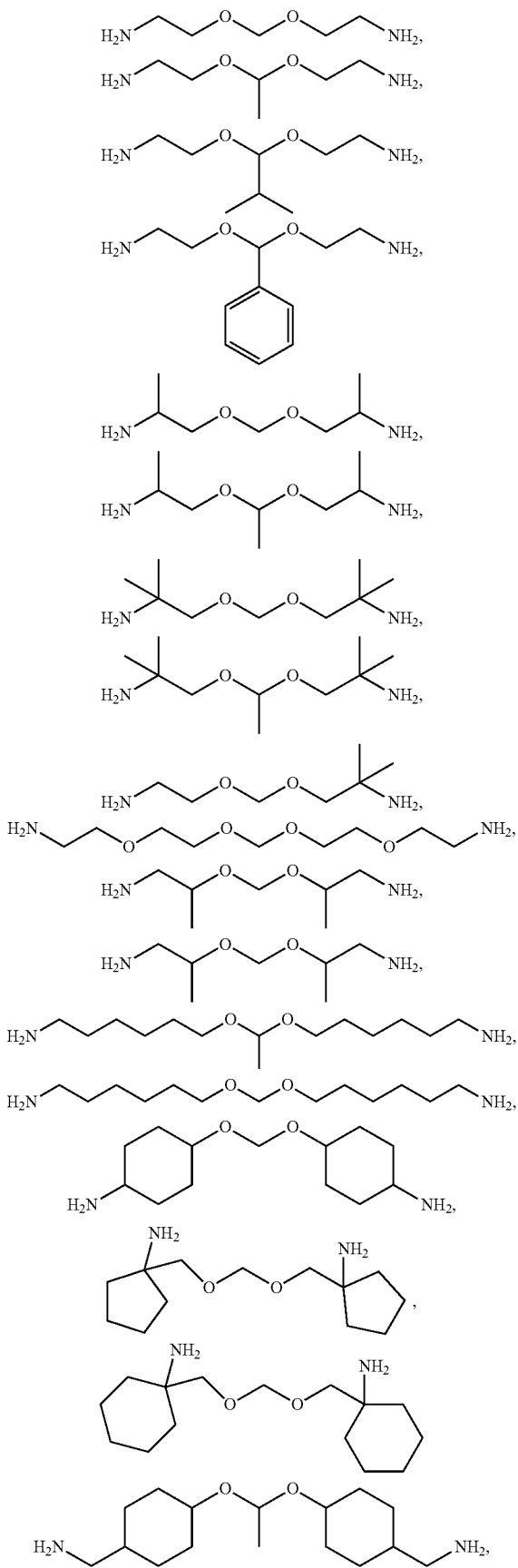
-continued
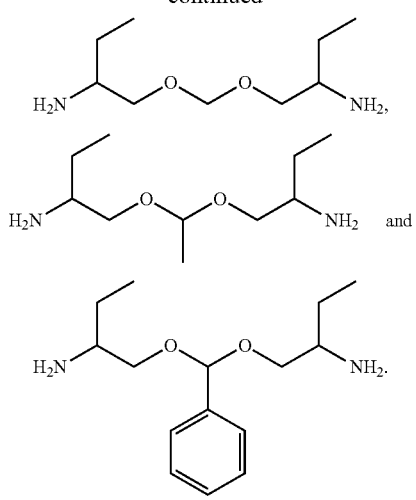
In an embodiment, exemplary salts of the compound represented by Formula (3) include, but are not limited to, the following:
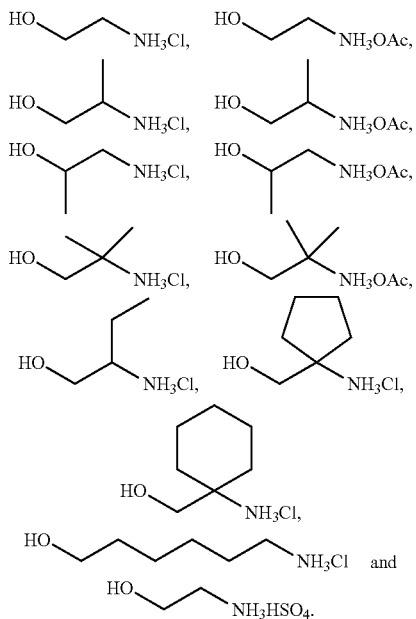
In some embodiments, the salt represented by Formula (1-1) is a salt of the compound represented by Formula (1-a-II):
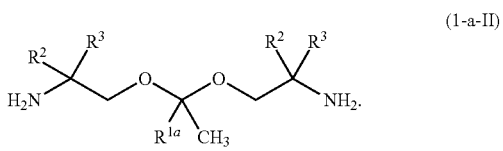
(1-a-II)
In some embodiments, the salt represented by Formula (1-1) is a salt of the compound represented by Formula (1-a-II):

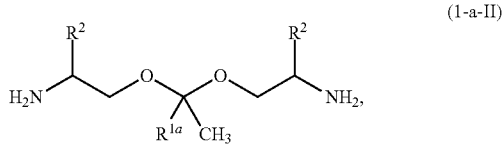

(1-a-II)

wherein $R^2$ is unsubstituted $C_{1-6}$ alkyl (e.g., unsubstituted $C_{1-6}$ alkyl selected from the group consisting of —$CH_3$ and —$CH_2CH_3$) and $R^{1a}$ is independently selected from the group consisting of hydrogen and —$CH_3$.

Epoxy Compositions

Epoxy or epoxy compositions generally refers to the cured end product of epoxy resins. Epoxy curing involves at least two phenomena, polymerization and cross-linking. Each phenomenon is complex, and the two are often in competition during the overall curing process. Curing may be achieved by reacting epoxy with itself (e.g., homopolymerization) or with curing agents, e.g., curatives or hardeners (e.g., aliphatic polyamines, e.g., aliphatic polyamines of the Formula (2)). During the initial stage of curing, polymerization is typically favored as a result of the reactivity of curing agents (i.e., the reactive functional groups present in the curing agents). For example, where a curing agent has terminal primary amines or secondary amine groups, reactions of the primary amine groups with epoxy groups of epoxy resin will be favored over reactions of the secondary amine groups (e.g., with epoxy groups). Therefore, generally polymerization of curing agents and epoxy resins precedes cross-linking reactions between them (e.g., reactions with the secondary amine groups). Such a polymerization reaction typically involves an addition reaction between an epoxide and an amine group, and thus would tend to follow a rate equation for addition polymerization. The molecular weight of the growing polymer increases (e.g., until the molecular weight approaches infinity), so that almost all monomers are connected by at least one bond and a polymeric network is formed. At this point, sometimes called the "gel point", the polymer possesses high molecular weight and few cross-links, and thus behaves much like a very high molecular weight thermoplastic (e.g., a plastic that is pliable or moldable above a specific temperature and returns to the solid state on cooling).

The second stage of the curing process, cross-linking, becomes the dominant phenomenon once the gel point is reached due to the lack of free monomers (i.e., monomer of the curing agent(s)). The cross-linking reaction involves interchain bonding of intrachain reactive sites, between either intrachain epoxides or secondary amine sites. Although cross-linking is a different phenomenon than polymerization, the rate of chemical conversion of the epoxide groups is unaffected (e.g., is similar or unchanged relative to the polymerization rate) in most epoxy systems. The cross-linking reactions produce a growing network and reduce the mobility of the chain segments. The growth of the network results in mechanical and thermal stabilization of the structure, resulting in increasing modulus and glass transition ($T_g$).

At a certain high degree of cross-linking, the increasing molecular weight of the structure exceeds the molecular weight which is thermodynamically stable as a rubber, and the material transforms into a glass, a process referred to as vitrification. In a glassy state, the mobility of reactants is severely restricted, reducing the rate of the reaction to a diffusion-controlled reaction, which is much slower. Further conversion is still possible, however, the rate is much slower since the process relies on diffusion rather than mobility to bring the reactants together. When the cross-linking reaction exhausts all the reactive sites available, the resulting structure is hard (i.e., has a high modulus) and insoluble due to a high degree of interchain bonding.

Since chemicals react in definite proportions, theoretically, a given weight of an epoxy resin will react with a given "equivalent," or "stoichiometric," amount of polyamine curing agent to form a polymeric product if the conditions are such that the reaction can proceed to completion. Therefore in general, with epoxies or epoxy resins, when the curing agent contains primary amine groups, as is the case with some embodiments of the aliphatic polyamine cross-linking agent described herein, the first step of the two stage curing process discussed above involves the oxirane ring in the epoxy resin undergoing a ring opening reaction with an amine group of the aliphatic polyamine cross-linking agent to produce an aminoalcohol product. In the second step of the two-stage curing process the aminoalcohol product, a reacted amine nitrogen (i.e., as a "secondary" amine group), can react with yet another epoxy (i.e., oxirane ring) to form a higher molecular weight or branched polymer (e.g., to form a higher molecular weight and branched polymer). Thus, most or all of the —$NH_2$, or the primary amine groups of the aliphatic polyamine cross-linking agent, will require two oxirane groups for complete reaction.

When the reactants are, for example, polyamine curing agent H-(1-1), described herein below, and a typical bisphenol A-type epoxy resin, such as BPADGE, each molecule of polyamine curing agent H-(1-1), with its two primary amine groups, may react with four oxirane groups as shown in Scheme A below. Notably, epoxy resins such as BPADGE can, e.g., polymerize by homopolymerization and therefore not be present in the monomeric form depicted.

Scheme A

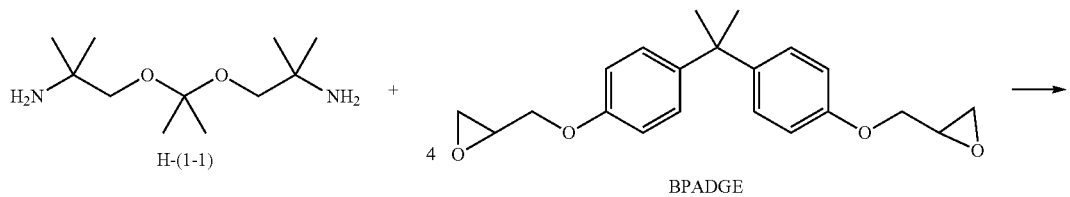

-continued

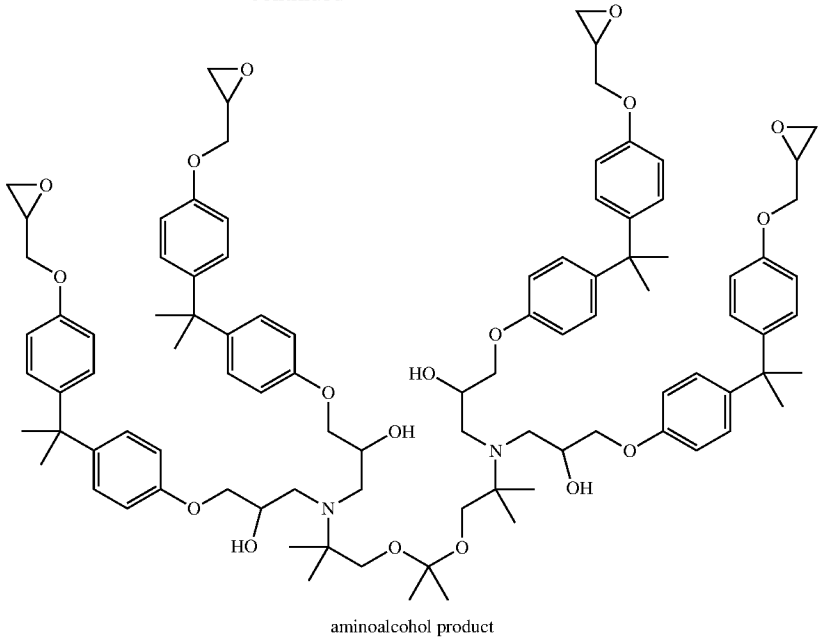

aminoalcohol product

Therefore, in regard to chemical balancing, the optimum, proportions of reactants relative to epoxy systems can be obtained at least in of two ways: (1) by calculating the quantities involved from the chemical "equivalent" weights of all the reactants, or (2) by determining the balance empirically. Generally, epoxy resin's epoxide equivalent weight (EEW) is defined by the following equation 1 (eq. 1):

$$\text{Epoxy resin epoxide } eq. \text{ wt. (or } EEW) = \frac{\left(\begin{array}{c}\text{MW of}\\ \text{epoxy resin}\end{array}\right)}{\left(\begin{array}{c}\text{no. of epoxides}\\ \text{in the epoxy resin}\end{array}\right)} \quad (eq.1)$$

wherein MW of epoxy resin represents molecular weight of the epoxy resin.

In some embodiments, an epoxy resin composition described herein includes an epoxy resin comprising a blend of a bisphenol-based epoxy resin having an epoxide equivalent weight (EEW) in the range of 160 to 220. In some embodiments, an epoxy resin composition described herein includes an epoxy resin comprising a bisphenol-based epoxy resin having an EEW in the range of 400 to 1500. In some embodiments, an epoxy resin composition described herein includes an epoxy resin comprising a blend of a first bisphenol-based epoxy resin having an epoxide equivalent weight (EEW) in the range of 160 to 220 and a second bisphenol-based epoxy resin having an EEW in the range of 400 to 1500.

Analogously, amine hydrogen equivalent weight is defined by the following equation 2 (eq.2):

$$\text{Amine hydrogen } eq. \text{ wt. (or } AEW) = \frac{(\text{MW of amine})}{\left(\begin{array}{c}\text{no. of active}\\ \text{hydrogens}\end{array}\right)} \quad (eq.2)$$

wherein MW of amine represents molecular weight of the amine.

The stoichiometric ratio of an amine hardener to use with epoxy resin having a known or calculable epoxide equivalent weight EEW can be calculated using the following equation 3 (eq.3):

$$\text{stoichiometric ratio of amine} = \frac{(\text{Amine } H \text{ } eq. \text{ wt} \times 100)}{(\text{Expoxide } eq. \text{ wt. of resin})} \quad (eq.3)$$

As an example, EEW of bisphenol A diglycidyl ether (BPADGE), AEW of H-(1-1), and stoichiometric ratio of H-(1-1) are calculated as follows.

H-(1-1) has a molecular weight of 218.34 atomic mass units (amu) and four active hydrogens. According to eq. 2, AEW of H-(1-1) equals 54.585 (or 218.34÷4). BPADGE has a molecular weight of 340.41 amu and two epoxides. According to eq.1, EEW of BPADGE equals 170.205 (or 340.41÷2). According to eq.3, the stoichiometric ratio of H-(1-1) to use with BPADGE equals 32.07 (or [54.585× 100]÷170.205). In other words, if one wishes to use a stoichiometric amount of H-(1-1) with BPADGE, one would need 32.07 parts H-(1-1) by wt. per 100 parts resin (BPADGE) or 32.07 g of H-(1-1) for every 100 g of BPADGE used.

Generally, the empirical (i.e., experimental) method of chemical balancing is preferred, e.g., at least because actual working conditions are used. However, in some embodiments, calculating the quantities involved from the chemical "equivalent" weights of all the reactants is used. Differences in the two calculating methods may arise from factors such as steric hindrance or catalytic effects. However, such differences may be easily corrected empirically through adjustments to the experimental conditions.

As described herein, "working time" refers to the time it takes to for a 100 gram mass (or greater than a 100 gram mass) of epoxy resin composition to reach a solidified state at room temperature, wherein "room temperature" is defined by the temperature range of 20-27° C. "Gel-time," as described herein, is used interchangeably with "working time".

The working time of a epoxy resin composition begins when a hardener (e.g., an aliphatic polyamine cross-linking agent, e.g., an aliphatic polyamine cross-linking agent of the Formula (1)) and an epoxy resin (e.g., BPADGE) are added together or are first present together in the polymer composition. In some embodiments, the working time of the epoxy resin composition end when cross-linking of the curing agents and epoxy resins begins. In some embodiments, the working time for the epoxy resin composition described herein is less than 2 hours. In some embodiments the pot-life of the epoxy resin composition described herein is at least 4 hours (e.g., 4, 6, 8, 12, 14, 16, 18, 20, 24 hours). In some embodiments, the working time for the epoxy resin composition described herein is longer in duration (e.g., 1, 2, 3, 4, 5, 6, 7, 8, 9, 10, 11, 12, 13, 14, 15 or more times longer in duration) than the working time for an epoxy resin composition comprising a conventional hardener (e.g., an aliphatic polyamine). Working time may also refer to the duration of time for which a composition (e.g., a composition as described herein, e.g., a composition comprising an epoxy resin and an aliphatic polyamine cross-linking agent (e.g., an aliphatic polyamine cross-linking agent of Formula (2)) retains a viscosity in which the composition can be e.g., easily poured, or can be used e.g., to impregnate a fiber such as, fiber glass or carbon fiber. In some embodiments, the working time is the time for which a composition (e.g., a composition as described herein, e.g., a composition comprising an epoxy resin and an aliphatic polyamine cross-linking agent (e.g., an aliphatic polyamine cross-linking agent of Formula (2)) retains a viscosity of less than 10,000 cP. For filament winding, for example, a working time of at least 3 hours, and preferably greater than 1 day is desired. Certain epoxy resin composition manufacturing or processing described herein exhibit long working time or long pot-life of at least 3 hours (e.g., at least 4, 6, 8, 12, 14, 16, 18, 20, 24 hours). In some embodiments, the epoxy resin compositions exhibit working time of from about 2 hours to about 12 hours. In some embodiments, the epoxy resin compositions exhibit working time of from about 4 hours to about 24 hours.

The epoxy compositions described herein can be cured at between 0° C. to about 220° C. In some embodiments, the epoxy compositions can be cured at between 20° C. to 50° C. In some embodiments, the epoxy compositions can be cured at between 50° C. to 120° C. In some embodiments, the epoxy compositions can be cured at least at 30° C., at least at 50° C., at least at 60° C., at least at 70° C., at least at 80° C., at least at 90° C., at least at 100° C., at least at 120° C., at least at 150° C., at least at 170° C., at least at 200° C., at least at 220° C. In some embodiments, the epoxy compositions can be cured at least at 80° C.

Certain epoxy compositions described herein should also find use in pipe repair applications (e.g., trenchless pipe repair applications). For example, the Cured in Place Pipe [CIPP] process involves inverting a resin saturated felt tube made of fiberglass and other materials inside a damaged pipe, and then curing the resin system, effectively making a pipe with in a pipe seal. Polyester thermosets, are commonly used for CIPP. For regulatory reasons, there is increasing momentum in the industry to switch a way from polyester resin systems, e.g., to epoxy-based systems. However, there has been a lack of suitable epoxy curatives that can be used for these purposes. The typical requirements of a resin systems are both that 1) the resin impregnated felt has to be easily pliable, e.g., for at last 24 hours after impregnation; and 2) the resin should cure in less than 24 hours (preferably less than 12 hours), e.g., at the temperature of the hot water passing through the pipe (usually <80° C.). Conventional epoxy curatives systems are not well suitable for either or both requirements. Curing with the amines described by Formula (2), enable epoxy resin compositions that satisfy both requirements.

For prepreg composite manufacturing, epoxy compositions must exhibit very slow cure rate at ambient temperature and/or cure to an intermediately stable state to be acceptable. This can be achieved with curing agents that cure the resin following a sequential course that entails, first, linear polymerization and subsequent cross-linking of the linear polymers. The polyamine cross-linking agents described herein are ideally suited for prepreg composite manufacturing. Certain epoxy resin compositions described herein provide long working time that keeps the epoxy resin composition flowing or manipulable for a long time and thus allows the epoxy composition to be shaped and processed over the long working time desired, e.g., for prepreg composite manufacturing. In some embodiments, the compositions are used for manufacturing prepreg composites.

Certain epoxy compositions described herein undergo (1) minimal reaction at ambient temperatures, but suitable reactivity at elevated temperatures; and (2) a slight linear polymerization which yields a glassy solid or metastable state, effectively slowing further linear polymerization or cross-linking, until reinitiated with introduction of energy, including heat at a higher temperature, to advance polymerization and cross-linking of the epoxy resin composition. One skilled in the art would recognize an epoxy composition in this metastable state as a "B-stage." One skilled in the art should also recognize that it is not typical for aliphatic polyamines curing agents to lead to B-staging epoxy resin compositions. As described herein, out-life or time in B-stage or B-state, are defined as the time to reach a partially cross-linked state (e.g., the time to reach a state wherein the epoxy composition is not capable of flowing, e.g., upon addition of elevated temperature; the time to reach a state wherein the epoxy composition is transformed to a partially or fully cross-linked polymer matrix).

In a typical prepreg process, an intermediate composite is formed, for example by coating a woven fiber (e.g. fiberglass, carbon fiber, aramid fiber, or natural fiber) with an epoxy resin and hardener mixture; and cured to an intermediate state. At the desired time, such prepreg sheets can be stacked and molded into a composite part by reestablishing the ductility of the epoxy composition and reinitiating the curing (e.g., by compression and heating). In order to make a good multilayered composite, the epoxy composition must be capable of "flow" for proper interpenetration between layers. The length of time a prepreg sheet can spend at room temperature before partial cross-linking of the epoxy resin composition occurs is known as the prepreg's "out-life." Premature cross-linking of a prepreg sheet effectively renders it useless for the manufacture of multilayered composites. After manufacturing, a prepreg sheet or roll may be stored in the freezer to extend its out-life prior to shipping or composite manufacture.

Generally, for an epoxy resin composition to be suitable for prepreg composite manufacturing, it should minimally have B-stage state of at least 1 week at room temperature. Ideally, the composition would have a B-stage state of infinity, however, in practice, commercial epoxy composition used in prepreg applications typically have a B-stage specification of months to 1 year.

Prepregs using certain epoxy resin compositions described herein exhibit an out-life of at least 1 week at room temperature. In some embodiments, prepregs using the epoxy resin compositions exhibit an out-life of from about 1 week to about 2 weeks at room temperature. In some embodiments, prepregs using the epoxy resin compositions exhibit an out-life of from about 2 weeks to about 4 weeks at room temperature. In some embodiments, prepregs using the epoxy resin compositions exhibit an out-life of from about 1 day, 2 days, 3 days, 4 days, 5 days, 6 days or more. In some embodiments, prepregs using the epoxy resin compositions exhibit an out-life of from about 1 week, 2 weeks, 3 weeks, 4 weeks, or more. In some embodiments, prepregs using the epoxy resin compositions exhibit an out-life of from about 1 month, 2 months, 3 months, 4 months, 5 months, 6 months, 7 months, 8 months, 9 months, 10 months, 11 months, or more. In some embodiments, prepregs using the epoxy resin compositions exhibit an out-life of from about 1 year, 2 years, or more.

For composites applications that utilize prepreg and/or filament winding and/or pultrusion processes, there are effectively three types of curing agents that are widely used with epoxy resins: 1) DICY type curing agents (often in combination with imidazole accelerators); 2) anhydride-based curing agents (often in combination with imidazole accelerators); and 3) aromatic amines such as MDA and DDS. The use of aromatic amines, in particular MDA, has fallen out of favor in the industry due to toxicity concerns. Although aliphatic-type amines represent the most widely used epoxy curatives in the epoxy industry as a whole, they are generally unsuitable for use in filament winding and prepreg applications. The primary reason for this is that aliphatic amines are too reactive (i.e., do not have long enough working times). Certain aliphatic polyamine cross-linking agents described herein (i.e., those where the nitrogen group is sterically hindered by alkyl group substitution) react more slowly with epoxy resins than the aliphatic amines that are not sterically hindered. Accordingly, epoxy resin compositions described herein, containing these less reactive aliphatic polyamine cross-linking agents are much more suitable for filament winding and prepreg applications.

The epoxy compositions described herein (e.g., an epoxy resin composition comprising the product of an epoxy resin and an aliphatic polyamine (e.g., as a cross-linking agent), wherein the aliphatic polyamine comprises (e.g., consists of or consists essentially of) a compound having the structure of Formula (2) as described herein) are also contemplated as useful in the infusion of large composite structures, such as the creation of fiberglass composite windmill blades. Typically, the commercially used epoxy systems for windmill blades have moderately working times on the order of a few hours, but not days. It is important for the epoxy composition to have a working time that is sufficiently long enough such that the composition does not cure, prematurely, during the infusion process. On the other hand, it is desirable for the setting time to not be too long after the infusion has be completed. Further, as most epoxy-based wind blades are post-cured in mold on the order of 80° C., then it is important for the epoxy composition to develop a high degree of cure (i.e., >98% cure) under this curing temperatures. Certain epoxy compositions described under this invention are suitable to meet such processing requirements, with the added benefit of providing the feature of recyclability. An epoxy resin composition for the construction of a recyclable windmill blade is a specific, but non-limiting, example of an application.

Unlike thermoplastics, thermosetting plastics such as epoxies, are generally not recyclable. Cross-linking reactions that occur with conventional epoxies are essentially irreversible, which means the cross-linked materials cannot be re-melted and re-shaped without decomposition. Moreover, the cross-linked materials cannot be readily dissolved in most solvents. As a result, epoxy-based materials such as fiber reinforced epoxies or epoxy-based composite materials are generally not amenable to standard recycling practices. Thus, the epoxy matrix and fibers cannot be readily separated, and/or recovered. As result, such composite materials have historically been incinerated, land-filled, or ground and repurposed as filler material.

However, epoxy resin compositions described herein are recyclable even when cross-linked. The reason for this is that cross-linking groups in the cross-linked epoxy polymers are cleavable by chemical means, e.g., including reaction with acid. The aliphatic polyamine cross-linking agent described herein have at least one acetal or ketal group that is susceptible to cleavage under acidic conditions. Cross-linked epoxy polymers described herein contain these acid cleavable groups and therefore can be degraded for recycling purposes by treatment with acid.

The intractability of cured epoxy resins, stemming primarily, from their highly cross-linked network that is characteristic of known cured epoxy resins is not an issue with the cured epoxy resins described herein. Cured epoxy resins described herein can result in composites with links in a three-dimensional network structure which can be cleaved under controlled conditions, resulting in disassembly of the three-dimensional network structure into smaller, more soluble molecules and/or polymeric fragments. Degradable cured composites provide a way to recover any articles, reinforcement materials and the like that were in cured composite material. Replacing conventionally used epoxy hardeners with cleavable cross-linking agents described herein effectively solves the present recycling problem associated with epoxy based composites and materials.

The aliphatic polyamine cross-linking agents described herein, react more slowly than conventional aliphatic-type polyamine cross-linking agents). As such epoxy resin compositions containing the aliphatic polyamine cross-linking agents described herein possess long working times, e.g., of sufficient length to make them useful in many applications, including filament winding applications. Epoxy resin compositions described herein provide reworkable epoxy compositions and thus composites made therefrom can be more easily degraded and recycled. Because of the slow reactivity of the aliphatic polyamine cross-linking agents described herein, epoxy resin compositions containing them exhibit an intermediate stable state that allows the epoxy composition to be processed over much longer working time than is possible with conventional hardeners. Accordingly, epoxy resin compositions described herein are useful for prepreg composite molding. Such composites can be recycled because the prepreg composites are reworkable by methods described herein.

Terms such as "hardenable" or "curable" are used interchangeably herein, and are intended to refer to any material that can be stably stored for an extended period of time in a first, malleable or flexible form without loss of flexibility, and transitionable into a second, hardened form after application of an initiating energy thereto. These terms are not intended to be limited to any specific mechanism of hardening. As will be understood by those of skill in the art, a variety of hardening mechanisms can be utilized, depending upon material selection, including for example, curing that is initiated by ultraviolet radiation, visible light, infrared radiation, radio frequency radiation, x-ray radiation, gamma radiation or other wavelength of electromagnetic energy, catalyst-initiated polymerization, thermally-initiated polymerization, electrically-initiated polymerization, mechanically-initiated polymerization, curing initiated by electron beam radiation and the like.

In one embodiment, the epoxy resin composition comprises an epoxy resin that has an average of at least two epoxide groups per molecule. In one embodiment, the epoxy resin composition comprises a diepoxide resin. In one embodiment, the epoxy resin composition comprises a diepoxide resin selected from a group consisting of glycidyl ether epoxy resin, glycidyl ester epoxy resin, glycidyl amine epoxy resin, alicyclic epoxy resin, aliphatic epoxy resin, phenolic epoxy resin, and combinations thereof.

In some embodiments, the epoxy resin composition comprises an epoxy resin that comprises a blend of epoxy resins. In one embodiment, the epoxy resin composition comprises a blend of bisphenol-based epoxy resins. In one embodiment, the epoxy resin composition comprises a blend of bisphenol-based epoxy resins having an epoxide equivalent weight (EEW) in the range of 160 to 220. In one embodiment, the epoxy resin composition comprises a blend of bisphenol-based epoxy resins having an epoxide equivalent weight (EEW) in the range of 400 to 1500.

In some embodiments, epoxy resins may be blended, filled, or modified with reactive and non-reactive components. In one such embodiment, it may be necessary to adjust the concentration of the curing polyamine agent to cure only the portion of the mix that is reactive; e.g., the resins and any reactive diluent present. In one embodiment, this may be done by calculating the epoxide equivalent weight (EEW) of the total mix and then applying equation 2 (eq. 2) to determine the amount of curing polyamine agent to add to 100 parts of the epoxy resin composition. As an example, an EEW of a blended epoxy resins may be calculated according to equation 4 (eq. 4).

$$EEW \text{ of mix} = \frac{(\text{Total Wt. of Mix})}{\left( \begin{array}{c} Wta/(EEWa) + Wtb/(EEWb) + \ldots + \\ Wtn/(EEWn) \end{array} \right)} \quad (\text{eq. 4})$$

wherein Total Wt. of Mix represents the molecular weight of the total mix and includes all materials, both reactive and non-reactive; a, b, . . . and n, are only the materials reactive with the aliphatic polyamine cross-linking agent and are characterized by an epoxy ring; EEWa represents EEW of reactive material a; EEWb represents EEW of reactive material b; and EEWn represents EEW of reactive material n.

In some embodiments, the epoxy resin composition includes a blended epoxy resin, and an aliphatic polyamine cross-linking agent of Formula (2) as can be calculated by eq.3 above. In one embodiment, epoxy resin blend includes a mixture of a diglycidyl ether of a bisphenol, especially bisphenol A, having an EEW of 150-195, typically 180-190, and a diglycidyl ether of a bisphenol, especially bisphenol A having an EEW of 400-1500, preferably 1200-1400. In one embodiment, epoxy resin blend includes a mixture of a diglycidyl ether of a bisphenol, especially bisphenol A, having an EEW of 150-195, typically 180-190, a diglycidyl ether of a bisphenol, especially bisphenol A, having an EEW of 400-1500, preferably 1200-1400, and an epoxy phenolic novolac resin with a functionality of 2.2 to 4, typically 3.6 or above, having an EEW of 170-190, preferably 174-180. In one embodiment, epoxy resin blend includes a mixture of a diglycidyl ether of a bisphenol, especially bisphenol A, having an EEW of 150-195, typically 176, a diglycidyl ether of a bisphenol, typically bisphenol A, having an EEW of 400-1500, preferably 1200-1400, and a tetra-functional epoxy having an EEW of 117-134.

Various bisphenol-based epoxy resin blends may be used to make compositions described herein. In particular, in one embodiment the bisphenol-based epoxy resin is a blend based on the reaction products of epichlorohydrin and bisphenol A ("BPA") and/or bisphenol F ("BPF"). Bisphenol-based epoxy resins that are useful include, but are not limited to, bisphenol A diglycidyl ether, ("BPADGE") and its oligomers and bisphenol F diglycidyl ether, ("BPFDGE") and its oligomers. FIG. 2 depicts various epoxy resins including generic structures for BPADGE and BPFDGE and their oligomers. In some embodiments, molecular weight of preferred oligomers of BPADGE and BPFDGE can be up to approximately 6000 g/mol. In one embodiment, the bisphenol-based epoxy resin based on bisphenol A has a molecular weight in the range of about 340 to about 6000 g/mol. In one embodiment, the bisphenol-based epoxy resin based on bisphenol F has a molecular weight in the range of about 310 to about 6000 g/mol. In some embodiments, the bisphenol-based epoxy resins have a molecular weight between and optionally including any two of the following values: 298, 300, 310, 340, 400, 600, 800, 1000, 1200, 1500, 1800, 2100, 2400, 2700, 3000, 3300, 3600, 3900, 4200, 4500, 4800, 5100, 5400, and 6000. Since the bisphenol-based epoxy resins have 2 epoxy groups per oligomer, the bisphenol-based epoxy resins have an epoxide equivalent weight (EEW) that is generally about half of the molecular weight of the oligomer. In one embodiment, the bisphenol-based epoxy resin is present from about 40 to about 95 wt %, based on the combined weight of the bisphenol-based epoxy resin, amine curing agent, and multi-epoxy reactive diluents. In another embodiment, the bisphenol-based epoxy resin is present from about 40 to about 95 wt %, based on the combined weight of the components in the curable composition. In some embodiments, the bisphenol-based epoxy resin is present in an amount between and optionally including any two of the following values: 40, 45, 50, 55, 60, 65, 70, 75, 80, 85, 90, and 95 wt %, based on the combined weight of the components in the curable composition. In some embodiments, the bisphenol-based epoxy resin is contains bromine atoms. Brominated epoxy resins are useful for applications that require flame retardancy. Specific, but non-limiting, examples of commercially available bisphenol A diglycidyl ether epoxy resins are Insulcast 503/504 BLK; Insulcast 504 Clear; Insulcast 125; Insulcast 333; Insulcast 136; and Insulcast 502, available (from ITW Polymer Technologies (Glenview, Ill., U.S.A.); Epon resins from Hexion Specialty Chemicals, Inc., now Momentive Specialty Chemicals, Inc., part of Momentive Performance Materials Holdings, Inc., (Columbus, Ohio, U.S.A.); D.E.R™ resins from The DOW Chemical Company. Specific, but non-limiting, examples of commercially available include bisphenol F diglycidyl ether epoxy resins, including Araldite® GY285, Araldite® GY281, and Araldite® PY302-2 from Huntsman International, LLC (Salt Lake City, Utah, USA). Mixtures of bisphenol-based epoxy resins can be used in the curable composition described herein.

In some embodiments, reactive diluents are added to a bisphenol-based epoxy resin. In some embodiments, monofunctional epoxides are further blended with the bisphenol-based epoxy resin. Reactive diluents are common additives for influencing the viscosity of resin systems. Reactive diluents can also improve the surface qualities of coatings and composites. Specific, but non-limiting, examples of suitable reactive diluents include, $C_{12}$-$C_{14}$ alkyl glycidylethers, o-cresyl glycidylether, and butyl-glycidylether.

In some embodiments, a less than stoichiometric amount of polyamine curing agent of Formula (2) is used in the epoxy resin composition described herein. In one embodiment, the epoxy resin composition contains 2% of the stoichiometric amount of polyamine curing agent of Formula (2). In one embodiment, the epoxy resin composition contains the aliphatic polyamine cross-linking agent of Formula (2) in a percentage selected from the group consisting of about 4%, about 6%, about 8%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, and about 98% of the stoichiometric amount of polyamine curing agent of Formula (2).

For a given epoxy composition and application, the ideal amount of the reworkable curing agent of Formula (2) may be less than, or greater than the calculated stoichiometric amount. One skilled in the art can recognize that deviations from the stoichiometric amount may lead to changes in the processing properties of the epoxy composition or of the final properties of the cured thermoset. Such changes may, or may not, be desired depending on the manufacturing method employed or the end application for the epoxy-based material. The preferable amount can be easily determined by one skilled in the art via routine experimentation, but is preferably in the range of about 60% to about 140% of the stoichiometric amount, and more preferably from about 90% to about 110%.

The curable resin composition described herein is obtained by uniformly mixing the above-described components. A process of obtaining a cured product described herein from the curable resin composition described in detail above may be in accordance with a commonly used curing process of a curable resin composition. The heating temperature condition can be appropriately selected in accordance with the type of curing agent used in the combination or application. In an example of the process, the curable resin composition described herein is heated in the temperature range of about 20° C. to 250° C. Examples of the form of the cured product include a laminate, a composite, a cast product, an adhesive layer, a coating film, and a film.

Pultrusion or filament winding generally consists of forming a resin mixture bath, immersion of a glass, carbon, aramid, natural, unnatural fiber (of from about 1-3 mm in diameter) in the mixture for a period of time (typically for about 1 sec), winding the wet fiber on a mandrel, and, subsequently, further curing with heat the composite, which includes the resin mixture and the fiber. The gel times of certain resin mixtures described herein are sufficiently long for filament winding purposes. The working time for stoichiometric mixtures of DGEBA with Hardeners (e.g., hardeners as described herein (e.g., certain hardeners of Formula (2))), are greater than 4 hrs. At room temperature (i.e. 20-25° C.), the resin mixtures become a hard brittle solid in greater than 4.

Unless otherwise stated herein, the terms "hardener", "curing agent", "cross-linking agent" are used interchangeable as synonyms of "cross-linking agent". As is the case with thermosetting epoxies, the processing properties (e.g. curing time, peak exotherm, mixed viscosity, etc.) and cured resin physical properties ($T_g$, tensile strength, flexibility modulus, chemical resistance, conductivity, adhesion, color, impact strength, etc.) can be modified by the addition of auxiliary materials to the base epoxy resin/hardener composition for the purposes of preparation of epoxy compositions tailored for a given application. Accordingly, in some embodiments, the epoxy resin composition further includes an auxiliary material selected from the group consisting of flame retardant, accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, gloss additive and combinations thereof.

In some embodiments, amino molecules that contain 2, or less than 2, active N—H hydrogens can be used in combination with the aliphatic polyamine cross-linking agents of Formula (2). Primary monoamines, bis(secondary) diamine molecules, and other molecules that contain only two active N—H hydrogens are suitable for use in the epoxy resin composition described herein, e.g., as chain extenders. In one embodiment, the chain extenders are used to adjust the cross-link density of a cured epoxy resin in accordance with exemplary embodiments described herein. By adding these chain extenders to the polyamine curing agents of Formula (2), one can decrease the cross-linking density in the final cured epoxy matrix. Specific, but non-limiting, examples of chain-extendable molecules that contain only two active N—H hydrogens include monoethanolamine, 3-aminopropanol, 2-aminobutanol, 2-aminopropanol, 2-amino-2-methyl-1-propanol [AMP], benzylamine, aniline, p-anisidine, butylamine, piperazine, and N,N'-dimethylethylenediamine, tert-butylamine, and, sec-butylamine. In an embodiment, the epoxy resin composition described herein includes at least one amine chain extender in an amount ranging from about 0% to about 98% relative to weight of the aliphatic polyamine cross-linking agent of Formula (2).

One skilled in the art will recognize that the incorporation of chain extenders will alter the processing and mechanical properties of the epoxy composition from that of an epoxy composition that only uses Formula (2) as the reactive curing agent. In one embodiment, the use of a chain extender, e.g., because its combination with polyamine curing agent of Formula (2) does not interfere with the recyclability properties of the epoxy composition. In particular, the use of amino alcohols also has the effect of a cure accelerator.

In an aspect, described herein is an epoxy resin composition comprising the product of an epoxy resin and an aliphatic polyamine (e.g., as a cross-linking agent), wherein the aliphatic polyamine comprises (e.g., consists of or consists essentially of) a compound having the structure of Formula (2):

Formula (2)

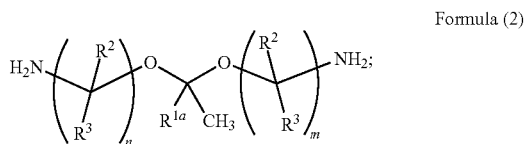

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2).

In some embodiments, $R^{1a}$ is selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2).

In some embodiments, $R^{1a}$ is hydrogen and $R^{1b}$ is unsubstituted $C_{1-6}$ alkyl. In some embodiments, each of $R^{1a}$ and $R^{1b}$ is independently selected from unsubstituted $C_{1-6}$ alkyl. In some embodiments, $R^{1b}$ is —$CH_3$. In some embodiments, $R^2$ is unsubstituted $C_{1-6}$ alkyl and $R^3$ is hydrogen. In one embodiment, m is 2. In one embodiment, n is 2. In one embodiment, m is 2 and n is 2. In some embodiments, m and n are the same integer (e.g., m and n are both 2).

In some embodiments, the compound of Formula (2) is represented by a compound of Formula (2-a):

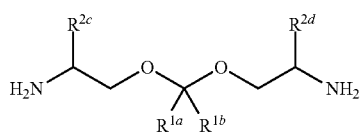

Formula (2-a)

wherein $R^{1a}$ is independently selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); and each of $R^{2c}$ and $R^{2d}$ is independently selected from optionally substituted alkyl (e.g., unsubstituted $C_{1-6}$ alkyl, e.g., unsubstituted $C_{1-6}$ alkyl selected from the group consisting of —$CH_3$ and —$CH_2CH_3$); and salts thereof.

In some embodiments, $R^{1a}$ is hydrogen and $R^{1b}$ is unsubstituted $C_{1-6}$ alkyl.

In some embodiments, each of $R^{1a}$ and $R^{1b}$ is independently selected from unsubstituted $C_{1-6}$ alkyl. In some embodiments, each of $R^{2c}$ and $R^{2d}$ is independently selected from unsubstituted $C_{1-6}$ alkyl.

In some embodiments, the compound is selected from the group consisting of the compound represented by the Formula (2-a-I) and the compound represented by Formula (2-a-II):

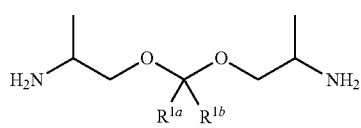

Formula (2-a-I)

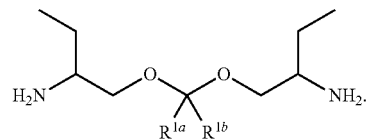

Formula (2-a-II)

In some embodiments, the compound is selected from the group consisting of the compound represented by the Formula (2-a-I):

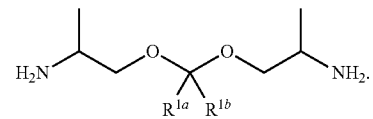

Formula (2-a-I)

In some embodiments, the compound is selected from the group consisting of the compound represented by the compound represented by Formula (2-a-II):

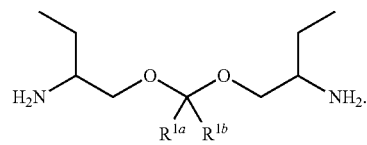

Formula (2-a-II)

In some embodiments, the compound is selected from the group consisting of the compound represented by the Formula (2-a-I-a) and the compound represented by Formula (2-a-II-a):

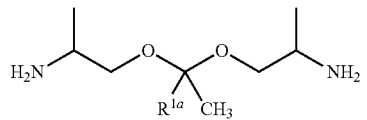

Formula (2-a-I-a)

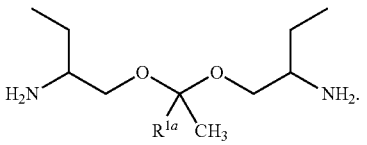

Formula (2-a-II-a)

In some embodiments, the compound is selected from the group consisting of the compound represented by the Formula (2-a-I-a):

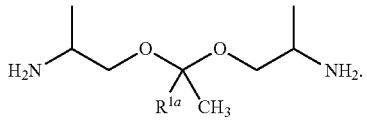

Formula (2-a-I-a)

In some embodiments, the compound is selected from the group consisting of the compound represented by the compound represented by Formula (2-a-II-a):

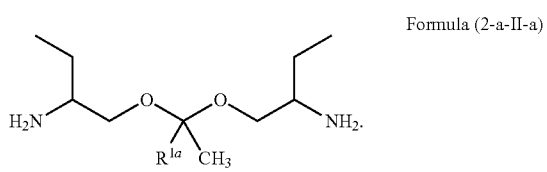

Formula (2-a-II-a)

In some embodiments, the compound is selected from the group consisting of

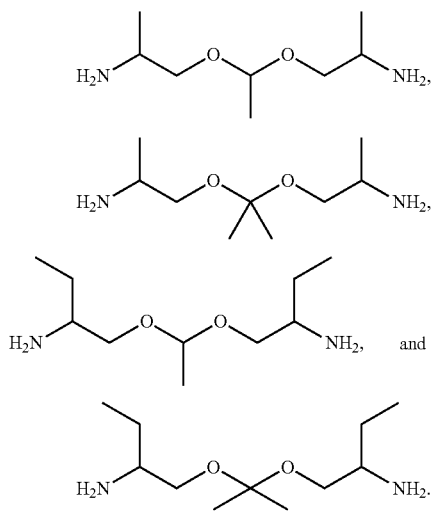

In some embodiments, the compound is selected from the group consisting of

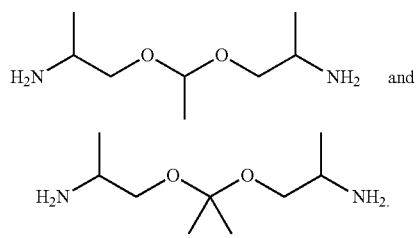

In some embodiments, the compound is selected from the group consisting of

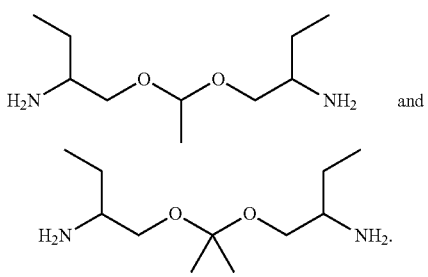

In some embodiments, the compound is selected from the group consisting of

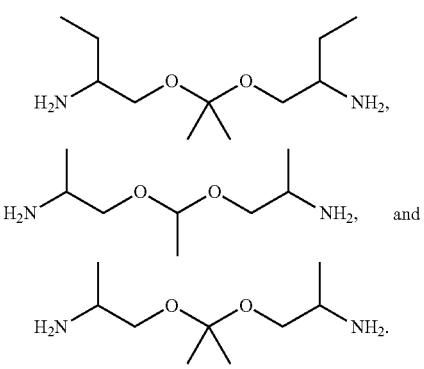

In some embodiments, the epoxy resin composition has a tensile strength of 11,000 or greater psi (75 or greater MPa). In some embodiments, the epoxy resin composition has a tensile modulus of 500,000 or greater psi (3.5 or greater 1 MPa). In some embodiments, the epoxy resin composition has a flexural strength of 16,000 or greater psi (110 or greater MPa). In some embodiments, the epoxy resin composition has a flexural modulus of 450,000 or greater psi (3.1 or greater MPa).

In some embodiments, the epoxy resin composition has working time (e.g., upon contact of the epoxy resin and aliphatic polyamine) of at least 5 hours (e.g., at least 5, 10, 12, 16, 20, 24, 32, 36, 48, 72 hours).

In some embodiments, the epoxy resin comprises an average of at least two epoxide groups per molecule (i.e. at least two epoxide groups per monomer of the epoxy resin).

In some embodiments, the epoxy resin comprises a diepoxide resin selected from a group consisting of glycidyl ether epoxy resin, glycidyl ester epoxy resin, glycidyl amine epoxy resin, alicyclic epoxy resin, aliphatic epoxy resin, phenolic epoxy resin and combinations thereof.

In some embodiments, the epoxy resin comprises a blend of a first bisphenol-based epoxy resin having an epoxide equivalent weight (EEW) in the range of 160 to 220.

In some embodiments, the epoxy resin comprises a second bisphenol-based epoxy resin having an EEW in the range of 400 to 1500.

In some embodiments, the epoxy resin further includes an auxiliary material selected from the group consisting of accelerator, diluents, toughening agent, thickening agent, adhesion promoter, optical brightener, pigment, adducting component, coupling agent, filler, decorative component, thixotropic agent, fluorophore, UV-absorber, anti-oxidant, gloss additive, and combinations thereof.

In some embodiments, the epoxy resin comprises an additional amino molecule (e.g., an additional amine, e.g., aliphatic polyamine, e.g., aliphatic polyamine that does not have a cleavable linking group (e.g., acetal group, ketal group).

In some embodiments, the amino molecule comprises >2 N—H hydrogens.

In some embodiments, the epoxy resin includes an amino molecule containing ≤2 N—H hydrogens.

In some embodiments, the amino molecule contains ≤2 N—H hydrogens is selected from the group consisting of a primary monoamine compound and a bis(secondary) diamine compound.

In some embodiments, the amino molecule contains ≤2 N—H hydrogens, is selected from the group consisting of monoethanolamine, diethanolamine, 3-aminopropanol, 2-aminopropanol, aminobenzylamine, aniline, p-anisidine, butylamine, piperazine, and N,N'-dimethylethylenediamine, tert-butylamine, sec-butylamine. 2-amino-2-methyl-1-propanol and combinations thereof.

In some embodiments, the amino molecule containing ≤2 N—H hydrogens is in an amount selected from the group consisting of less than about 1 wt. % but greater than 0 wt. %, less than about 2 wt. % but greater than 0 wt. %, less than about 5 wt. % but greater than 0 wt. %, less than about 10 wt. % but greater than 0 wt. %, less than about 20 wt. % but greater than 0 wt. %, less than about 30 wt. % but greater than 0 wt. %, less than about 40 wt. % but greater than 0 wt. %, less than about 50 wt. % but greater than 0 wt. %, less than about 60 wt. % but greater than 0 wt. %, less than about 70 wt. % but greater than 0 wt. %, less than about 80 wt. % but greater than 0 wt. %, less than about 90 wt. % but greater than 0 wt. %, less than about 95 wt. % but greater than 0 wt. %, less than about 98 wt. % but greater than 0 wt. % of the composition.

In some embodiments, the epoxy resin further includes a reinforcing agent.

In some embodiments, the reinforcing agent comprises at least one reinforcing component selected from the group consisting of glass fibers, aramid fibers, graphite fibers, carbon fibers, natural fibers, and non-natural fibers.

In some embodiments, the glass transition temperature (Tg) is about 60 to about 155° C. (e.g., about 70 to about 155° C., about 80 to about 155° C., about 90 to about 155° C., about 100 to about 155° C.).

In some embodiments, the tensile strength is about 7,000 to about 13,000 psi (e.g., about 8,000 to about 12,000 psi, about 9,000 to about 11,000 psi).

In some embodiments, the elongation at break is about 2 to about 10% (e.g., about 3 to about 9%).

In some embodiments, the flexural strength is about 12,000 to about 21,000 psi (e.g., about 12,000 to about 18,000 psi, about 13,000 to about 17,000 psi).

In some embodiments, the flexural modulus is about 300,000 to about 600,000 psi (e.g., about 300,000 to about 500,000 psi).

In an aspect, described herein is a method of curing an epoxy resin composition, comprising (i) providing an epoxy resin composition described herein, and (ii) heating the epoxy resin composition.

In some embodiments, the epoxy resin composition is heated to a temperature range of about 20° C. to about 250° C. (e.g., about 20° C. to about 180° C., about 20° C. to about 120° C.).

In some embodiments, the epoxy resin composition is heated to at least about 20° C., 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C.

In some embodiments, the out-life is about 1 week to about 1 year.

In some embodiments, the out-life is at least 1, 2, 3, or 4 weeks; at least 1, 2, 3, 4, 5, 6, 7, 8, 9, 10, 11, or 12 months; at least 1 year.

In an aspect, described herein is a cross-linked polymer matrix derived from an epoxy resin and an aliphatic polyamine cross-linking agent comprising a compound having the structure represented by Formula (2):

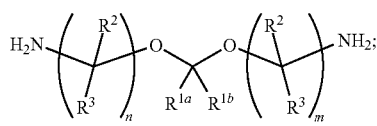

Formula (2)

wherein each of $R^{1a}$ and $R^{1b}$ is independently selected from the group consisting of hydrogen, optionally substituted alkyl (e.g., unsubstituted $C_{1-6}$ alkyl, e.g., —$CH_3$), optionally substituted aryl, and optionally substituted cycloalkyl; each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2).

In some embodiments, $R^{1a}$ is selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); each occurrence of $R^2$ and $R^3$ is independently selected from the group consisting of hydrogen, optionally substituted alkyl, optionally substituted cycloalkyl, and optionally substituted aryl, or $R^2$ and $R^3$ can combine with each other to form optionally substituted cycloalkyl; and each m and n is independently an integer ranging from 1 to 20 (e.g., m and n is independently an integer ranging from 1 to 5, e.g., m and n are both 2), wherein the cross-linked polymer matrix has cross-links derived from the aliphatic polyamine cross-linking agent.

In some embodiments, $R^{1a}$ is hydrogen and $R^{1b}$ is unsubstituted $C_{1-6}$ alkyl. In some embodiments, each of $R^{1a}$ and $R^{1b}$ is independently selected from unsubstituted $C_{1-6}$ alkyl. In some embodiments, $R^{1b}$ is —$CH_3$. In some embodiments, $R^2$ is unsubstituted $C_{1-6}$ alkyl and $R^3$ is hydrogen. In one embodiment, m is 2. In one embodiment, n is 2. In one embodiment, m is 2 and n is 2. In some embodiments, m and n are the same integer (e.g., m and n are both 2).

In some embodiments, the compound of Formula (2) is represented by a compound of Formula (2-a):

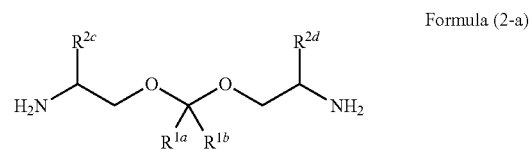

Formula (2-a)

wherein $R^{1a}$ is independently selected from the group consisting of hydrogen and optionally substituted alkyl (e.g., unsubstituted $C_{1-6}$ alkyl, e.g., —$CH_3$); $R^{1b}$ is optionally substituted alkyl (e.g., unsubstituted $C_{1-6}$ alkyl, e.g., —$CH_3$); and each of $R^{2c}$ and $R^{2d}$ is independently selected from optionally substituted alkyl (e.g., unsubstituted $C_{1-6}$ alkyl, e.g., unsubstituted $C_{1-6}$ alkyl selected from the group consisting of —$CH_3$ and —$CH_2CH_3$); and salts thereof.

In some embodiments, $R^{1a}$ is hydrogen and $R^{1b}$ is unsubstituted $C_{1-6}$ alkyl.

In some embodiments, each of $R^{1a}$ and $R^{1b}$ is independently selected from unsubstituted $C_{1-6}$ alkyl. In some embodiments, each of $R^{2c}$ and $R^{2d}$ is independently selected from unsubstituted $C_{1-6}$ alkyl.

In some embodiments, the compound is selected from the group consisting of the compound represented by the Formula (2-a-I) and the compound represented by Formula (2-a-II):

Formula (2-a-I)

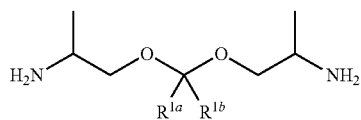

Formula (2-a-II)

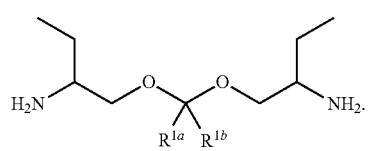

In some embodiments, the compound is selected from the group consisting of the compound represented by the Formula (2-a-I):

Formula (2-a-I)

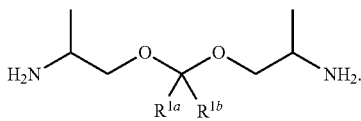

In some embodiments, the compound is selected from the group consisting of the compound represented by the compound represented by Formula (2-a-II):

Formula (2-a-II)

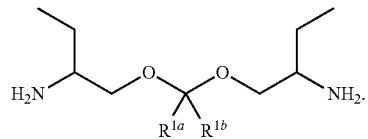

In some embodiments, the compound is selected from the group consisting of the compound represented by the Formula (2-a-I-a) and the compound represented by Formula (2-a-II-a):

Formula (2-a-I-a)

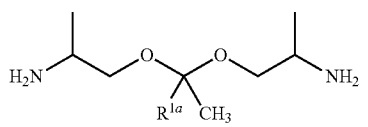

Formula (2-a-II-a)

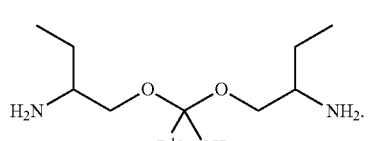

In some embodiments, the compound is selected from the group consisting of the compound represented by the Formula (2-a-I-a):

Formula (2-a-I-a)

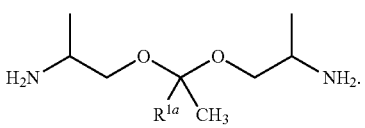

In some embodiments, the compound is selected from the group consisting of the compound represented by the compound represented by Formula (2-a-II-a):

Formula (2-a-II-a)

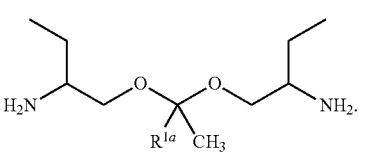

In some embodiments, the compound is selected from the group consisting of

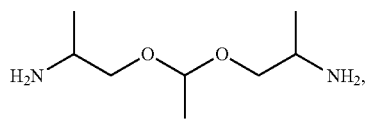

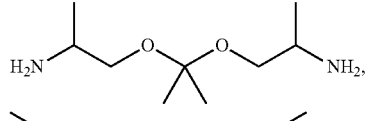

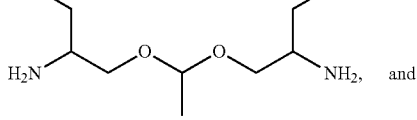

and

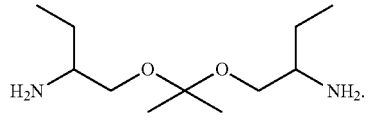

In some embodiments, the compound is selected from the group consisting of

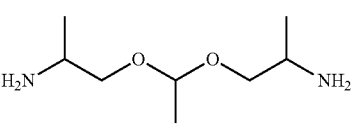

and

In some embodiments, the compound is selected from the group consisting of

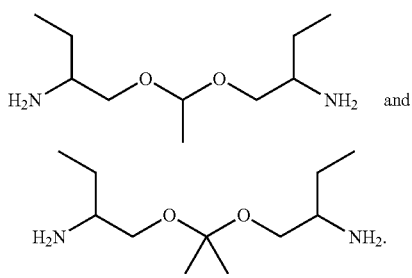

In some embodiments, the compound is selected from the group consisting of

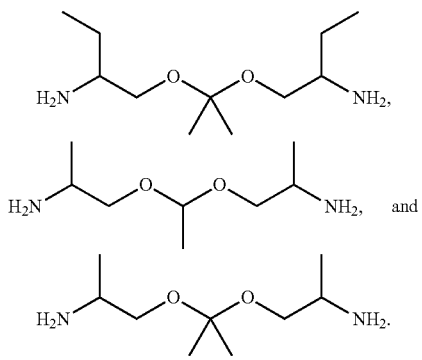

In an aspect, described herein is a reinforced composite material comprising the cross-linked polymer matrix described herein, wherein the reinforced composite is prepared by at least one method selected from a group consisting of wet lay-up, vacuum infusion, infusion, filament winding, and resin transfer molding, prepreg, compression molding, pultrusion and wet pressing.

In an aspect, described herein is a method for recycling a cross-linked polymer matrix or a reinforced composite material described herein comprising degrading the cross-linked polymer matrix using an acid in the presence of a solvent.

In some embodiments, the degrading step is performed under a heating condition.

In some embodiments, the acid is selected from the group consisting of hydrochloric acid, acetic acid, lactic acid, formic acid, propionic acid, citric acid, methane sulfonic acid, p-toluene sulfonic acid, sulfuric acid, benzoic acid, phthalic acid, and combinations thereof.

In some embodiments, the solvent is selected from the group consisting of methanol, ethanol, ethylene glycol, isopropyl alcohol, butyl alcohol, pentanol, hexanol, heptanol, octanol alcohol, nonyl alcohol, water, and combinations thereof.

In some embodiments, the acid has concentration in the solvent in a range from about 2% to 90% by weight in the solvent.

In some embodiments, the acid has concentration in the solvent in a range from about 5% to 25% by weight in the solvent.

In some embodiments, the degradation step is carried out at a temperature ranging from about 15° C. to about 400° C.

In some embodiments, the degradation step is carried out at a temperature ranging from about 80° C. to about 120° C.

In some embodiments, the heating is carried out for a time ranging from about 1 hour to about 48 hours.

In some embodiments, the heating is carried out for a time ranging from about 1 hour to about 12 hours.

In some embodiments, the method further comprises a step of recovering a degradation product of the method for recycling the cross-linked polymer matrix via a precipitation process or a filtration process.

In some embodiments, the method further comprises a step of recovering a degradation product of the method for recycling the cross-linked polymer matrix via a precipitation process and a filtration process.

In an aspect, described herein is a degradation product resulting from the method for recycling the cross-linked polymer matrix and reinforced composite material described herein.

In an aspect, described herein is an adhesive composition comprising the epoxy composition described herein.

In some embodiments, the method comprises degrading the cross-linked polymer matrix using an acid in the presence of a solvent.

In an aspect, described herein is a coating composition comprising the epoxy composition described herein.

In an aspect, described herein is a method of removing, recovering, or recycling of an epoxy coating described herein, comprising degrading the cross-linked polymer matrix using an acid in the presence of a solvent.

In an aspect, described herein is an encapsulating material comprising the epoxy composition described herein.

In an aspect, described herein is a method of removing, recovering, or recycling of an epoxy encapsulation material described herein, comprising degrading the cross-linked polymer matrix using an acid in the presence of a solvent.

In some embodiments, the aliphatic polyamine cross-linking agent (e.g., comprising the compound of Formula (2)) has a working time of from about 4 hours to about 48 hours or more (e.g., 1, 2, 3, 4, 5, 6, 7 days or more).

In some embodiments, the aliphatic polyamine cross-linking agent (e.g., comprising the compound of Formula (2)) has a working time of less than 2 hours.

In some embodiments, the aliphatic polyamine cross-linking agent (e.g., comprising the compound of Formula (2)) has a working time of in between from about 2 hours to 4 hours.

In some embodiments, the aliphatic polyamine cross-linking agent (e.g., comprising the compound of Formula (2)) has a working time of in between from about 4 hours to 8 hours.

In some embodiments, the epoxy resin composition has a working time of from about 4 hours to about 48 hours or more at room temperature, e.g., prior to transforming to a partially or a fully cross-linked polymer matrix.

In some embodiments, after application of an initiating energy (e.g., elevated temperature) to the epoxy resin composition, the epoxy resin composition has a working time of from about 48 hours to about 4 hours, or less (e.g., 4, 3, 2, or 1 hours or less; 60, 50, 40, 30, 20, 10 minutes or less), e.g., prior to the epoxy resin composition forming a partially or a fully cross-linked polymer matrix.

In some embodiments, the aliphatic polyamine cross-linking comprising the compound of Formula (2) has a working time at room temperature of from about 4 hours to about 48 hours or more, e.g., prior to transforming the epoxy resin composition a fully or partially cross-linked polymer matrix.

In some embodiments, the aliphatic polyamine cross-linking agent comprising the compound of Formula (2) is present in an amount sufficient to impart to the epoxy resin composition a setting time period no less than about 48 hours.

In some embodiments, the epoxy resin composition has a working time sufficient to allow manipulation of the epoxy resin composition, e.g., before energy is applied to it to form a cross-linked polymer matrix.

In some embodiments, the working time temperature is from 20 to 30° C.

In some embodiments, conventional, polyamino molecules that contain greater than 2 N—H hydrogens are used in combination with polyamine curing agents of Formula (2). The composition (e.g., formulation) of conventional epoxy curing agents with the polyamine curing agent of Formula (2) will increase the amount of non-degradable cross-links in the final cured epoxy matrix. This action will be, generally, detrimental to the removal and/or recycling of the epoxy composition; however may find use in applications where partial degradation is desired. In one embodiment, non-degradable polyamines in an amount of from about 1 wt. % to 25 wt. % is combined with the polyamine curing agent of Formula (2), e.g., to increase the amount of non-degradable cross-links in the final cured epoxy matrix. In one embodiment, non-degradable polyamine in an amount selected from the group consisting of about 1 wt. % to about 25 wt. %, about 2 wt. % to about 25 wt. %, about 3 wt. % to about 25 wt. %, about 4 wt. % to about 25 wt. %, about 5 wt. % to about 25 wt. %, about 6 wt. % to about 7 wt. %, about 8 wt. % to about 25 wt. %, about 9 wt. % to about 25 wt. %, about 10 wt. % to about 25 wt. %, about 11 wt. % to about 25 wt. %, about 12 wt. % to about 25 wt. %, about 13 wt. % to about 25 wt. %, about 14 wt. % to about 25 wt. %, about 15 wt. % to about 25 wt. %, about 16 wt. % to about 25 wt. %, about 17 wt. % to about 25 wt. %, about 18 wt. % to about 25 wt. %, about 19 wt. % to about 25 wt. %, about 20 wt. % to about 25 wt. %, about 21 wt. % to about 25 wt. %, about 22 wt. % to about 25 wt. %, about 23 wt. % to about 25 wt. %, and about 24 wt. % to about 25 wt. % of the epoxy composition is combined with the polyamine curing agent of Formula (2), e.g., to increase the amount of nondegradable cross-links in the final cured epoxy matrix. Specific, but non-limiting examples of conventional polyamines include polyetheramines and ethyleneamines; and cycloaliphatic and aromatic classes of diamino and/or polyamino molecules.

In some embodiments, the epoxy resin composition further includes a reinforcing agent. In one embodiment, the reinforcing agent is selected from a group consisting of glass fiber, carbon fiber, carbon nanotube fiber, cellulose fiber, natural fiber, chemical fiber, and non-natural fiber. The fiber may be woven or non-woven, unidirectional or multi-directional, chopped matt or any combination thereof. The methods described herein is not limited to the method of applying the epoxy resin composition to the fiber. For example, infusion, wet lay-up, resin transfer molding, vacuum bagging, and other standard composite techniques may also be used In some embodiments, the epoxy resin composition further includes a non-fiber reinforcing agent. Specific, but non-limiting examples, of non-fiber reinforcing agents include carbon nanotube, carbon black, metal nanoparticle, organic nanoparticle, iron oxide, boron nitride, and combinations thereof.

The conventional aliphatic amines that are widely used in coatings and composite applications, like for example, polyethyleneimines, and cycloaliphatic amines (e.g., isophorone diamine) have gel times ranging from minutes to hours at room temperature and do not possess sufficient latency. This reactivity profile makes certain aliphatic amine molecules effectively unsuitable for applications such as filament winding and pultrusion.

Certain diamino curing agents described herein (e.g., diamino curing agents by Formula (2) as described herein) overcome these limitations of conventional aliphatic amines used in the art in two major ways: 1) they have low reactivity with epoxy resins at ambient temperatures; and 2) the contain an acid labile linkages, allowing a cured epoxy to be transformed (i.e. removed and recycled) by simple immersion in an acidic recycling bath.

As described herein, a specific set of acid-labile aliphatic amines is provided, e.g., a compound of Formula (2) as described herein, which possess suitable processing, mechanical, thermal, properties, e.g., for pultrusion, filament winding or large part infusion. These polyamine hardeners can be formulated to create epoxy composition suitable for the fabrication of composites that may serve as the structural materials or reinforcing materials. Furthermore, the curing agents provide a thermosetting epoxy matrix that enables the fabrication of inherently recyclable thermosetting materials. The structure of the cross-links in the cured epoxy matrix from the epoxy compositions disclosed herein is designed in such a way that they are programmed to cleave upon immersion in an acidic recycling bath. The acidic bath induces cleavage of the acid-labile linkages in the thermoset, converting into its thermoplastic counterpart. Both the concentration of acid, and the acid strength (i.e. pH) of the recycling bath can be used to modulate the conversion of the reworkable thermoset into a thermoplastic. The nature of the acid-labile ketal/acetals group can be used as a handle to control the recycling time. Polymers modified with acid-cleavable groups have been successfully implemented in both photoresist and drug delivery applications. The common premise in these cases is that acid-induced cleavage will result in a solubility change in the parent material. This change is then taken advantage of for a technological purpose. The concept of recyclable/reworkable epoxy is somewhat similar, albeit the desired change is to transform an otherwise intractable material into a tractable one that is of high inherent value. The cleavage groups in the programmed epoxy hardeners will exist at every cross-link point in the cured epoxy matrix. Immersion of the cured epoxy in a specific recycling bath will induce cleavage of the cross-links and conversion of the thermoset plastic into its thermoplastic epoxy counterpart. This transformation occurs at an appreciable rate only upon immersion of the thermoset in a solution of sufficient temperature, acid strength and concentration. Generally, most epoxy and composite applications operate in environments that are far away from what is required to trigger the programmed epoxy to convert (e.g., degrade, de-crosslink). The thermoplastic offset is completely insoluble in water, but may be solubilized into an acidic recycling solution because of protonation of the polymer backbone. Thus, any other articles in contact with the initial thermoset (fibers, metal, etc) may be physically removed from the recycling bath and then the dissolved epoxy thermoplastic recovered after a processing step such as evaporation or precipitation.

The exact conditions required (time, temperature, acid strength) to induce the conversion of the reworkable thermoset into a thermoplastic is governed by the exact chemical nature of the acid-labile group in the hardener. In general, the rate of de-crosslinking is ketal>acetal>formal.

In some embodiments, the fibers, metals, copper sheet, additives, or any other articles that are insoluble under the acid bath, may be recovered by physical removal from the resultant/recycling solution. Further, if the converted thermoplastic is dissolved under the operation, it may be recovered from the solution via a simple precipitation or evaporation process. An advantage of the described epoxy resin compositions and methods is that essentially all of the high value input materials bond together by the cure recyclable epoxy composition may be recovered via a simpler, and low energy recycling process, which is afforded by the use of Formula (2) cross-linking agents. Such a recycling process may be performed at the site of product manufacturing, whereby post-production thermoset article waste can be recycled instead of being thrown in the landfill. The described epoxy resin compositions and methods have important environmental and economic implications, as the development of a recyclable thermoset materials is a long-standing challenge of the industry.

As described herein, novel polyamine hardener Formula (2) when used with a typical epoxy resin makes it possible to fabricate epoxy laminates and composite structures, wherein the epoxy can be dissolved, separated and recovered. Among the embodiments of this invention is the incorporation of additional auxiliary material(s) to the base-epoxy composition (i.e., the "A-stage formulation"). The described epoxy resin compositions and methods have the distinct advantage that it enables the manufacture of recyclable products.

In an embodiment, the described epoxy resin compositions and methods have the distinct advantage that it provides epoxy compositions for the fabrication of more easily recycled epoxy-based products. The described epoxy resin compositions and methods are not limited with respect to the exact method used, e.g., to make the laminate or composite product that is used to make a final product. Specific, but non-limiting examples, of procedures for forming composites and laminates involve such operations (which are well known in the composite industry):

A) Wet lay up
B) Infusion
C) filament winding or pultrusion
E) Resin transfer molding, and its derivatives such as e.g., vacuum assisted resin transfer molding, high pressure resin transfer molding, and the like
F) compression molding and wet compression The curable resin composition described herein may contain inorganic fillers, if necessary. Some specific, but non-limiting, examples of the inorganic filler include fused silica, fumed silica, crystalline silica, alumina, silicon nitride, and aluminum hydroxide, aluminum oxide hydroxide, talc, micro glass beds, etc. In consideration of flame retardancy, the filling ratio of the filler is preferably high and is particularly preferably 20% by mass or more of the total amount of the curable resin composition. When the curable resin composition is used in the application of an electrically conductive paste or the like, an electrically conductive filler such as a silver powder or a copper powder can be used. Various compounding agents such as a silane coupling agent, a mold release agent, a pigment, and an emulsifier may be optionally added to the curable resin composition described herein.

In some embodiments, epoxy resin composition described herein further includes a reinforcing agent. In one embodiment, reinforcing agent is selected from a group consisting of glass fiber, carbon fiber, natural fiber, and chemical fiber; and the non-fibrous material is at least one selected from a group consisting of carbon nanotube, carbon black, metal nanoparticle, organic nanoparticle, iron oxide, boron nitride, and combinations thereof.

In another aspect, described herein is a method of curing an epoxy resin composition described herein. In one embodiment, the method comprises heating an epoxy resin composition described herein to form a cured epoxy resin composition. In one embodiment, the epoxy resin composition is cured to a curing degree of at least 5% cure (e.g., as determined by infrared (IR) spectroscopy, differential scanning calorimetry (DSC), or other methods used by a person of skill in the art. In one embodiment, the epoxy resin composition is cured to a curing degree of at least 10% cure. In one embodiment, the epoxy resin composition is cured to a curing degree of at least 15% cure. In one embodiment, the epoxy resin composition is cured to a curing degree of at least 20% cure. In one embodiment, the epoxy resin composition is cured to a curing degree of at least 25% cure. In one embodiment, the epoxy resin composition is cured to a curing degree of at least 30% cure. In one embodiment, the epoxy resin composition is cured to a curing degree of at least 35% cure. In one embodiment, the epoxy resin composition is cured to a curing degree of at least 45% cure. In one embodiment, the epoxy resin composition is cured to a curing degree of at least 55% cure. In one embodiment, the epoxy resin composition is cured to a curing degree selected from the group consisting of at least 65% cure, at least 75% cure, at least 85% cure, and at least 95% cure.

In some embodiments, the method of curing an epoxy resin composition described herein is used to produce reinforced composite. In one embodiment, the method of curing an epoxy resin composition described herein produces a composite reinforced with a reinforcing component selected from the group consisting of glass fibers, aramid fibers, graphite fibers, carbon fibers, natural fibers, non-natural fibers and combinations thereof.

In one embodiment, the cross-linked polymer matrix is reinforced with a reinforcing agent derived from a reinforcing component selected from the group consisting of glass fibers, aramid fibers, graphite fibers, carbon fibers, natural fibers, non-natural fibers and combinations thereof. In one embodiment, the cross-linked polymer matrix is a cross-linked epoxy resin, wherein the epoxy resin is selected from the group consisting of glycidyl ether epoxy resin, glycidyl ester epoxy resin, glycidyl amine epoxy resin, alicyclic epoxy resin, aliphatic epoxy resin, and phenolic epoxy resin. In one embodiment, the cross-linked polymer matrix is reinforced with the reinforcement material selected from the group consisting of a fibrous material and a non-fibrous material. In one embodiment, the cross-linked polymer matrix is reinforced with a fibrous material selected from a group consisting of glass fiber, carbon fiber, natural fiber, and chemical fiber. In one embodiment, the cross-linked polymer matrix is reinforced with a non-fibrous material selected from the group consisting of carbon nanotube, carbon black, metal nanoparticle, organic nanoparticle, iron oxide, and boron nitride. In one embodiment, the reinforced cross-linked polymer matrix includes an auxiliary material selected from the group consisting of accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, and gloss additive. In some embodiments, the reinforced cross-linked polymer matrix is prepared by at least one method selected from the group consisting of wet lay-up, vacuum infusion, filament winding, and resin transfer molding, prepreg, and compression molding.

Figure 5:
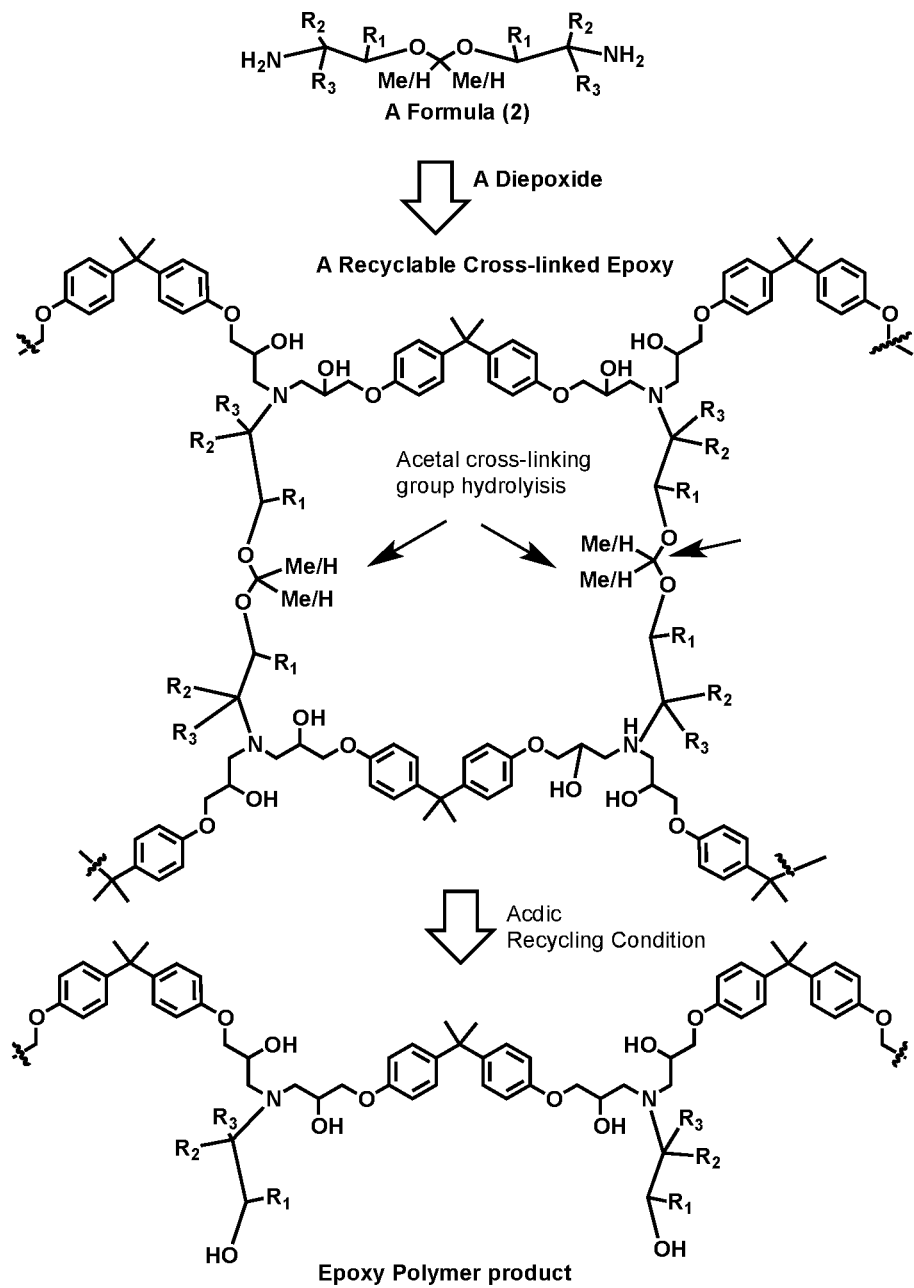
FIG. 5 shows a non-limiting example of the method for recycling a cross-linked polymer matrix described herein.

In another aspect, described herein is a method for recycling a cross-linked polymer matrix described herein. FIG. 5 shows a non-limiting example of the method for recycling a cross-linked polymer matrix described herein. In one embodiment, the method for recycling the cross-linked polymer matrix comprises degrading the cross-linked polymer matrix with an acid in the presence of a solvent. In one embodiment, degrading the cross-linked matrix with an acid in the presence of a solvent is performed under a heating condition. In one embodiment, the cross-linked polymer matrix is degraded with an acid selected from a group consisting of hydrochloric acid, acetic acid, lactic acid, formic acid, propionic acid, citric acid, methane sulfonic acid, p-toluene sulfonic acid, sulfuric acid, benzoic acid, and phthalic acid. In one embodiment, the cross-linked polymer matrix is degraded with an acid in the presence of a solvent selected from the group consisting of methanol, ethanol, ethylene glycol, isopropyl alcohol, butyl alcohol, pentanol, hexanol, heptanol, octanol alcohol, nonyl alcohol, water, and combinations thereof. In one embodiment, the cross-linked polymer matrix is degraded with an acid in an amount ranging from about 2% to 90% by weight of the cross-linked polymer matrix. In one embodiment, the cross-linked polymer matrix is degraded with an acid in an amount selected from at least about 2 wt. %, 3 wt. %, 4 wt. %, 5 wt. %, 6 wt. %, 7 wt. %, 8 wt. %, 9 wt. %, 10 wt. %, 15 wt. %, 20 wt. %, 25 wt. %, 30 wt. %, 35 wt. %, 40 wt. %, 45 wt. %, 50 wt. %, 55 wt. %, 60 wt. %, 65 wt. %, 70 wt. %, 75 wt. %, 80 wt. %, 85 wt. %, 90 wt. % of the cross-linked polymer matrix.

In one embodiment, the cross-linked polymer matrix is degraded with an acid in an amount selected from the group consisting of about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, about 85 wt. %, about 86 wt. %, about 87 wt. %, about 88 wt. %, about 89 wt. %, and about 90 wt. % of the polymer matrix.

In some embodiments, the method for recycling a cross-linked polymer matrix described herein is carried out under a heating condition. In one embodiment, the cross-linked polymer matrix is degraded at a temperature ranging from 15° C. to 400° C. In one embodiment, the cross-linked polymer matrix is degraded at a temperature ranging from 60° C. to 120° C. In one embodiment, the cross-linked polymer matrix is degraded at a temperature selected from the group consisting of about 60° C. to about 120° C., about 61° C. to about 120° C., about 62° C. to about 120° C., about 63° C. to about 120° C., about 64° C. to about 120° C., about 65° C. to about 120° C., about 66° C. to about 120° C., about 67° C. to about 120° C., about 68° C. to about 120° C., about 69° C. to about 120° C., about 70° C. to about 120° C., about 71° C. to about 120° C., about 72° C. to about 120° C., about 73° C. to about 120° C., about 74° C. to about 120° C., about 75° C. to about 120° C., about 76° C. to about 120° C., about 77° C. to about 120° C., about 78° C. to about 120° C., about 79° C. to about 120° C., about 80° C. to about 120° C., about 81° C. to about 120° C., about 82° C. to about 120° C., about 83° C. to about 120° C., about 84° C. to about 120° C., about 85° C. to about 120° C., about 86° C. to about 120° C., about 87° C. to about 120° C., about 88° C. to about 120° C., about 89° C. to about 120° C., about 90° C. to about 120° C., about 91° C. to about 120° C., about 92° C. to about 120° C., about 93° C. to about 120° C., about 94° C. to about 120° C., about 95° C. to about 120° C., about 96° C. to about 120° C., about 97° C. to about 120° C., about 98° C. to about 120° C., about 99° C. to about 120° C., about 100° C. to about 120° C., about 101° C. to about 120° C., about 102° C. to about 120° C., about 103° C. to about 120° C., about 104° C. to about 120° C., about 105° C. to about 120° C., about 106° C. to about 120° C., about 107° C. to about 120° C., about 108° C. to about 120° C., about 109° C. to about 120° C., about 110° C. to about 120° C., about 111° C. to about 120° C., about 112° C. to about 120° C., about 113° C. to about 120° C., about 114° C. to about 120° C., about 115° C. to about 120° C., about 116° C. to about 120° C., about 117° C. to about 120° C., about 118° C. to about 120° C., and about 119° C. to about 120° C.

In one embodiment, the cross-linked polymer matrix is degraded at a temperature selected from the group consisting of about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., about 105° C., about 106° C., about 107° C., about 108° C., about 109° C., about 110° C., about 111° C., about 112° C., about 113° C., about 114° C., about 115° C., about 116° C., about 117° C., about 118° C., about 119° C., and about 120° C.

In some embodiments, the cross-linked polymer matrix is degraded at a temperature ranging from 20° C. to 400° C. In one embodiment, the cross-linked polymer matrix is degraded at a temperature selected from the group consisting of about 20° C. to about 400° C., about 25° C. to about 400° C., about 30° C. to about 400° C., about 35° C. to about 400° C., about 40° C. to about 400° C., about 45° C. to about 400° C., about 50° C. to about 400° C., about 55° C. to about 400° C., about 60° C. to about 400° C., about 65° C. to about 400° C., about 70° C. to about 400° C., about 75° C. to about 400° C., about 80° C. to about 400° C., about 85° C. to about 400° C., about 90° C. to about 400° C., about 95° C. to about 400° C., about 100° C. to about 400° C., about 105° C. to about 400° C., about 110° C. to about 400° C., about 115° C. to about 400° C., about 120° C. to about 400° C., about 125° C. to about 400° C., about 130° C. to about 400° C., about 135° C. to about 400° C., about 140° C. to about 400° C., about 145° C. to about 400° C., about 150° C. to about 400° C., about 155° C. to about 400° C., about 160° C. to about 400° C., about 165° C. to about 400° C., about 170° C. to about 400° C., about 175° C. to about 400° C., about 180° C. to about 400° C., about 185° C. to about 400° C., about 190° C. to about 400° C., about 195° C. to about 400° C., about 200° C. to about 400° C., about 205° C. to about 400° C., about 210° C. to about 400° C., about 215° C. to about 400° C., about 220° C. to about 400° C., about 225° C. to about 400° C., about 230° C. to about 400° C., about 235° C. to about 400° C., about 240° C. to about 400° C., about 245° C. to about 400° C., about 250° C. to about 400° C., about 255° C. to about 400° C., about 260° C. to about 400° C., about 265° C. to about 400° C., about 270° C. to about 400° C., about 275° C. to about 400° C., about 280° C. to about 400° C., about 285° C. to about 400° C., about 290° C. to about 400° C., about 295° C. to about 400° C., about 300° C. to about 400° C., about 305° C. to about 400° C., about 310° C. to about 400° C., about 315° C. to about 400° C., about 320° C. to about 400° C., about 325° C. to about 400° C., about 330° C. to about 400° C., about 335° C. to about 400° C., about 340° C. to about 400° C., about 345° C. to about 400° C., about 350° C. to about 400° C., about 355° C. to about 400° C., about 360° C. to about 400° C., about 365° C. to about 400° C., about 370° C. to about 400° C., about 375° C. to about 400° C., about 380° C. to about 400° C., about 385° C. to about 400° C., about 390° C. to about 400° C., and about 395° C. to about 400° C.

In some embodiments, the cross-linked polymer matrix is degraded at a temperature selected from the group consisting of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., about 190° C., about 195° C., about 200° C., about 205° C., about 210° C., about 215° C., about 220° C., about 225° C., about 230° C., about 235° C., about 240° C., about 245° C., about 250° C., about 255° C., about 260° C., about 265° C., about 270° C., about 275° C., about 280° C., about 285° C., about 290° C., about 295° C., about 300° C., about 305° C., about 310° C., about 315° C., about 320° C., about 325° C., about 330° C., about 335° C., about 340° C., about 345° C., about 350° C., about 355° C., about 360° C., about 365° C., about 370° C., about 375° C., about 380° C., about 385° C., about 390° C., about 395° C., and about 400° C.

In some embodiments, the cross-linked polymer matrix is degraded by heating the cross-linked polymer matrix with an acid at a temperature selected from the group consisting of less than about 400° C. but greater than about 10° C., less than about 395° C. but greater than about 10° C., less than about 390° C. but greater than about 10° C., less than about 385° C. but greater than about 10° C., less than about 380° C. but greater than about 10° C., less than about 375° C. but greater than about 10° C., less than about 370° C. but greater than about 10° C., less than about 365° C. but greater than about 10° C., less than about 360° C. but greater than about 10° C., less than about 355° C. but greater than about 10° C., less than about 350° C. but greater than about 10° C., less than about 345° C. but greater than about 10° C., less than about 340° C. but greater than about 10° C., less than about 335° C. but greater than about 10° C., less than about 330° C. but greater than about 10° C., less than about 325° C. but greater than about 10° C., less than about 320° C. but greater than about 10° C., less than about 315° C. but greater than about 10° C., less than about 32° C. but greater than about 10° C., less than about 305° C. but greater than about 10° C., less than about 300° C. but greater than about 10° C., less than about 295° C. but greater than about 10° C., less than about 290° C. but greater than about 10° C., less than about 285° C. but greater than about 10° C., less than about 280° C. but greater than about 10° C., less than about 275° C. but greater than about 10° C., less than about 270° C. but greater than about 10° C., less than about 265° C. but greater than about 10° C., less than about 260° C. but greater than about 10° C., less than about 255° C. but greater than about 10° C., less than about 250° C. but greater than about 10° C., less than about 245° C. but greater than about 10° C., less than about 240° C. but greater than about 10° C., less than about 235° C. but greater than about 10° C., less than about 230° C. but greater than about 10° C., less than about 225° C. but greater than about 10° C., less than about 220° C. but greater than about 10° C., less than about 215° C. but greater than about 10° C., less than about 22° C. but greater than about 10° C., less than about 205° C. but greater than about 10° C., less than about 200° C. but greater than about 10° C., less than about 195° C. but greater than about 10° C., less than about 190° C. but greater than about 10° C., less than about 185° C. but greater than about 10° C., less than about 180° C. but greater than about 10° C., less than about 175° C. but greater than about 10° C., less than about 170° C. but greater than about 10° C., less than about 165° C. but greater than about 10° C., less than about 160° C. but greater than about 10° C., less than about 155° C. but greater than about 10° C., less than about 150° C. but greater than about 10° C., less than about 145° C. but greater than about 10° C., less than about 140° C. but greater than about 10° C., less than about 135° C. but greater than about 10° C., less than about 130° C. but greater than about 10° C., less than about 125° C. but greater than about 10° C., less than about 120° C. but greater than about 10° C., less than about 115° C. but greater than about 10° C., less than about 12° C. but greater than about 10° C., less than about 105° C. but greater than about 10° C., less than about 100° C. but greater than about 10° C., less than about 95° C. but greater than about 10° C., less than about 90° C. but greater than about 10° C., less than about 85° C. but greater than about 10° C., less than about 80° C. but greater than about 10° C., less than about 75° C. but greater than about 10° C., less than about 70° C. but greater than about 10° C., less than about 65° C. but greater than about 10° C., less than about 60° C. but greater than about 10° C., less than about 55° C. but greater than about 10° C., less than about 50° C. but greater than about 10° C., less than about 45° C. but greater than about 10° C., less than about 40° C. but greater than about 10° C., less than about 35° C. but greater than about 10° C., less than about 30° C. but greater than about 10° C., less than about 25° C. but greater than about 10° C., less than about 20° C. but greater than about 10° C., and less than about 15° C. but greater than about 10° C.

In some embodiments, the cross-linked polymer matrix is degraded by heating the cross-linked polymer matrix with an acid for a time of from about 1 hour to about 48 hours. In some embodiments, the cross-linked polymer matrix is degraded by heating the cross-linked polymer matrix with an acid for a time of from about 1 hour to 12 hours.

In some embodiments, the cross-linked polymer matrix is degraded by heating the cross-linked polymer matrix with an acid for a time selected from the group consisting of about 1 hour to about 48 hours, about 2 hours to about 48 hours, about 3 hours to about 48 hours, about 4 hours to about 48 hours, about 5 hours to about 48 hours, about 6 hours to about 48 hours, about 7 hours to about 48 hours, about 8 hours to about 48 hours, about 9 hours to about 48 hours, about 10 hours to about 48 hours, about 11 hours to about 48 hours, about 12 hours to about 48 hours, about 13 hours to about 48 hours, about 14 hours to about 48 hours, about 15 hours to about 48 hours, about 16 hours to about 48 hours, about 17 hours to about 48 hours, about 18 hours to about 48 hours, about 19 hours to about 48 hours, about 20 hours to about 48 hours, about 21 hours to about 48 hours, about 22 hours to about 48 hours, about 23 hours to about 48 hours, about 24 hours to about 48 hours, about 25 hours to about 48 hours, about 26 hours to about 48 hours, about 27 hours to about 48 hours, about 28 hours to about 48 hours, about 29 hours to about 48 hours, about 30 hours to about 48 hours, about 31 hours to about 48 hours, about 32 hours to about 48 hours, about 33 hours to about 48 hours, about 34 hours to about 48 hours, about 35 hours to about 48 hours, about 36 hours to about 48 hours, about 37 hours to about 48 hours, about 38 hours to about 48 hours, about 39 hours to about 48 hours, about 40 hours to about 48 hours, about 41 hours to about 48 hours, about 42 hours to about 48 hours, about 43 hours to about 48 hours, about 44 hours to about 48 hours, about 45 hours to about 48 hours, about 46 hours to about 48 hours, and about 47 hours to about 48 hours.

In some embodiments, the cross-linked polymer matrix is degraded by heating the cross-linked polymer matrix with an acid for a time selected from the group consisting of less than about 48 hours but greater than about 1 hour, less than about 47 hours but greater than about 1 hour, less than about 46 hours but greater than about 1 hour, less than about 45 hours but greater than about 1 hour, less than about 44 hours but greater than about 1 hour, less than about 43 hours but greater than about 1 hour, less than about 42 hours but greater than about 1 hour, less than about 41 hours but greater than about 1 hour, less than about 40 hours but greater than about 1 hour, less than about 39 hours but greater than about 1 hour, less than about 38 hours but greater than about 1 hour, less than about 37 hours but greater than about 1 hour, less than about 36 hours but greater than about 1 hour, less than about 35 hours but greater than about 1 hour, less than about 34 hours but greater than about 1 hour, less than about 33 hours but greater than about 1 hour, less than about 32 hours but greater than about 1 hour, less than about 31 hours but greater than about 1 hour, less than about 30 hours but greater than about 1 hour, less than about 29 hours but greater than about 1 hour, less than about 28 hours but greater than about 1 hour, less than about 27 hours but greater than about 1 hour, less than about 26 hours but greater than about 1 hour, less than about 25 hours but greater than about 1 hour, less than about 24 hours but greater than about 1 hour, less than about 23 hours but greater than about 1 hour, less than about 22 hours but greater than about 1 hour, less than about 21 hours but greater than about 1 hour, less than about 20 hours but greater than about 1 hour, less than about 19 hours but greater than about 1 hour, less than about 18 hours but greater than about 1 hour, less than about 17 hours but greater than about 1 hour, less than about 16 hours but greater than about 1 hour, less than about 15 hours but greater than about 1 hour, less than about 14 hours but greater than about 1 hour, less than about 13 hours but greater than about 1 hour, less than about 12 hours but greater than about 1 hour, less than about 11 hours but greater than about 1 hour, less than about 10 hours but greater than about 1 hour, less than about 9 hours but greater than about 1 hour, less than about 8 hours but greater than about 1 hour, less than about 7 hours but greater than about 1 hour, less than about 6 hours but greater than about 1 hour, less than about 5 hours but greater than about 1 hour, less than about 4 hours but greater than about 1 hour, less than about 3 hours but greater than about 1 hour, and less than about 2 hours but greater than about 1 hour.

In some embodiments, the cross-linked polymer matrix is degraded by heating the cross-linked polymer matrix with an acid for a time selected from the group consisting of 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, and about 48 hours.

In some embodiments, the cross-linked polymer matrix is degraded by heating the cross-linked polymer matrix with an acid for a time selected from the group consisting of less than about 48 hours but greater than about 1 hour, less than about 47 hours but greater than about 2 hours, less than about 46 hours but greater than about 3 hours, less than about 45 hours but greater than about 4 hours, less than about 44 hours but greater than about 5 hours, less than about 43 hours but greater than about 6 hours, less than about 42 hours but greater than about 7 hours, less than about 41 hours but greater than about 8 hours, less than about 40 hours but greater than about 9 hours, less than about 39 hours but greater than about 10 hours, less than about 38 hours but greater than about 11 hours, less than about 37 hours but greater than about 12 hours, less than about 36 hours but greater than about 13 hours, less than about 35 hours but greater than about 14 hours, less than about 34 hours but greater than about 15 hours, less than about 33 hours but greater than about 16 hours, less than about 32 hours but greater than about 17 hours, less than about 31 hours but greater than about 18 hours, less than about 30 hours but greater than about 19 hours, less than about 29 hours but greater than about 20 hours, less than about 28 hours but greater than about 21 hours, less than about 27 hours but greater than about 22 hours, less than about 26 hours but greater than about 23 hours, and less than about 25 hours but greater than about 24 hours.

In some embodiments, the method for recycling a cross-linked polymer matrix includes the step of recovering a degradation product of the cross-linked polymer matrix via a filtration process and/or a precipitation process.

In general, the diamino compounds of Formula (2) can be used as monomers and/or cross-linkers to make polymeric materials such as nylons, epoxies, polyurethanes, acrylamides or other type polymers or cross-linked polymers and/or materials. The diamino compounds of Formula (2) can also be used as monomers or cross-linkers for the preparation of designer materials that can further be imbued with the ability to degrade under acidic conditions. Polymer degradation can be accomplished with these materials because, inter alia, the incorporated acetal and ketal linkages are susceptible to cleavage by various chemical means. For example, the acetal and ketal linkages can be cleaved by hydrolysis under acidic conditions. Thus, use of the present diaminoacetals and diaminoketals of Formula (2) as monomers produce polymeric structure that can be predictably degraded into smaller molecular fragments under acidic conditions.

Similarly, use of the present diaminoacetals and diaminoketals of Formula (2) as cross-linkers produce polymeric materials that can be cleaved into smaller molecular fragments by cleaving the aminoacetal and aminoketals of the cross-links, for example, under acidic conditions. The rate of acid hydrolysis of acetal and ketals linkages can be used to fine-tune the physical properties of the polymeric materials. In general, the rate of acid hydrolysis decreases in the order of ketal>acetal>formal. Thus, polymeric materials that contain these acid-labile linkages can be useful in designing more environmentally sustainable materials that can be degraded at will via chemical means.

In some embodiments, the epoxy resin composition disclosed herein can be used as an adhesive composition. In some embodiments, the epoxy composition disclosed herein can be used as a coating composition. In some embodiments, the epoxy composition disclosed herein can be used as an encapsulation material. In some embodiments, an epoxy composition disclosed herein can be used as epoxy flooring, e.g., to provide a recyclable floor. In some embodiments, an epoxy composition disclosed herein can be used as epoxy countertop, to provide recyclable countertop. In some embodiments, an epoxy composition disclosed herein can be used to create a recyclable windmill blade.

The present disclosure details cleavable polyamino compounds, some of which provide epoxy resin compositions with extended working times and/or out-life that are suitable for use in industrial composite manufacturing techniques such as filament winding, pultrusion, prepreg, which are process that are otherwise not applicable to epoxy compositions that contain aliphatic polyamines. The epoxy resin compositions described herein may be used in oil and gas-related applications, e.g., for Cured In Place Pipe Repair (CIPP). Additionally, the epoxy compositions described herein have the ability to be easily removed, recycled, dissolved, or otherwise reworked after they have been cured. In an embodiment, a fluid can pass through an industrial composite comprising the epoxy composition described herein. In an embodiment, a first, non-dissolving (e.g., non-acidic) fluid is passed through the industrial composite comprising the epoxy composition described herein. In an embodiment, a second, dissolving (e.g., acidic) fluid is pass through the industrial composite comprising the epoxy composition described herein (e.g., to dissolve or degrade the epoxy composition described herein). The epoxy compositions described herein can also not be recycled or reworked. Thus, the described epoxy resin compositions and methods should find industrial application that include, as non-limiting examples, removable coatings and encapsulates, recyclable carbon fiber thermoset composites, recyclable fiberglass thermoset composites. An example of an industrial application for the epoxy compositions described herein include repair of e.g., an underground pipe, e.g., by layering a fiberglass sleeve in the resin. In some embodiments, the epoxy resin composition has enhanced pliability. An epoxy resin composition for CIPP is a specific, but non-limiting, example of an application.

It will be appreciated by those skilled in the art that changes could be made to the exemplary embodiments shown and described above without departing from the broad inventive concept thereof. It is understood, therefore, that the described epoxy resin compositions and methods are not limited to the exemplary embodiments shown and described, but it is intended to cover modifications within the spirit and scope of the disclosure and as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the methods described herein should not be limited to the performance of their steps in the order written, and one skilled in the art can readily appreciate that the steps may be varied and still remain within the spirit and scope of the present invention.

Definitions

"Alkyl" refers to a radical of a straight-chain or branched saturated hydrocarbon group having from 1 to 6 carbon atoms ("$C_{1-6}$ alkyl"), also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_2$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl (C4), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. Common alkyl abbreviations include Me (—CH$_3$), Et (—CH$_2$CH$_3$), iPr (—CH(CH$_3$)$_2$).

"Aliphatic" refers to an alkyl or carbocyclyl group, as defined herein.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). The cycloalkyl groups can contain fused rings. Fused rings are rings that share a common carbon atom. Examples of cycloalkyl moieties include, but are not limited to, cyclopropyl, cyclohexyl, methylcyclohexyl, adamantyl, and norbornyl.

Alkyl and cycloalkyl as defined herein, are optionally substituted (e.g., "substituted" or "unsubstituted" alkyl, "substituted" or "unsubstituted" carbocyclyl, group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

As used herein, an "aldehyde equivalent" refers to a reactant in a chemical synthesis that is not an aldehyde and, when reacted with one or more other reactants under certain conditions, yields the same chemical product(s) as if said aldehyde equivalent were an aldehyde.

As used herein, an "ketone equivalent" refers to a reactant in a chemical synthesis that is not an aldehyde and, when reacted with one or more other reactants under certain conditions, yields the same chemical product(s) as if said ketone equivalent were a ketone.

As used herein, a "salt" of a compound refers to a compound having at least one anionic charge, cationic charge, or both, where each charge has associated with it a counterion. "Counterion" refers to an ion that balances the compound's anionic or cationic charge. Non-limiting exemplary counterions are anions such as chloride, bromide, fluoride, iodide, acetate, carboxylate, hydrogen sulfate, nitrate, and phenolate, sulfonate, sulfate, and phosphate. A salt described herein can be a monoammonium salt or diammonium salt. As used herein, a "monoammonium salt" of a compound described herein refers to a salt in which one amine in the compound carries a positive charge (e.g., by becoming protonated) whose positive charged is balanced by a counterion. As used herein, a "diammonium salt" of a compound described herein refers to a salt in which two amines in the compound carry a positive charge (e.g., carry a positive charge by becoming protonated) whose positive charged is balanced by one or more counterions (e.g., two chloride anions or one sulfate anion).

EXAMPLES

In order that the invention described herein may be more fully understood, the following examples are set forth. The examples described in this application are offered to illustrate the aspects of the invention and their embodiments provided herein and are not to be construed in any way as limiting their scope.

Example 1. Mechanistic Overview and Process Details for the Synthesis of Diaminoacetals of Type Formula (2-c) from Salts of Formula (3-c) and an Aldehyde or Ketone Equivalent

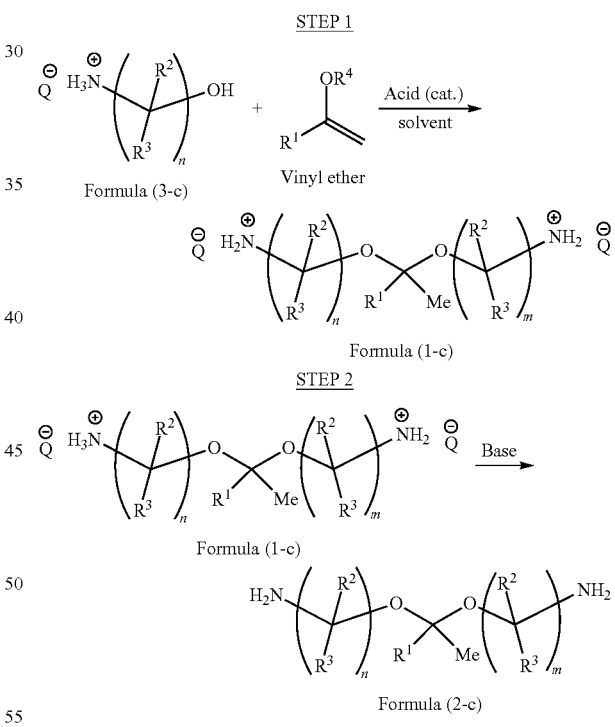

The production of diaminoacetals from the reaction of aminoalcohol salt and a vinyl ether (or a masked aldehyde or masked ketone), proceeds via the formation of a diaminoacetal salt (i.e., Formula (1); STEP 1); and subsequent formation of the freebase via neutralization (i.e., Formula (2); STEP 2).

Step 1

The reaction of an aminoalcohol salt of type Formula (3-c) with vinyl ethers is catalyzed by acids and is exothermic.

The reaction of an aminoalcohol salt with masked ketones (e.g. dimethoxypropane) or masked aldehydes (e.g., acetaldehyde dimethyl acetal) is also catalyzed by acids. A variety of acid catalysts can be used, and this invention is not particularly limited by the type, strength, or nature of the acid catalyst used. The acid catalyst, is preferably a strong acid. Some specific, but non-limiting, examples of strong acid catalyst include para toluene sulfonic acid [PTSA], methanesulfonic acid, HCl (g). It is preferable to use an acid catalyst that is not aqueous-based because any water in the reaction medium can also react with the vinyl ether. One equivalent of water will consume two equivalents of vinyl ether. Thus, as the vinyl ether (or other aldehyde/ketone equivalents) is an essential reagent, the presence of water in the reaction process will impact the raw material economics of the process. Weaker acids can also induce the STEP 1 reaction and may be employed. A variety of common solvents or solvent mixtures may be used in STEP 1 and this invention is not particularly limited by the type of a solvent used. It is preferable to use inexpensive solvents that can be recycled. Protic solvent such as alcohols are not advised, as they can also react with the vinyl ether, consuming the critical reagent. For example, the process can be carried out in a DMSO/toluene mixture using EA HCl in the form of a suspension and with PTSA as the catalyst. The suspension can be azeotropically dried prior to the addition of the vinyl ether. Alternatively, a slight stoichiometric excess (e.g., 1-15%) of vinyl ether can be used, as vinyl ethers can also serve to remove trace water under the acidic conditions. The controlled addition of the vinyl ether to the suspension is typically preferred. It has been discovered that the reaction mechanism does not proceed via direct conversion of the vinyl ether, but rather through the formation an intermediate mixed acetal salt Formula (5) in this process, which is the product of simple addition of the vinyl ether to the alcohol group of the amino alcohol salt.

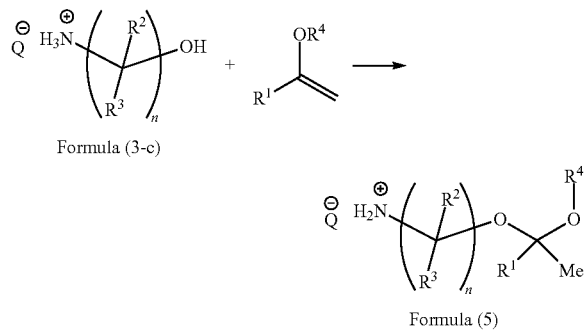

When the mixed acetal salt intermediate Formula (5) is more soluble in the reaction solvent than the starting amino alcohol salt, the reaction suspension may dissolve completely or begin to solubilize and become visibly less viscous ('thinner') during the course of vinyl ether addition. The formation of the salt of type Formula (1-c) occurs via a direct conversion of the mixed acetal salt intermediate, presumably via a disproportionation process. By virtue of being a dicationic, Formula (1-c) compounds typically have less inherent solubility in the reaction solvent than the mixed acetal intermediate or the starting aminoalcohol salt, which are both monocationic. A disproportionation reaction of the mixed acetal salt places it in equilibrium with Formula (1-c) and a dialkoxyalkane product. As a result of this solubility differential, a mechanism is provided to drive the formation of the Formula (1-c) via selective precipitation of Formula (1-c).

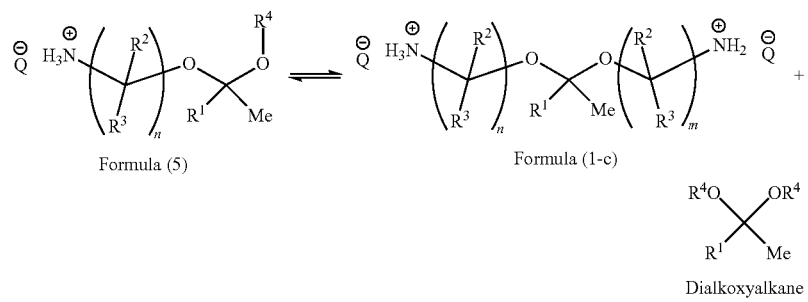

It should be noted that the above equation is equilibrium that is 'driven forward' by precipitation of the Formula (1) salt. The choice of solvent is a critical factor determining the forward conversion/precipitation of the desired diamine salt. One factor that influences the choice of solvent is that the starting aminoalcohol salt Formula (3-c) remain a suspension in the solvent, but also with enough solubility in the chosen solvent to yield a reaction with 2-methoxypropene. If Formula (3-c) salt has too little solubility, then it will not be available to react with 2-methoxypropene, and the reaction pathway will not be productive. Alternatively, if the solubility of targeted diamine salt Formula (1-c) is too high in a given solvent, it may not precipitate completely, or at all. The practical outcome of this scenario is that the yield of Formula (1) salts will be low because without the driving force of precipitation as it will still be in dynamic equilibrium with Formula (5) in solution. Other factors influencing the choice of solvent include, the ability to recycle the solvent, cost, and the stability of the solvent toward acidic and basic conditions present at different stages of the process. The reaction progress can be monitored by a gas chromatography of the saponified reaction mixture.

In yet another aspect, when the isolated salt of mixed ketal Formula (5) is heated without solvent, it will melt and start reacting according to the above equation producing a dialkoxy alkane and salt of type Formula (1-c). The salt of Formula (1-c), having higher melting point, will then start to crystalize out from the melted salt of Formula (5) containing dialkoxyalkane, and thus driving the equilibrium in forward.

Step 2

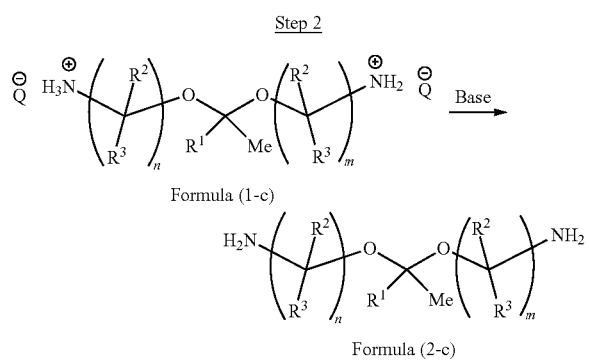

Formula (1-c)

Formula (2-c)

In an aspect, Polyaminoacetals of type Formula (2-c) are obtained by subjection of Formula (1-c) type compounds to a basic condition (STEP 2). Typically, it is preferable to directly carry out STEP 2 after the completion of STEP 1. Just as this invention is not particularly limited by the choice of solvent, or the type of catalyst used in STEP 1, this invention is not particularly limited to the basic condition used in STEP 2, and its corresponding operational steps. Nevertheless, care must be taken by the practitioner to avoid the hydrolysis of Formula (1-c) back into its parent aminoalcohol during STEP 2. Acetals and ketal molecules are well known to be sensitive to hydrolysis under acidic, or slightly acidic, conditions. We have found that salts of type Formula (2-c) are rather stable to hydrolysis, provided that the surrounding media is not acidic. Furthermore, Formula (1-c) salts may be isolated, stored, and converted to Formula (2-c) at a later time.

The incomplete conversion of Formula (1-c) into Formula (2-c) may lead to complications in the downstream purification of Formula (2-c) compounds. For example, the presence of trace amounts of Formula (1-c) salts (i.e. trace mono-ammonium salt or trace di-ammonium salts), can lead to decomposition of Formula (2-c) during distillation, resulting in higher than anticipated amounts of parent aminoalcohols and related decomposition products during purification. To this end, it is advisable to carry out STEP 2, with at least the equivalent amount of base to account for the complete neutralization of both the Formula (1-c) salt and the acid catalyst. Similarly, it is preferable to use a sufficiently strong base for the freebase step, such there is no equilibrium between the protonated form of the added base and Formula (2-c). Although there are a variety of bases that can be used to satisfy these criteria, it is preferable to use sodium hydroxide for economic reasons, and most preferable to use aqueous sodium hydroxide solutions, which is also called "caustic" (i.e., 50 wt % caustic, i.e., 30 wt % caustic, i.e., 10 wt % caustic). Typically, it is preferable to use the caustic solution in slight stoichiometric excess (1-20%) over the amount required for complete neutralization, although the amount not particularly limiting, provided that isolation of Formula (2-c) is not problematic due to the basic condition used.

Operationally, there are variety of process pathways that can be used to carry out STEP 2, and this invention is not limited by the process operation used to carry out STEP 2. This STEP 2 can be broken down into two fundamental parts: 1) a neutralization/free base component to yield Formula (2-c); and 2) isolation/purification on Formula (2-c). Some specific, but non-limiting, process operations for STEP 2 include the direct neutralization of the crude reaction from STEP 1, the reverse neutralization of the reaction mixture of STEP 1, and the, first, isolation of Formula (1-c) from STEP 1 followed by neutralization.

Neutralization Component of STEP 2

Direct neutralization entails the addition of the caustic solution directly to the reactor vessel from STEP 1. The resulting exotherm may be controlled by caustic addition rate or with external cooling. For example, the addition of the 50 wt % caustic solution to the Formula (1-c) suspension will result in liquefaction of the suspended Formula (1-c) (i.e., as it converts into the freebase Formula (2-c)), with concomitant formation of sodium chloride precipitates. With a direct neutralization process, a pre-quench of the acid catalyst prior to the addition of the caustic solution may be advisable to mitigate any propensity for back hydrolysis that may occur during the initial stage of caustic addition. To execute the catalyst pre-quench, the requisite amount of base is added to neutralize the acid catalyst used in STEP 1. There is no particular limitation on the base used in the optional pre-quench. The base is preferably a base with a low water content, and is preferably an amine base, and more preferably the amine base is the Formula (2-c) compound or its parent amino alcohol, to simplify purification process during downstream isolation or recycling steps.

Reverse neutralization entails the addition of the crude reaction contents from STEP 1 to the caustic solution. Operationally, this process for STEP 2 involves the transfer of the reactor contents from STEP 1 into a $2^{nd}$ vessel already containing the caustic. As with the direct neutralization process, a catalyst pre-quench may proceed the transfer of the STEP 1 reaction contents to the caustic containing vessel, although the reverse quench process, itself, helps to mitigate back hydrolysis of Formula (2-c).

As an alternative to direct or reverse neutralization, Formula (1-c) salts may be directly isolated from STEP 1 by, for example, a filtration operation. For example, the reaction medium from STEP 1 can be passed through a centrifuge, whereby the Formula (1-c) salts are collected and separated from the liquid components (i.e. solvents, dialkoxyalkane, dissolved acid catalyst). Formula (1-c) salts may be stored, and can be converted to Formula (2-c) at a later time. The liquid component can be recycled.

By virtue of being ionic, the ammonium salts are hygroscopic and it is advisable to store them in a closed container and in low humidity environment. It should be noted that any acid present in the salt will promote the hydrolysis of acetal portion of the salts (e.g. back hydrolysis). It has been found that the storage stability Formula (1-c) salts be can greatly increased if measures are enacted to remove the acid catalyst from STEP 1 prior to storage, for example, vis-a-via the optional pre-quench step described above for the direct or reverse neutralization methods. This pre-quench step mitigates the entrapment of the acid catalyst from STEP 1 in the isolated Formula (1-c) salts, thereby decreasing their back hydrolysis propensity upon storage. Without acid present in the salts, the salts have been found to be stable to storage in closed containers for periods of time. Amine bases, including aminoalcohols or Formula (2-c) compounds, are preferred if a pre-quench is carried out.

Isolation & Purification Component of STEP 2

After either the direct- or reverse neutralization step, the downstream isolation and purification of Formula (2-c) can follow the same course, as either method provides Formula (2-c) in effectively the identical media (i.e., in a similar solvent, water, inorganic salts, etc. mixture). Ultimately, Formula (2-c) is obtained in high purity by vacuum distillation, but the most efficient set of process operations leading up to a final distillation depend on, to an extent, the inherent solubility properties of the specific Formula (2-c) polyaminoacetal being manufactured and the solvent used in STEP 1 component. If the Formula (2-c) compound has limited solubility in water and good solubility in the reaction solvent, then after STEP 2, the layers can be cut, the organic solvent stripped (and recycled), and then Formula (2-c) polyaminoacetal obtained in high purity after vacuum distillation. On the other hand, if the Formula (2-c) compound has substantial solubility in the aqueous medium, then a set of operations may be employed to obtain and purify it from the aqueous layer. There are number of ways that Formula (2-c) can be recovered from aqueous layer, and the most efficient set of operations can easily be determined by one skilled in the art. As one example, the more volatile components (e.g. solvent, dialkoxyalkane byproduct, water) may be stripped from the reactor, the inorganic salts filtered, and the resulting crude Formula (2-c) purified via distillation. With such a process, it may be advantageous to add a high boiling solvent (i.e., one with a significantly higher boiling point that the Formula (2-c) compound) as a processing aid because a large volume of inorganic salts develop during striping of the aqueous layer. Once the low boiling components have been stripped, the salts can be removed, and the Formula (2-c) distilled from the processing aid. It may also be advantageous to add such a processing aid up front in STEP 1 as the reaction solvent or co-solvent. If the STEP 2 process route entails the isolation of the Formula (1-c) salt and subsequent neutralization, then, for example, the inorganic salts filtered, the water (and any remaining trace solvents striped), and Formula (2-c) purified via distillation. With regard to distillation of Formula (2-c), in addition to water and solvents, the impurity profile typically comprises the freebases corresponding to the Formula (3-c) aminoalcohol and the Formula (5) mixed acetal. With the appropriate STEP 1 conditions, It is possible to drive the formation of Formula (1-c) to high conversions (i.e. >90%), and as such, the amounts of Formula (3) & (4) freebases will be low. Furthermore, these amine freebases have lower boiling points than that of their corresponding Formula (2-c), thus the isolation of Formula (2-c) in high purity (i.e. >98%) is easily facilitated by standard distillation process in the art.

Other Processing Guidelines

While, this invention is not particularly limited by the choice of solvent, appropriate guidelines have been provided. For any high-volume process, the ability to recycle solvents is a critical factor in the manufacturing cost, and for this invention the choice of solvents that can be recycled is preferred. It should be noted that in the process described by this invention, when vinyl ethers are used as the aldehyde/ketone equivalent, the production of polyaminoacetals occurs with the concomitant formation of a dialkoxyalkane. In an aspect, the dialkoxyalkane can be recovered, converted into a vinyl ether, and the vinyl ether re-used in to STEP 1 Process.

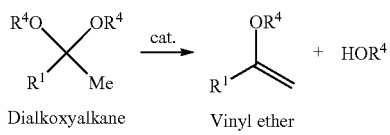

Dialkoxyalkane     Vinyl ether

Example 2. Synthesis of
2,2-Bis(2-amino-ethoxy)propane

Toluene (30 kg), dimethyl sulfoxide (10 kg) and ethanolamine hydrochloride (fine crystals, 10 kg, 102 mol) were charged to a jacketed 100 L reactor equipped with a very efficient stirrer, temperature sensor and nitrogen inlet. The chiller connected to the jacket was set to 5° C. and the internal temperature of the reactor was brought to 5° C. with vigorous stirring. Para toluene sulfonic acid (50 g, 0.25 mol) was then added to the reactor. 2-Methoxypropene (8.4 kg, 116 mol) was added to the reaction slurry in 4 portions over 3 hours while maintaining the temperature below 35° C. The reaction gradually became a very thick slurry during this time with the formation of a very fine crystals of 2,2-bis(2-aminoethoxy)propane dihydrochloride. The reaction slurry was stirred for additional 3 hours. An aliquot was taken from the reaction mixture, quenched with 50% NaOH with vigorous stirring and diluted with methanol. GC analysis showed 98% desired product with less than 1% of ethanolamine and less than 1% of mixed ketal. The reaction mixture in the reactor was quenched by addition of 50% sodium hydroxide solution (10 kg, 126 mol) with vigorous stirring. There was a controllable exothermic process observed after addition of NaOH. The contents of the reactor were stirred for additional 2 hrs. The salts were separated by filtration and the bottom aqueous layer of the filtrate was collected (19.5 kg). The top organic layer was extracted with water (2 times; 3 kg each) and all aqueous layers were combined (33 kg). The combined aqueous layers were distilled using fractionating column under vacuum to give the title product (7.4 kg, 93% yield) as a clear liquid. Boiling point: 61° C. at 1.2 mmHg. $^1$H NMR (400 MHz, CDCl$_3$): 1.13 (br s, 4H), 1.22 (s, 6H), 2.69 (t, J=5.2 Hz, 4H), 3.31 (t, J=5.2 Hz, 4H).

Comparative Example 2.1

This example demonstrates the isolation of a Formula (2-c) salt from STEP 1, and its subsequent conversion to Formula (2-c)

Toluene (158 kg), dimethyl sulfoxide (39 kg) and ethanolamine hydrochloride (fine crystals, 50 kg, 512.8 mol) were charged to a jacketed 500 L reactor equipped with a very efficient stirrer, temperature sensor and nitrogen inlet. The chiller connected to the jacket was set to 5° C. and the internal temperature inside the reactor was brought to 5-10° C. with vigorous stirring. Para toluene sulfonic acid (110 g, 0.55 mol) was added to the reactor. 2-Methoxypropene (37.5 kg, 520.8 mol) was added to the reaction slurry in 4 portions over 3 hours while maintaining the temperature below 35° C. The reaction gradually became a very thick slurry during this time with a formation of very fine crystals of 2,2-bis (2-amino-ethoxy)propane dihydrochloride. The reaction mixture remained stirable and was stirred for additional 3 hours. An aliquot was taken from the reaction mixture, quenched with 50% NaOH with vigorous stirring and diluted with methanol. GC analysis showed 98% desired product with less than 1% of ethanolamine and less than 1% of mixed ketal. To the reactor, 150 g of 2,2-bis(2-amino-ethoxy)propane was added in one portion and the content of the reactor was transferred to a centrifuge and filtered at 1000 rpm. The resulting cake was washed with 25 kg of toluene. Wet 2,2-bis(2-amino-ethoxy)propane dihydrochloride (78.2 kg) was collected from the centrifuge and 208 kg of organic filtrate was drained that can re-used in a repeated same process.

The salt of 2,2-bis(2-amino-ethoxy)propane dihydrochloride was sampled and analyzed by Malvern® MaserSizer laser diffractor using toluene as dispersant. Surface-weighted mean diameter was found to be 13.3 µm and volume-weighted diameter: 23.9 µm. Size distribution was measured as follows: 10% of particles were smaller than 7.9 µm, 50% of particles were smaller than 22.3 µm and 90% were smaller than 42.1 µm.

A jacketed reactor was charged with 50 kg of 50% NaOH and the isolated in the previous operation wet salts of 2,2-bis(2-amino-ethoxy)propane dihydrochloride were added in portions with vigorous stirring. The salts dissolved with a formation of suspension of sodium chloride in a mixture of three distinct phases: top layer—mostly toluene, middle layer—mostly 2,2-bis(2-amino-ethoxy)propane layer and bottom aqueous layer saturated with salts. The suspension was filtered using a mono-plate filter and filtrate collected. Filtrate was separated, and the two top layers were distilled using fractionating column under vacuum to give the title product (22.8 kg, 55% yield) as a clear liquid. Boiling point: 61° C. at 1.2 mmHg. 1H NMR (400 MHz, CDCl$_3$): 1.13 (br s, 4H), 1.22 (s, 6H), 2.69 (t, J=5.26 Hz, 4H), 3.31 (t, J=5.26 Hz, 4H).

Comparative Example 2.2

This example demonstrates the use of a different strong acid catalyst in STEP 1, and anhydrous base in STEP 2

In a vial was placed ethanolamine hydrochloride (4.09 g, 42 mmol) containing residual HCl, dimethyl formamide (4 g) and 2-methoxypropene (4.09 g, 57 mmol) was added in portions at room temperature. The vial was briefly warmed up and mixture solidified. Concentrated ammonia (3 g) was added after which the mixture was gently heated and solids dissolved while ammonium chloride crystallized. 50% NaOH was next added (10 g) and two layers resulted. The top layer was separated and yielded 11 g of mixture of the desired product and mixed ketal with ethanolamine in the ratio of 65% (desired product):30% (mixed ketal):5% (ethanolamine)

Comparative Example 2.3

This example demonstrates the use of a weak acid catalyst in the process.

A 10 L jacketed glass reactor, equipped with a very efficient mechanical stirrer, thermocouple, was charged with ethanolamine hydrochloride (1.295 kg, 13.28 mol), 6.5 kg of dichloromethane, 170 g of DMSO, 40 g of acetic acid and 2 g of pyridinium para-toluene sulfonate. Jacket was set to 10° C. and 2-methoxypropene (1.26 kg, 17.5 mol) was added in portions over 20 minutes and at temperature of 12-18° C. Jacket temperature was changed to 20° C. Yellow clear solution formed with solids of ethanolamine hydrochloride still present. The reaction was stirred overnight and it turned into thick milky suspension. Concentrated aqueous ammonia (0.925 L) was added and stirred 5 minutes, followed by water (0.46 L) and the two layers formed. The top layer (aqueous) was separated and cooled to 4° C. and solid sodium hydroxide was added (780 g) in portions with cooling. Organic layer separated out. Aqueous layer was washed with 200 mL of dichloromethane and combined with organic layer. and aqueous layer was washed 1×100 mL methyl tert-butyl ether. Combined organic layers were concentrated and distilled using fractionating column under vacuum to give the title product (575 g, 53% yield, purity by GC 95%).

Comparative Example 2.4

This example demonstrates the use of a masked aldehyde/ketone in place of a vinyl ether.

A 1 L round-bottom flask in a heating bath, equipped with a very efficient mechanical stirrer, thermocouple, distillation head was charged with ethanolamine hydrochloride (100 g, 1.025 mol), 200 g of dimethylformamide, 3 g of PTSA, and 2,2-dimethoxypropane (100 g, 0.96 mol). The reaction mixture was heated to about 70° C. to dissolve all the components and ~100 g of distillate was collected at 60-70° C. at ~100 mmHg vacuum. Another portion of 2,2-dimethoxypropane (100 g, 0.96 mol) was added and procedure was repeated and addition of 2,2-dimethoxypropane (2×100 g) and distillation was repeated two more times. In total 400 g of 2,2-dimethoxypropane was used. After the end of fourth distillation, the remaining organic solvent was removed by distillation as well (~110 g of mostly DMF was collected) at 60-70° C. at ~3 mmHg vacuum. 20 g of ethanolamine and 800 g of 30% NaOH was added with vigorous stirring. Organic layer was separated and aqueous layer was washed 1×100 mL methyl tert-butyl ether. Combined organic layers were concentrated using a rotary evaporator, dried with sodium sulfate and distilled using fractionating column under vacuum to give the title product (25 g, 31% yield, b.p. ~80° C. at 1.5 mmHg).

Comparative Example 2.5

This example demonstrates the use of different Q+ counterion in the process.

A 1 L round-bottom flask in a heating bath, equipped with a efficient stirrer, thermocouple, distillation head was charged with 2,2-dimethoxypropane (31.2 g, 0.3 mol) and glacial acetic acid (30 g, 0.5 mol). Ethanolamine (15 g, 0.246 mol) was added dropwise while reaction was distilled. Total of 23 g of distillate was collected. An aliquot was taken from the reaction mixture, quenched with 50% NaOH with vigorous stirring and diluted with methanol. GC analysis showed 2% desired product with 41% of mixed ketal and 25% (ethanolamine)

Example 3. Synthesis of 1,1-Bis(2-amino-ethoxy)ethane

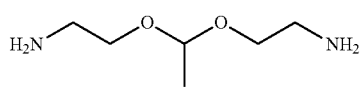

Dichloromethane (160 kg) and ethanolamine hydrochloride (39.1 kg, 542 mol) were charged to a jacketed 500 L reactor. The chiller connected to the jacket was set to 5° C. and the internal temperature inside the reactor was brought to 5° C. Para toluene sulfonic acid (750 g, 3.9 mol) was then added to the reactor. Ethyl vinyl ether (29.5 kg, 409 mol) was added to the reaction in 4 portions over 5 hours while maintaining the temperature below 25° C. The reaction was stirred for the next 24 hrs during which time it turned into a thick slurry. The reaction was quenched by transferring the reaction mixture on a reactor containing 50% sodium hydroxide solution (40 kg, 500 mol) and the contents were stirred for 2 hrs. The salts were separated by filtration and the organic layer of the filtrate was collected. The top aqueous layer was extracted with methylene chloride (10 kg) and all organic layers were combined (33 kg). The combined organic layer was concentrated on a rotary evaporator and the residue was purified by vacuum distillation to provide the desired product (13 kg, 43% yield) as a clear colorless liquid. A $^1$H NMR (400 MHz, CDCl$_3$): 1.32 (d, J=4.8 Hz, 3H), 1.42 (br s, 4H), 2.86 (t, J=5.2 Hz, 4H), 3.46 (dxt, J=9.6 Hz, J=5.2 Hz, 2H), 3.63 (dxt, J=9.6 Hz, J=5.2 Hz, 2H), 4.74 (q, J=4.8 Hz, 1H)

Example 4. Synthesis of 2,2-Bis(2-amino-propoxy)propane

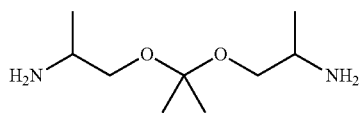

2-Amino-propan-1-ol hydrochloride (12.5 kg, 112 mol) and acetone (37.5 kg, 0.9) were charged to a jacketed 500 L reactor. The chiller connected to the jacket was set to 5° C. and the internal temperature inside the reactor was brought to 5° C. PTSA (100 g, 0.5 mol) was added to the reactor. 2-Methoxypropene (9.5 kg, 132 mol) was added to the reaction in 4 portions over 3 hours while maintaining the temperature below 35° C. The reaction was stirred for the next 72 hours and the reaction became a thick slurry during this time. An aliquot was taken from the reaction mixture, quenched with 50% NaOH and taken up in methanol. GC analysis showed >98% conversion to the desired product. The reaction was quenched by adding 50% sodium hydroxide solution (10.5 kg, 130 mol) and the contents were stirred for 2 hrs and then the salts were allowed to settle. The pH of the top liquid layer was confirmed to be >12, indicating complete neutralization. The top liquid layer was pumped out and concentrated on a rotary evaporator. Water (2 times; 3 kg) was added and the mixture was concentrated again. The residue was collected and distilled under vacuum to provide the desired product as a clear oil (8.7 kg, 82% yield). $^1$H NMR (400 MHz, CDCl$_3$): 1.04 (d, J=6.4 Hz, 6H), 1.36 (br s, 10H), 3.0-3.2 (m, 4H), 3.3-3.4 (m, 2H)

Example 5. Synthesis of 2,2-Bis(2-amino-butoxy)propane

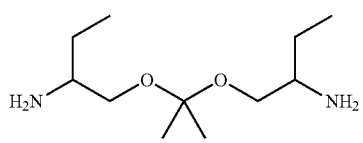

Concentrated hydrochloric acid (280 g, 37% solution) and toluene (500 g) were charged to a 2 L flask cooled to 10° C. with an ice-water bath. 2-Amino-1-butanol (250 g, 2.8 mol) was added to the biphasic solution slowly over 90 mins. The ice-bath was removed, and a Dean-Stark condenser was attached. The solution was heated to reflux and the water was collected in the Dean-Stark trap. Over the next 14 hrs, a total of 200 g of water was collected and removed. Dimethyl sulfoxide (150 g) was then added to the solution along with PTSA (5.3 g, 0.03 mol) at room temperature. 2-Methoxypropene (190 g, 2.6 mol) was then added to the reaction over the next 2 hours. A thick precipitate started forming towards the end of this addition and then mixture was stirred vigorously for 3 hrs. An aliquot of the solids was taken from the reaction mixture, quenched with 50% NaOH and taken up in methanol. GC analysis showed 95% of the desired product. The reaction was quenched by adding 50% sodium hydroxide (670 g), stirred for 30 mins and then the salts were removed by filtration. The filtrate had two layers—the top organic layer was collected, concentrated to remove low boiling solvents and then the residue (430 g) was purified by vacuum distillation to give the product as a clear liquid (233 g, 81% yield). $^1$H NMR (400 MHz, CDCl$_3$) d 0.95 (t, J=6.4 Hz, 6H, 1.25-1.35 (m, 4H), 1.36 (s, 6H), 1.45-1.55 (m 4H), 2.75-2.85 (m, 2H), 3.10-3.20 (m, 2H), 3.40-3.45 (m, 2H).

Example 6. Synthesis of 2,2-Bis(2-amino-2-methylpropoxy)propane

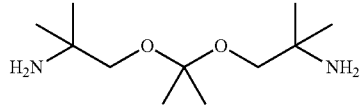

2-Amino-2-methyl propanol hydrochloride (14.4 kg, 115 mol), para toluene sulfonic acid (164 g, 0.9 mol) and acetone (45 kg) were charged to a jacketed 500 L reactor. The chiller connected to the jacket was set to 0° C. and the internal temperature inside the reactor was brought to 10° C. 2-Methoxypropene (8.9 kg, 124 mol) was added to the reaction in 2 portions over 3 hours while maintaining the temperature below 30° C. The reaction was stirred for the next 18 hours and the reaction became a thick slurry during this time. An aliquot was taken from the reaction mixture, quenched with 50% NaOH and taken up in methanol. GC analysis showed >95% desired product. The reaction was quenched by adding 50% sodium hydroxide solution (11 kg, 137 mol) and the contents were stirred for 2 hrs and then the salts were allowed to settle. The top liquid layer was pumped out and concentrated on a rotary evaporator. The residue was collected (13.9 kg) and distilled under vacuum to provide the desired product as a clear liquid (10.5 kg, 88% yield). $^1$H NMR (400 MHz, CDCl$_3$): 1.09 (s, 12H), 1.27 (br s, 4H), 1.35 (s, 6H), 3.14 (s, 4H)

Comparative Example 6.1

This example demonstrates the direct conversion of a mixed salt of type Formula (5) to Formula (1-c) without a solvent A small round-bottom flask was charged with mixed ketal hydrochloride formed from acetone, methanol and 2-amino-2-methylpropanol hydrochloride (35.6 g, 0.18 mol). The flask was placed in a heating mantle and gently heated to 60° C. while closed, while the solids melted. After 30 minutes at 60° C. the mixture solidified. The reaction was heated for additional 30 minutes at 60° C. and cooled to room temperature. 30 g of aqueous ammonia was added and mixture shaken until dissolved. Added 20 g of 50% sodium hydroxide and stirred briefly. Organic layer was separated and concentrated on a rotary evaporator to give pure desired product 2,2-Bis(2-amino-2-methylpropoxy)propane (11 g, 56% yield).

Comparative Example 6.2

This example demonstrates the use of a weak acid catalyst in the process.
A small round-bottom flask was charged with 2-amino-2-methyl-1-propanol hydrochloride (5.05 g, 40.2 mmol), acetone (25 g), 2-methoxypropene (3 g, 41.7 mmol) and 0.15 g of pyridinium para-toluene sulfonate. The content of the flask was stirred overnight at room temperature. An aliquot was taken from the reaction mixture, quenched with 50% NaOH with vigorous stirring and diluted with methanol. GC analysis showed 95% desired product 2,2-Bis(2-amino-2-methylpropoxy)propane, along with 5% of its mixed ketal intermediate.

Example 7. Synthesis of Bis(2-amino-2-methylpropoxy)ethane

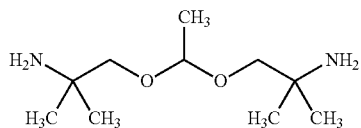

A small round-bottom flask was charged with 2-amino-2-methyl-1-propanol hydrochloride (4 g, 31.8 mmol), acetone (16 g), ethyl vinyl ether (2.3 g, 31.9 mmol) and 70 mg of para-toluene sulfonic acid. The content of the flask was stirred for 5 hours at room temperature. An aliquot was taken from the reaction mixture, quenched with 50% NaOH with vigorous stirring and diluted with methanol. GC analysis showed 82% desired product bis(2-amino-2-methylpropoxy)ethane, along with 18% of its mixed ketal intermediate: 1-(2-amino-2-methylpropoxy)-1-methoxyethane.

Example 8. Mechanistic Overview and Process Details for Synthesis of Diaminoacetals of Type Formula (2-c) from a Salt of the Compound of Formula (3-c) and an Aldehyde in the Presence of an Acid

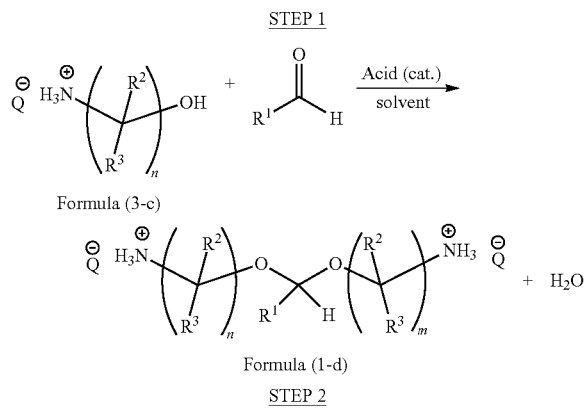

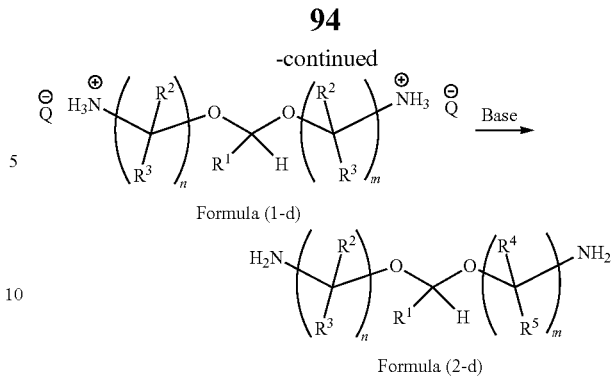

The production of diaminoacetals from the reaction of aminoalcohol salt and formaldehyde (or formaldehyde equivalent, e.g. paraformaldehyde), proceeds via the formation of a diaminoacetal salt (i.e., Formula (1); STEP 1); and subsequent formation of the freebase via neutralization (i.e., Formula (2); STEP 2).

Step 1

The reaction of an aminoalcohol salt of type Formula (3-c) with formaldehyde (and its analogues) and aldehydes is catalyzed by acids. A variety of acid catalysts can be used, and this invention is not particularly limited by the type, strength, or nature of the acid catalyst used. The acid catalyst is preferably a strong acid. Some specific, but non-limiting, examples of strong acid catalysts include Lewis acids like silicon tetrachloride, boron trifluoride etherate, titanium tetraisopropoxide and protic acids like concentrated sulfuric acid and hydrochloric acid. It is preferable to use an acid catalyst that is not aqueous-based because water is a by-product of the reaction and the reaction can be reversed by excess of water. The conversion of aminoalcohol salt of Formula 3-c to acetal salt of Formula 1-d is essentially an equilibrium that can be (1) driven forward by elimination of water from the reaction mixture or (2) precipitation of Formula 1 salt or both of these processes. In one aspect, water may react with an additional reagent used in the process and thus be removed from the equilibrium. In one aspect, the reagent may serve as both the acid catalyst and the dehydrating agent. One such reagent may be a silicon regent such as silicon tetrachloride, which produces, irreversibly, hydrogen chloride and silicon dioxide when reacted with water. A variety of common solvents or solvent mixtures may be used in STEP 1 and this invention is not particularly limited by the type of a solvent used. Preferably, a suitable solvent should be either a one that: (1) does not substantially dissolve the Formula 1 salt and/or (2) is compatible with the catalyst or other reagents agent used in the process. It is preferable to use inexpensive solvents that can be recycled or reused. Protic solvent such as alcohols are not advised, as they can also react with carbonyl compound, consuming the critical reagent. Other non-inert solvents, especially those not compatible with strong acids and water are also not advised. As just one example, the process can be carried out in acetonitrile using ethanolamine hydrochloride in the form of a suspension and with silicon tetrachloride as the catalyst. Alternatively, the process can also be carried out in methyl-tert-butyl ether with concentrated sulfuric acid as the catalyst. In yet another aspect, there may be no solvent used. For example, ethanolamine hydrochloride may be reacted with paraformaldehyde in the presence of sulfuric acid without any additional solvent. A variety of amino alcohol salts can be used in Step 1 of the reaction. Specific, but non-limiting examples, of amino alcohol salts include ethanolamine hydrochloride, 2-aminopropanol hydrochloride, 2-methyl-2-aminopropanol hydrochloride and 2-aminobutanol hydrochloride. Apart from paraformaldehyde, 1,3,5-trioxane, formaldehyde gas may also be used as the source of methylene group in the product. In yet another aspect formaldehyde hydrate, namely formalin, or formaldehyde chloroalkyl ether, namely methoxymethyl chloride can also be used as the source of methylene group in the product. With respect to paraformaldehyde, it is noteworthy that its use in the powdered form was found to be essential in the reaction of ethanolamine hydrochloride with sulfuric acid, as the reaction with paraformaldehyde in the prilled form was not found to be productive.

Typically, the two reagents (e.g. Formula (3-c) and formaldehyde) are mixed in the chosen solvent to get a slurry which is brought to a desired temperature. The catalyst is added, which initiates the reaction, typically resulting in a change in solids behavior of the suspension. In reactions carried out at elevated temperatures, the suspended solids may liquefy, creating a bi-phasic mixture, and, as the reaction progresses, the Formula (1-d) product begins to rapidly precipitate out. When the reaction is carried out at lower temperatures, in some cases, the reaction mixture may become gummy or even solidify, when it progresses, so that stirring becomes problematic. This is especially the case when no solvent is added, and it such case it would be preferable to carry out the reaction in a specialized apparatus for agitating sludge, or very high solids content.

The following scheme describes the proposed reaction mechanism when ethanolamine hydrochloride is reacted with formaldehyde to yield Formula (1-d; Q=Cl⁻, R1=R2=R3=H, n=2) in the presence of a strong protic acid catalyst. The acid catalyst undergoes exchange with the chloride anion of the amine salt and the chloride anion activates paraformaldehyde, which gets attacked by the amino-alcohol to generate intermediates Formula (5) or Formula (6). Not being bound by theory, the Intermediate Formula (5) then eliminates one molecule of water and undergoes addition of another molecule of amino-alcohol to produce Formula (1-d) product. The Intermediate Formula (6) may undergo directly an attack by another molecule of amino-alcohol and also produce bis-salt Formula (1-d). The Formula (1-d) precipitates from the reaction mixture thus driving the equilibrium forward.

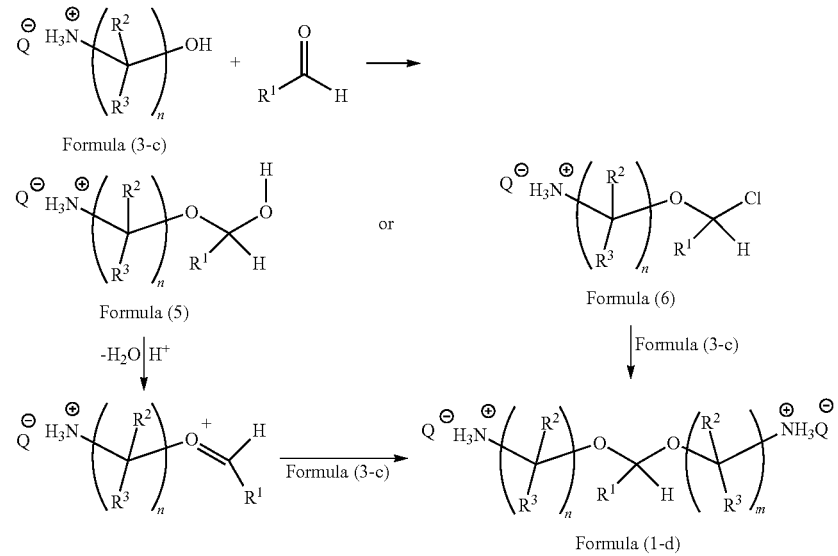

Further support for a mechanistic pathway involving chlorinated intermediate such as Formula (6) is provided by the following additional experimental observations: 1) the reaction of ethanolamine hydrochloride with methyl chloromethyl ether produced Formula (1-d; Q=Cl⁻, R1=R2=R3=H, n=2); and 2) the reaction of ethanolamine hydrochloride with bis chloromethyl ether also produced Formula (1-d; Q=Cl⁻, R1=R2=R3=H, n=2). Both of these experimental observations demonstrate the productive formation of the Formula (1-d)-type products, without the use of the formaldehyde reagent.

The Formula (1-d) products may be stored either as suspension in the reaction mixture or isolated (e.g., via a filtration operation) and stored. Alternatively, the Formula (1-d) product may be converted into Formula (2-d) without prior isolation and/or storage.

Step 2

Direct neutralization entails the addition of the caustic solution directly to the reactor vessel from STEP 1. The resulting exotherm may be controlled by caustic addition rate or with external cooling. The addition of the 50 wt % caustic solution to the Formula (1-d) suspension will result in liquefaction of the suspended Formula (1-d) (i.e., as it converts into the freebase Formula (2-d)), with concomitant formation of sodium chloride that may precipitate. With a direct neutralization process, a pre-quench of the acid catalyst prior to the addition of the caustic solution may be advisable to mitigate any propensity for back hydrolysis of the salt of Formula (1-d) during the initial stage of caustic addition. To execute the catalyst pre-quench, the requisite amount of base is added to neutralize the acid catalyst used in STEP 1. There is no particular limitation on the base used in the optional pre-quench. The base is preferably a base with a low water content, and is preferably an amine base, and more preferably the amine base is the Formula (2-d)

compound or its parent amino alcohol, as it can later be recovered during downstream isolation or recycling steps. Reverse neutralization entails the addition of the crude reaction contents from STEP 1 to the caustic solution. Operationally, this process for STEP 2 involves the transfer of the reactor contents from STEP 1 into a $2^{nd}$ vessel already containing the caustic. As with the direct neutralization process, a catalyst pre-quench may proceed the transfer of the STEP 1 reaction contents to the caustic containing vessel, although the reverse quench process, itself, helps to mitigate back hydrolysis of Formula (2-d).

As an alternative to direct or reverse neutralization, Formula (1-d) salts may be directly isolated from STEP 1 by, for example, a filtration operation. For example, the reaction medium from STEP 1 can be passed through a centrifuge, whereby the Formula (1-d) salts are collected and separated from the liquid components (i.e. solvents, dialkoxyalkane, dissolved acid catalyst). Formula (1-d) salts may be stored, and can be converted to Formula (2-d) at a later time.

By virtue of being ionic, salts are hygroscopic and it is advisable to store them in closed container and in low humidity environment. It should be noted that any acid present in the salt will promote the hydrolysis of acetal portion of the salts. It has been found that the storage stability Formula (1-d) salts be can greatly increased if measures are enacted to remove the acid catalyst from STEP 1 prior to storage, for example, vis-a-via the optional pre quench step described above for the direct or reverse neutralization methods. This pre-quench step mitigates the entrapment of the acid catalyst from STEP 1 in the isolated Formula (1-d) salts, thereby decreasing their hydrolysis propensity upon storage. Without acid present in the salts, the salts have been found to be stable to storage in closed containers for periods of time. Bis-salt of Formula 1-d is sensitive towards water and may hydrolyze back into carbonyl compound and amino alcohol salt Formula (3-c) if exposed to moisture; and needs to be stored tightly closed.

Example 9. Synthesis of bis(2-aminoethoxy)methane

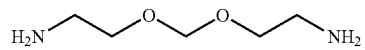

Ethanolamine hydrochloride (2.0 kg, 20.5 mol), paraformaldehyde (310 g, 10.3 mol) and acetonitrile (3.5 L) were charged to a 10 L jacketed reactor set at 20° C. Silicon tetrachloride (44 g, 0.26 mol) was then added to the reaction which was stirred vigorously for the next 24 hrs. An aliquot was taken from the reaction mixture, quenched with 50% NaOH and taken up in methanol. GC analysis showed 85% desired product. The catalyst was quenched by adding ethanolamine (64 g, 1.04 mol) and stirred for 30 mins. The reaction was quenched by adding 50% sodium hydroxide solution (5.0 kg) and then stirred for 2 hrs. The salts were removed by filtration and the top acetonitrile layer of the filtrate (3.9 kg) was collected. The salts were washed with acetonitrile (500 ml) and then the aqueous layer was extracted once with acetonitrile. The combined acetonitrile layers were concentrated on a rotary evaporator (1.3 kg). GC analysis showed 87% conversion to the title product and 13% ethanolamine present. The concentrate was purified by vacuum distillation to give the product as a clear liquid (900 g, 65% theor. yield). $^1$H NMR (400 MHz, CDCl$_3$) d 1.30 (s, 4H), 2.87 (t, J=5.2 Hz, 4H), 3.58 (t, J=5.2 Hz, 4H), 4.70 (s, 2H)

Comparative Example 9.1

Ethanolamine hydrochloride (250 g, 2.6 mol) was suspended in a mixture of dimethylsulfoxide (12.5 g) and toluene (480 g) at room temperature. Paraformaldehyde (42 g, 1.3 mol) was added and the suspension was heated to 40° C. for 30 mins. Concentrated sulfuric acid (12.5 g, 0.1 mol) was added and the solution was heated at 40-45° C. for 1 hour. Then it was stirred at room temperature for the next 2 hr. An aliquot was taken from the reaction mixture, quenched with 50% NaOH and taken up in methanol. GC analysis showed conversion of 69% (desired product) and 31% ethanolamine present. The reaction was quenched by adding 50% sodium hydroxide solution (400 g) and stirred for 1 hr. The salts were removed by filtration and the filtrate was collected. The top layer of the filtrate was separated and then concentrated on a rotary evaporator. The concentrated residue was purified by vacuum distillation to give the product as a clear liquid (110 g, 59% yield).

Comparative Example 9.2

Ethanolamine hydrochloride (25 g, 0.25 mol) and paraformaldehyde (30 g, 1.0 mol) were suspended in methylene chloride (250 g). Concentrated sulfuric acid (3 g) was added and the reaction mixture was stirred at room temperature. During the next hour, ethanolamine hydrochloride (25 g, 0.25 mol) and concentrated sulfuric acid (3 g) were added 3 times so that a total of 100 g ethanolamine hydrochloride and 12 g sulfuric acid had been added. The reaction was stirred for 18 hours and then quenched by addition of 50% sodium hydroxide solution (100 g). The aqueous layer was collected and distilled under vacuum to provide the desired product as a clear liquid (52 g, 78% yield).

Comparative Example 9.3

This comparative example highlights that different solvents can be used

Ethanolamine hydrochloride (2.0 kg, 20.5 mol), paraformaldehyde (0.3 kg, 10.0 mol) and tert-butyl methyl ether (2.8 kg) were charged to a jacketed reactor. The reaction was warmed up to 41° C. and 95% sulfuric acid (0.1 kg) was added in one portion. The reaction mixture was stirred for 1 hr at 45° C. and cooled down to 10° C. An aliquot was taken from the reaction mixture, quenched with 50% NaOH and taken up in methanol. GC analysis showed conversion of 73% to the desired product and 27% ethanolamine present. The catalyst was quenched by adding ethanolamine (150 g) and stirring for 1 hr. The reaction was quenched by adding 50% sodium hydroxide solution (5.0 kg) and stirring for 1 hr. The solvent was removed on a rotary evaporator and the residue was filtered. The top layer of the filtrate was collected (1.3 kg) and the bottom layer (4.5 kg) was extracted with isopropanol (1 kg). The isopropanol extract was combined with the top organic layer and washed once with 50% sodium hydroxide solution. The organic layer was then distilled under vacuum to provide the desired product as a clear liquid (810 g, 59% yield).

Comparative Example 9.4

Ethanolamine hydrochloride (5.0 kg, 51 mol) and paraformaldehyde (0.8 kg, 27 mol) were charged to a 10 L jacketed reactor set to 20° C. Reactor was equipped with a very efficient stirrer. Concentrated sulfuric acid (0.6 kg, 6 mol) was then added slowly to the solid mixture under slow stirring. The resulting thick slurry was stirred for 4 hours and then left overnight. The reaction mixture solidified. The reaction mixture solids were slowly added in small portions into a vigorously stirred 50% NaOH solution (10 kg) in another reactor. The suspension was stirred for 2 hours and then filtered to remove the salts. The top layer from the filtrate was separated. The filtered salts were added to the lower aqueous layer and it was filtered again to remove the salts. The top layer was separated again and combined with the other top layer. The combined layers were distilled using a wipe film evaporator and then distilled under vacuum to provide the desired product as a clear oil (1.3 kg, 37% yield).

Comparative Example 9.5

Ethanolamine hydrochloride (100 g, 1.0 mol) was suspended in dichloromethane (500 g) at room temperature. Paraformaldehyde (15 g, 0.5 mol) was added along with catalytic amount of methanol (1.5 g). Boron trifluoride etherate (22 ml, 0.18 mol) was then added and the solution was stirred at room temperature for 1 hr during which time the reaction contents solidified. The reaction was quenched by adding 50% sodium hydroxide solution (100 g) and then stirred for 1 hr. The salts were removed by filtration and the filtrate was collected. The filtrate was concentrated on a rotary evaporator. The concentrated residue was then purified by vacuum distillation to give the product as a clear liquid (25 g, 37% yield).

Comparative Example 9.6

The table below highlights the broad the scope of the invention with respect to solvent, catalyst, aminoalcohol and aldehyde. The molar equivalents of aldehyde are with respect to moles of ethanolamine hydrochloride. The conversion is judged by analysis of reaction mixture by gas chromatography. The amount of catalyst is stated as weight % of amino alcohol salt (Formula (3).

| Eq. of aldehyde | Aldehyde or equivalent | Aminoalcohol salt-Formula (3) | SOLVENT | CATALYST | TEMP | % CONV. |
|---|---|---|---|---|---|---|
| 0.55 | paraformaldehyde | Ethanolamine HCl | Acetone | $H_2SO_4$, 10% | 40° C. | 74% |
| 0.52 | paraformaldehyde | Ethanolamine HCl | Acetonitrile | $H_2SO_4$, 10% | 45° C. | 86% |
| 0.52 | paraformaldehyde | Ethanolamine HCl | Acetonitrile | $SiCl_4$, 10% | 23° C. | 90% |
| 0.50 | paraformaldehyde | Ethanolamine HCl | Acetonitrile | $SiCl_4/H_2O$, 10% | 23° C. | 80% |
| 0.55 | paraformaldehyde | Ethanolamine HCl | Acetonitrile | $SiCl_4/H_2O$, 10% | 46° C. | 76% |
| 0.55 | paraformaldehyde | Ethanolamine HCl | Acetonitrile | $SiCl_4/H_2O$, 10% | 0° C. | 81% |
| 0.55 | paraformaldehyde | Ethanolamine HCl | Acetonitrile | $SOCl_2$ | 25° C. | 60% |
| 0.52 | paraformaldehyde | Ethanolamine HCl | none | 37% aq. HCl | 50° C. | 30% |
| 0.60 | paraformaldehyde | Ethanolamine HCl | 1,2-Dichloroethane | BF3•OEt2, 10% | 23° C. | 64% |
| 0.50 | paraformaldehyde | Ethanolamine HCl | 1,2-Dichloroethane | H2SO4, 10% | 60° C. | 57% |
| 0.60 | paraformaldehyde | Ethanolamine HCl | Dichloromethane | H2SO4, 5% | 23° C. | 50% |
| 1.00 | paraformaldehyde | Ethanolamine HCl | Dichloromethane | H2SO4, 10% | 23° C. | 81% |
| 0.52 | paraformaldehyde | Ethanolamine HCl | MTBE | SiCl4/H2O, 10% | 50° C. | 70% |
| 0.55 | paraformaldehyde | Ethanolamine HCl | MTBE | SiCl4/H2O, 10% | 22° C. | 76% |
| 0.52 | paraformaldehyde | Ethanolamine HCl | MTBE | H2SO4, 10% | 40° C. | 74% |
| 0.55 | paraformaldehyde | Ethanolamine HCl | none | Sulfuric acid, 96% | 23° C. | 73% |
| 0.50 | paraformaldehyde | Ethanolamine HCl | THF | H2SO4, 5% | 65° C. | 50% |
| 0.52 | paraformaldehyde | Ethanolamine HCl | Toluene | conc. HCl, 10% | 50° C. | 63% |
| 0.55 | paraformaldehyde | Ethanolamine HCl | Toluene | H2SO4, 5% | 46° C. | 70% |
| 0.53 | paraformaldehyde | Ethanolamine HCl | Toluene | MsOH, 5% | 50° C. | 67% |
| 0.53 | paraformaldehyde | Ethanolamine HCl | Toluene/Propylene carbonate 2.4:1 | H2SO4, 5% | 45° C. | 70% |
| 0.52 | paraformaldehyde | Ethanolamine HCl | Toluene/DMSO 40:1 | H2SO4, 5% | 40° C. | 74% |
| 0.52 | paraformaldehyde | Ethanolamine HCl | Toluene/DMSO 35:1 | MsOH, 5% | 42° C. | 81% |
| 0.52 | paraformaldehyde | Ethanolamine HCl | Methyl ethyl ketone | H2SO4, 5% | 50° C. | 76% |
| 0.52 | paraformaldehyde | Ethanolamine HCl | 1,2-dichloroethane | H2SO4, 5% | 50° C. | 50% |
| 1.0 | acetaldehyde | Ethanolamine HCl | Dichloromethane | SiCl4 | 20° C. | 10% |
| 1.0 | acetaldehyde | 2-Amino-1-propanol HCl | Dichloromethane | SiCl4 | 20° C. | 5% |
| 1.0 | acetaldehyde | 2-Amino-2-methyl-1-propanol | Dichloromethane | SiCl4 | 20° C. | 10% |
| 1.0 | 1,3,5-Trioxane | Ethanolamine HCl | 1,2-Dichloroethane | H2SO4, 10% | 20° C. | 65% |
| 1.0 | 1,3,5-Trioxane | Ethanolamine HCl | Dichloromethane | BF3•OEt2, 25% | 20° C. | 66% |
| 0.5 | Methyl chloromethyl ether | Ethanolamine HCl | 1,2-Dichloroethane | none | 20° C. | 42% |

MsOH = methanesulfonic acid;
MTBE = Methyl tert-butyl ether

Example 10. Synthesis of bis(2-aminopropoxy)methane

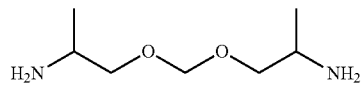

2-Aminopropanol hydrochloride (2.2 kg, 20 mol), paraformaldehyde (300 g, 10 mol) and acetonitrile (2.7 kg) were charged to a 10 L jacketed reactor and the jacket temperature was set to 20° C. Silicon tetrachloride (25 ml, 0.2 mol) was added in one portion and the reaction was stirred for 20 h. An aliquot was taken from the reaction mixture, quenched with 50% NaOH and taken up in methanol. GC analysis showed 85% desired product and 15% starting material (2-aminopropanol). The reaction was quenched by initially adding 2-aminopropanol (66 g, 0.88 mol) and then adding 50% NaOH solution (3.0 kg, 37 mol). The reaction mixture was stirred for 2 hrs and the inorganic salts were removed by filtration. The filtrate separated into two layers. The top organic layer was collected and concentrated using a rotary evaporator and the concentrate was collected (1.8 kg). Analysis of the concentrate showed it contained 70% of the desired product (weight by weight assay). It was purified by vacuum distillation to give the product as a clear liquid (1.04 kg, 64% yield). $^1$H NMR (400 MHz, CDCl$_3$) d 1.05 (d, J=6.4 Hz, 6H), 1.41 (s, 4H), 3.00-3.20 (m, 2H), 3.20-3.30 (m, 4H), 3.45-3.50 (m, 4H), 4.70 (s, 2H).

Comparative Example 10.1

2-Aminopropanol hydrochloride (446 g, 4.0 mol) and paraformaldehyde (60 g, 2.0 mol) were suspended in tert-butyl methyl ether (500 g). The suspension was heated to 40° C. and concentrated sulfuric acid (11 g, 0.1 mol) was added. The reaction mixture was stirred for 24 h. An aliquot was taken from the reaction mixture, quenched with 50% NaOH and taken up in methanol. GC analysis showed conversion of 73% (desired product) and 27% ethanolamine. The reaction was quenched by adding 50% sodium hydroxide solution (640 g) and stirred for 30 mins. The salts were removed by filtration and the top layer of the filtrate was collected. The lower aqueous layer was extracted with MTBE and added to the top layer. The combined organic layers were concentrated (350 g) and analysis of the concentrate showed it contained 61% of the desired product. It was purified by vacuum distillation to give the product as a clear liquid (145 g, 45% yield).

Example 11. Synthesis of bis(2-aminobutoxy)methane

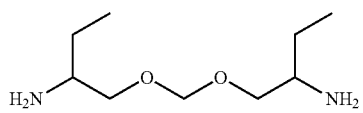

Toluene (500 g) and concentrated hydrochloric acid (280 g, 37%) were charged to a 2-L flask cooled to 10° C. 2-Amino-1-butanol (250 g, 2.8 mol) was added to the bi-phasic solution from a dropping funnel over 2 hrs. The ice-bath was removed and a Dean-Stark condenser was set up. The solution was heated to reflux and water collected (170 g) over the next 18 hrs. The distillation was continued to remove approximately 300 g of toluene. Acetonitrile (400 g) was added along with paraformaldehyde (42 g, 1.4 mol) and silicon tetrachloride (4 ml, 0.03 mol). The reaction mixture was stirred for 2 days during which time solids precipitated out. The reaction was quenched by adding 50% sodium hydroxide (650 g) and then stirred for 1 h. The salts were removed by filtration. The top layer of the filtrate was separated and then concentrated on a rotary evaporator. The concentrated residue was purified by vacuum distillation to give the product as a clear liquid (110 g, 42% yield). $^1$H NMR (400 MHz, CDCl$_3$) d 0.95 (t, J=6.4 Hz, 6H), 1.25-1.35 (m, 2H), 1.45-1.55 (m, 2H), 1.70 (s, 4H), 2.80-2.95 (m, 2H), 3.31 (dd, J=8.0 Hz, 9.6 Hz, 2H), 3.54 (dd, J=3.6 Hz, 9.6 Hz, 2H), 4.72 (s, 2H).

Example 12. Synthesis of bis(2-amino-2-methyl-propoxy)methane

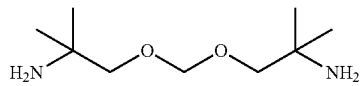

2-Amino-2-methylpropanol hydrochloride (110 g, 0.88 mol) and paraformaldehyde (26 g, 0.9 mol) were suspended in methylene chloride (700 g). Concentrated sulfuric acid (10 g) was added and the reaction mixture was stirred at room temperature. After 1 hour, another portion of 2-amino-2-methylpropanol hydrochloride (105 g, 0.84 mol) and concentrated sulfuric acid (15 g) were added. The reaction was stirred for 18 hours, during which time solids precipitated out. The solvent was removed by decantation and the solids were quenched by adding 50% sodium hydroxide solution (250 g). After 1 hour of stirring, two layers formed. The top layer was collected and distilled under vacuum to provide the desired product as a clear liquid (15 g, 9% yield). $^1$H NMR (400 MHz, CDCl$_3$) 1.11 (s, 12H), 1.29 (br s, 4H), 3.29 (s, 4H), 4.73 (s, 2H).

Example 13. Novel Polyaminoacetal Compositions and their Applications

In an aspect, ammonium salts of polyaminoacetals (i.e. Formula (1)) are novel compositions and have never been conceived of, or otherwise documented, in the prior art. With regard to industrial polymer and plastic applications, ammonium salts of type Formula (1) are useful as precursors for the manufacture of polyaminoacetals of type Formula (2). By virtue of being diamines (i.e., containing two NH$_2$ groups), the polyaminoacetal of type Formula (2) can serve as monomers or cross-linkers for polymer, thermoset, and plastic applications, and may be useful for polyurethane, nylon, acrylamides, polyurea, hydrogels, epoxy, polyimide and in other industries which rely, in part, on the use of diamines as building blocks (i.e., as raw material inputs) for their generation. Due to the lack of suitable synthetic methods, the use of polyaminoacetals of type Formula (2) in the aforementioned applications has, in part, been limited. This is despite the fact that polyaminoacetals may provide performance benefits and/or new features (i.e. recyclable properties or controlled degradation properties) to polymer systems.

In an aspect, the molecular compositions

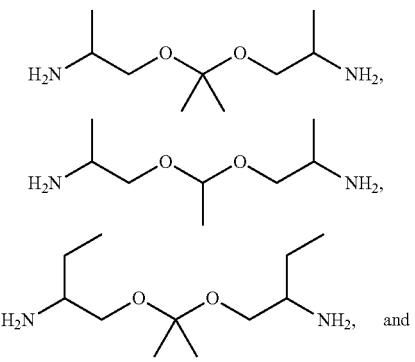

and

-continued

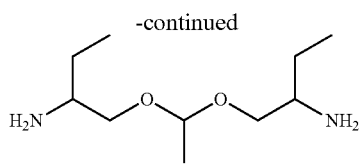

are novel polyaminoacetal structures and have not been conceived of, or otherwise documented, in the prior art. Such novel molecules could find use in polymer, thermoset, and plastic applications. As one example, novel polyamino acetals molecules were used as a curing agent for epoxy resin, and the mechanical and physical properties of the cured thermoset evaluated. The novel polyaminoacetals were benchmarked against Jeffamine® D230 as a control. Polyetheramines such as Jeffamine D230 (Huntsman Corporation) are produced in industrial quantities (e.g. >kT quantities) and find widespread commercial use, including many non-epoxy applications. With regard to epoxy applications, polyetheramines such as D230 are one of the most widely used amine curing agents by volume, with applications in adhesives, coatings, and composites (e.g, fiber reinforced plastics). For example, polyetheramines can be found in epoxy formulations in epoxy-based flooring. For example, polyetheramines are found in epoxy formulations for epoxy-based fiberglass (or carbon fiber) windmill blades. Polyetheramines are workhorse curing agents because of the combination processing and mechanical properties they provide to epoxy resins. The amino group attachment in the most prevalent polyetheramines is via secondary carbon atoms. This provides steric hindrance around the amino group, resulting in slower epoxy reactivity, relative to other polyamines, whereby the amino attachment point is via a primary carbon atom. Slower amine/epoxy reactivity is important in applications that require longer epoxy composition working times prior to curing (e.g., the infusion of a very large composite structures). Additionally, a lower epoxy/amine reactivity is important for manufacturing processes that require a large volume of the epoxy compositions to be used (e.g, pultrusion, e.g., filament winding), as the exotherm that develops in the resin bath will be less. From the standpoint of cured epoxy properties, polyetheramines generally provide good flexural properties and toughness to the epoxy thermoset. However, these benefits usually come at the expense of lower than desired glass transition temperature [Tg], and chemical resistance. This is among the reasons why, for example, polyetheramines are not often used as the "stand alone" curing agent in contemporary epoxy composition for windmill blade applications, which instead typically comprise a mixture of a polyetheramine, and a cycloaliphatic amine such as 1,3-BAC (Mitsubishi Gas Chemical Corporation) or IPDA (isophorone diamine; Evonik Industries).

The data in Table 1 serves to illustrate how specific novel polyaminoacetals of type Formula (2) of this invention provide certain advantages over the polyetheramine Jeffamine® D230, but while also maintaining the processing attribute of long working time. As determined by pot life experiments, the use of polyaminoacetal as the curing agent for EPON 828 (Hexion Corporation), all demonstrate similar working times as Jeffamine® D230. Additionally, the epoxy resin cured with the novel polyaminacetal provided a cured matrix with ultimate tensile strength, tensile elongation and ultimate flexural strength superior to that of the Jeffamine® D230-cured matrix. Importantly, the Tg of the polyaminoacetal-cured matrix were also higher.

TABLE 1

| Polyamine Hardener Comparison | | | | [1]Jeffamine ®D-230 |
|---|---|---|---|---|
| AEW | 47.5 | 44.1 | 54.6 | 60 |
| PPH amine/100 part resin[2] | 25 | 23.5 | 29 | 32 |
| Pot Life, min (100 g mass, 21° C.) | >4 h | >4 h | >4 h | >4 h |
| [3]Tg., ° C. | 109-115 | 96 | 109 | 90[4] |
| [5]Tensile Strength, psi | 11,790 | 10,920 | 10,762 | 10,020 |
| Tensile Modulus, psi | 550,000 | 442,900 | 433,518 | 493,090 |
| % elongation at break | 6.1 | 8.1 | 6.3 | 5.1 |
| [6]Flexural Strength, psi | 17,290 | 16,300 | 17,680 | 15,380 |
| Flexural Modulus, psi × $10^5$ | 4.8 | 4.4 | 4.2 | 4.7 |
| Cured Epoxy Recyclability | Yes[7] | Yes[7] | Yes[7] | No |

[1]a product of Huntsman Corporation
[2]general DGEBA used; EEW = 188 (EPON 828)
[3]Tg determined via DSC; curing profile: room temperature overnight, then 2 hr @ 80° C.; then 1 hr @ 120° C
[4]Tg obtained from Jeffamine D230 technical data sheet.
[5]ASTM D638
[6]ASTM D790
[7]Cured epoxy composition was recycled in 25% acetic acid solution, yielding >90% recover of an thermoplastic epoxy material

We claim:

1. A process for preparing a salt of a compound represented by Formula (2-1):

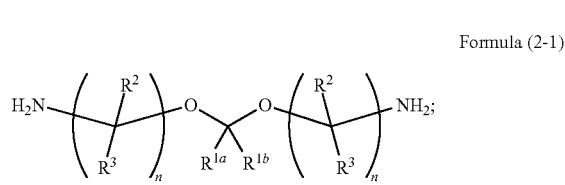

Formula (2-1)

wherein
R$^{1a}$ is selected from the group consisting of hydrogen and optionally substituted alkyl;
R$^{1b}$ is optionally substituted alkyl;
each occurrence of R$^2$ and R$^3$ is independently selected from the group consisting of hydrogen, optionally substituted alkyl, optionally substituted cycloalkyl; or
optionally substituted aryl, or R$^2$ and R$^3$ can combine with each other to form optionally substituted cycloalkyl; and
each instance of n is the same integer ranging from 1 to 20,
the process comprising the reaction of an aldehyde equivalent or ketone equivalent with a salt of a compound represented by Formula (3) to produce the salt of the compound of Formula (2-1):

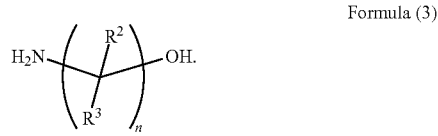

Formula (3)

2. The process of claim 1, wherein each n is 2.
3. The process of claim 1, wherein the salt of the compound represented by Formula (2-1) is a salt represented by Formula (1-1):

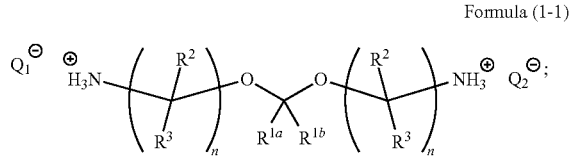

Formula (1-1)

wherein
R$^{1a}$ is selected from the group consisting of hydrogen and optionally substituted alkyl;
R$^{1b}$ K is optionally substituted alkyl;
each occurrence of R$^2$ and R$^3$ is independently selected from the group consisting of hydrogen, optionally substituted alkyl, optionally substituted cycloalkyl, and optionally substituted aryl, or
R$^2$ and R$^3$ can combine with each other to form optionally substituted cycloalkyl;
each n is an integer ranging from 1 to 20; and
each of Q$^{1\ominus}$ and Q$^{2\ominus}$ is independently a counterion.
4. The process of claim 3, wherein Q$^{1\ominus}$ and Q$^{2\ominus}$ are both chloride.

5. The process of claim 1, wherein the salt of the compound represented by Formula (2-1) is a salt of the compound represented by Formula (1-a-II):

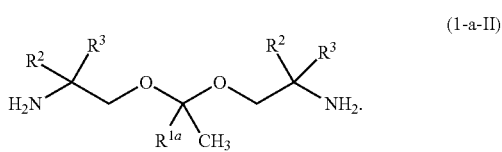

(1-a-II)

6. The process of claim 1, wherein the salt of the compound represented by Formula (2-1) is a salt of the compound represented by Formula (1-a-II):

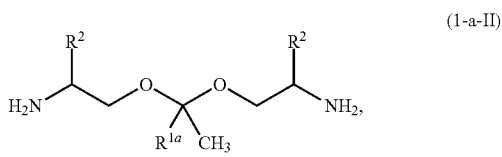

(1-a-II)

wherein R$^2$ is unsubstituted C$_{1-6}$ alkyl and R$^{1a}$ is independently selected from the group consisting of hydrogen and —CH$_3$.

7. The process of claim 1, wherein the ketone equivalent is selected from the group consisting of 2,2-dimethoxypropane, 2-methoxypropene, 2,2-diethoxypropane; and 2-ethoxypropene.
8. The process of claim 7, wherein the ketone equivalent is selected from the group consisting of 2,2-dimethoxypropane and 2-methoxypropene.
9. The process of claim 8, wherein the ketone equivalent is 2,2-dimethoxypropane.
10. The process of claim 8, wherein the ketone equivalent is 2-methoxypropene.
11. The process of claim 1, wherein the aldehyde equivalent is selected from the group consisting of 1,1-dimethoxyethane; methyl vinyl ether, 1,1-diethoxyethane, and ethyl vinyl ether.
12. The process of claim 1, wherein the salt of the compound of Formula (3) is selected from the group consisting of:

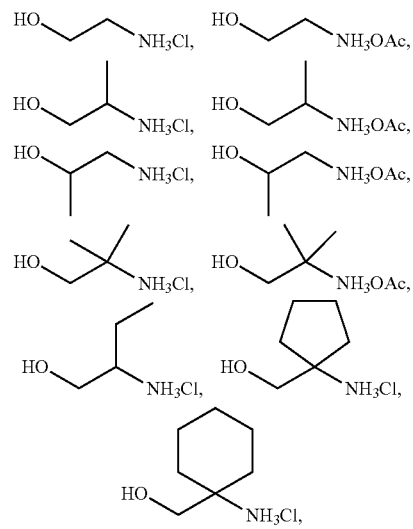

107

-continued

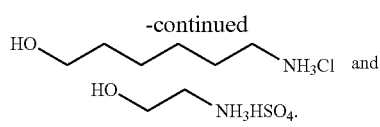

13. The process of claim 1, further comprising contacting the salt of the compound of Formula (1-1) with a base to produce the compound of Formula (2-1).

14. The process of claim 6, wherein the compound of Formula (2-1) is selected from the group consisting of:

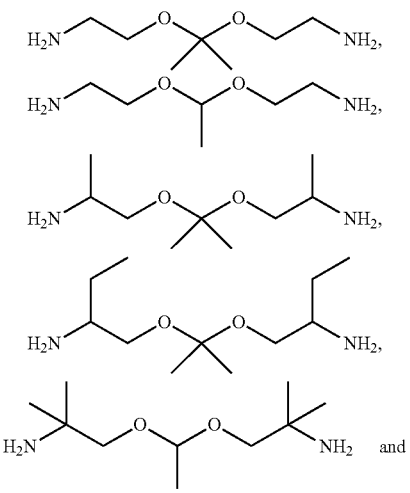

108

-continued

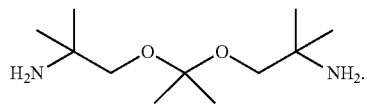

15. The process of claim 1, wherein the reaction is carried out in the presence of a solvent.

16. The process of claim 1, wherein the compound of Formula (2) is represented by:

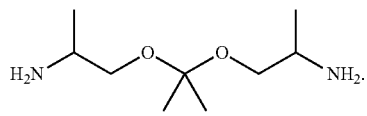

17. The process of claim 1, wherein the compound of Formula (2) is represented by:

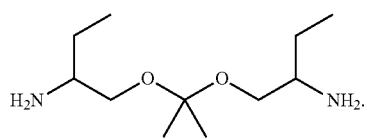

* * * * *